United States Patent
Shelton, IV et al.

(10) Patent No.: US 12,285,185 B2
(45) Date of Patent: *Apr. 29, 2025

(54) POWERED STAPLING DEVICE CONFIGURED TO ADJUST FORCE, ADVANCEMENT SPEED, AND OVERALL STROKE OF CUTTING MEMBER BASED ON SENSED PARAMETER OF FIRING OR CLAMPING

(71) Applicant: Cilag GmbH International, Zug (CH)

(72) Inventors: Frederick E. Shelton, IV, Hillsboro, OH (US); Gregory J. Bakos, Mason, OH (US); Jason L. Harris, Lebanon, OH (US); Chester O. Baxter, III, Loveland, OH (US)

(73) Assignee: Cilag GmbH International, Zug (CH)

( * ) Notice: Subject to any disclaimer, the term of this patent is extended or adjusted under 35 U.S.C. 154(b) by 0 days.

This patent is subject to a terminal disclaimer.

(21) Appl. No.: 18/403,508

(22) Filed: Jan. 3, 2024

(65) Prior Publication Data

US 2024/0130754 A1   Apr. 25, 2024

Related U.S. Application Data

(62) Division of application No. 16/182,240, filed on Nov. 6, 2018, now abandoned.

(Continued)

(51) Int. Cl.
*A61B 17/00* (2006.01)
*A61B 17/068* (2006.01)
(Continued)

(52) U.S. Cl.
CPC .... *A61B 17/320016* (2013.01); *A61B 17/068* (2013.01); *A61B 17/1155* (2013.01);
(Continued)

(58) Field of Classification Search
CPC .......... A61B 17/320016; A61B 17/068; A61B 17/1155; A61B 18/00; A61B 18/1206;
(Continued)

(56) References Cited

U.S. PATENT DOCUMENTS 4,962,681 A   10/1990   Yang
4,976,173 A   12/1990   Yang
(Continued)

FOREIGN PATENT DOCUMENTS

EP   3078334 A1   10/2016
JP   H05337119 A   12/1993
(Continued)

OTHER PUBLICATIONS

"ATM-MPLS Network Interworking Version 2.0, af-aic-0178.001" ATM Standard, The ATM Forum Technical Committee, published Aug. 2003.
(Continued)

*Primary Examiner* — Robert F Long

(57) ABSTRACT

A powered stapling device includes a circular stapling head assembly, an anvil, a trocar coupled to the anvil, and a motor also coupled to the trocar. The motor is configured to advance and retract the trocar. The device further includes a control circuit coupled to the motor, in which the control circuit is configured to determine a position of the trocar in one of a plurality of zones, and set an anvil closure rate based on the determined position of the trocar.

6 Claims, 35 Drawing Sheets

Related U.S. Application Data

(60) Provisional application No. 62/729,185, filed on Sep. 10, 2018, provisional application No. 62/692,768, filed on Jun. 30, 2018, provisional application No. 62/692,748, filed on Jun. 30, 2018, provisional application No. 62/692,747, filed on Jun. 30, 2018, provisional application No. 62/659,900, filed on Apr. 19, 2018, provisional application No. 62/650,877, filed on Mar. 30, 2018, provisional application No. 62/650,898, filed on Mar. 30, 2018, provisional application No. 62/650,882, filed on Mar. 30, 2018, provisional application No. 62/650,887, filed on Mar. 30, 2018, provisional application No. 62/640,417, filed on Mar. 8, 2018, provisional application No. 62/640,415, filed on Mar. 8, 2018, provisional application No. 62/611,340, filed on Dec. 28, 2017, provisional application No. 62/611,341, filed on Dec. 28, 2017, provisional application No. 62/611,339, filed on Dec. 28, 2017.

(51) Int. Cl.
| | | |
|---|---|---|
| *A61B 17/115* | (2006.01) | |
| *A61B 17/32* | (2006.01) | |
| *A61B 18/00* | (2006.01) | |
| A61B 17/072 | (2006.01) | |
| A61B 17/29 | (2006.01) | |
| A61B 18/12 | (2006.01) | |
| A61B 18/14 | (2006.01) | |
| A61B 34/20 | (2016.01) | |
| A61B 34/30 | (2016.01) | |
| A61B 34/37 | (2016.01) | |
| A61B 90/00 | (2016.01) | |
| G16H 20/40 | (2018.01) | |
| G16H 30/40 | (2018.01) | |
| G16H 40/67 | (2018.01) | |
| G16H 50/20 | (2018.01) | |
| H04L 67/10 | (2022.01) | |

(52) U.S. Cl.
CPC .... *A61B 18/00* (2013.01); *A61B 2017/00017* (2013.01); *A61B 2017/00022* (2013.01); *A61B 2017/00026* (2013.01); *A61B 2017/00044* (2013.01); *A61B 2017/00115* (2013.01); *A61B 2017/00199* (2013.01); *A61B 2017/00221* (2013.01); *A61B 2017/00398* (2013.01); *A61B 2017/00734* (2013.01); *A61B 2017/00809* (2013.01); *A61B 2017/07257* (2013.01); *A61B 2017/07285* (2013.01); *A61B 2017/2927* (2013.01); *A61B 2018/00601* (2013.01); *A61B 2018/0063* (2013.01); *A61B 18/1206* (2013.01); *A61B 2018/1253* (2013.01); *A61B 2018/126* (2013.01); *A61B 2018/1273* (2013.01); *A61B 2018/145* (2013.01); *A61B 2034/2048* (2016.02); *A61B 2034/2059* (2016.02); *A61B 34/30* (2016.02); *A61B 34/37* (2016.02); *A61B 2090/064* (2016.02); *A61B 2090/066* (2016.02); *A61B 90/361* (2016.02); *A61B 90/37* (2016.02); *A61B 2090/373* (2016.02); *A61B 2090/376* (2016.02); *A61B 2217/005* (2013.01); *A61B 2217/007* (2013.01); *G16H 20/40* (2018.01); *G16H 30/40* (2018.01); *G16H 40/67* (2018.01); *G16H 50/20* (2018.01); *H04L 67/10* (2013.01)

(58) Field of Classification Search
CPC ....... A61B 34/30; A61B 34/37; A61B 90/361; A61B 90/37; A61B 2017/00017; A61B 2017/00022; A61B 2017/00026; A61B 2017/00044; A61B 2017/00115; A61B 2017/00199; A61B 2017/00221; A61B 2017/00398; A61B 2017/00734; A61B 2017/00809; A61B 2017/07257; A61B 2017/07285; A61B 2017/2927; A61B 2018/00601; A61B 2018/0063; A61B 2018/1253; A61B 2018/126; A61B 2018/1273; A61B 2018/145; A61B 2034/2048; A61B 2034/2059; A61B 2090/064; A61B 2090/066; A61B 2090/373; A61B 2090/376; A61B 2217/005; A61B 2217/007; G16H 20/40; G16H 30/40; G16H 40/67; G16H 50/20; H04L 67/10

USPC .......................................... 227/175.1–182.1
See application file for complete search history.

(56) References Cited

U.S. PATENT DOCUMENTS

| | | | |
|---|---|---|---|
| 5,467,911 A | 11/1995 | Tsuruta et al. | |
| 5,796,188 A | 8/1998 | Bays | |
| 6,443,973 B1* | 9/2002 | Whitman | A61B 17/07207 227/176.1 |
| 6,695,199 B2 | 2/2004 | Whitman | |
| 6,793,652 B1* | 9/2004 | Whitman | A61B 17/00 606/1 |
| 6,981,941 B2* | 1/2006 | Whitman | A61B 34/71 606/1 |
| 7,644,848 B2 | 1/2010 | Swayze et al. | |
| 7,717,312 B2 | 5/2010 | Beetel | |
| 7,837,079 B2 | 11/2010 | Holsten et al. | |
| 7,982,776 B2 | 7/2011 | Dunki-Jacobs et al. | |
| 7,995,045 B2 | 8/2011 | Dunki-Jacobs | |
| 8,118,206 B2 | 2/2012 | Zand et al. | |
| 8,210,411 B2 | 7/2012 | Yates et al. | |
| 8,308,040 B2 | 11/2012 | Huang et al. | |
| 8,573,465 B2 | 11/2013 | Shelton, IV | |
| 8,627,993 B2 | 1/2014 | Smith et al. | |
| 8,685,016 B2* | 4/2014 | Wham | A61B 18/1442 606/51 |
| 8,820,607 B2 | 9/2014 | Marczyk | |
| 8,827,134 B2 | 9/2014 | Viola et al. | |
| 8,960,519 B2 | 2/2015 | Whitman et al. | |
| 8,989,903 B2 | 3/2015 | Weir et al. | |
| 9,005,230 B2 | 4/2015 | Yates et al. | |
| 9,038,882 B2 | 5/2015 | Racenet et al. | |
| 9,113,880 B2 | 8/2015 | Zemlok et al. | |
| 9,179,912 B2 | 11/2015 | Yates et al. | |
| 9,220,505 B2 | 12/2015 | Vasudevan et al. | |
| 9,283,054 B2 | 3/2016 | Morgan et al. | |
| 9,326,767 B2 | 5/2016 | Koch, Jr. et al. | |
| 9,345,481 B2 | 5/2016 | Hall et al. | |
| 9,358,003 B2 | 6/2016 | Hall et al. | |
| 9,445,813 B2 | 9/2016 | Shelton, IV et al. | |
| 9,463,022 B2 | 10/2016 | Swayze et al. | |
| 9,522,003 B2 | 12/2016 | Weir et al. | |
| 9,561,082 B2 | 2/2017 | Yen et al. | |
| 9,597,081 B2 | 3/2017 | Swayze et al. | |
| 9,629,623 B2 | 4/2017 | Lytle, IV et al. | |
| 9,675,354 B2 | 6/2017 | Weir et al. | |
| 9,750,499 B2 | 9/2017 | Leimbach et al. | |
| 9,757,128 B2 | 9/2017 | Baber et al. | |
| 9,788,836 B2 | 10/2017 | Overmyer et al. | |
| 9,804,618 B2 | 10/2017 | Leimbach et al. | |
| 9,808,246 B2* | 11/2017 | Shelton, IV | A61B 17/07207 |
| 9,833,254 B1 | 12/2017 | Barral et al. | |
| 9,867,612 B2 | 1/2018 | Parihar et al. | |
| 9,877,718 B2 | 1/2018 | Weir et al. | |
| 9,913,642 B2 | 3/2018 | Leimbach et al. | |
| 9,918,730 B2 | 3/2018 | Trees et al. | |
| 9,980,769 B2 | 5/2018 | Trees et al. | |
| 10,016,199 B2 | 7/2018 | Baber et al. | |

(56) References Cited

U.S. PATENT DOCUMENTS

| | | |
|---|---|---|
| 10,039,564 B2 | 8/2018 | Hibner et al. |
| 10,052,044 B2 | 8/2018 | Shelton, IV et al. |
| 10,092,355 B1 | 10/2018 | Hannaford et al. |
| 10,098,527 B2 | 10/2018 | Weisenburgh et al. |
| 10,133,248 B2 | 11/2018 | Fitzsimmons et al. |
| 10,136,887 B2 | 11/2018 | Shelton, IV et al. |
| 10,159,481 B2 | 12/2018 | Whitman et al. |
| 10,175,127 B2 | 1/2019 | Collins et al. |
| 10,190,888 B2 | 1/2019 | Hryb et al. |
| 10,201,364 B2 | 2/2019 | Leimbach et al. |
| 10,271,844 B2 | 4/2019 | Valentine et al. |
| 10,271,846 B2 | 4/2019 | Shelton, IV et al. |
| 10,271,851 B2 | 4/2019 | Shelton, IV et al. |
| 10,335,180 B2 | 7/2019 | Johnson et al. |
| 10,342,543 B2 | 7/2019 | Shelton, IV et al. |
| 10,357,247 B2 | 7/2019 | Shelton, IV et al. |
| 10,368,903 B2 | 8/2019 | Morales et al. |
| 10,420,558 B2 | 9/2019 | Nalagatla et al. |
| 10,426,467 B2 | 10/2019 | Miller et al. |
| 10,441,279 B2 | 10/2019 | Shelton, IV et al. |
| 10,595,887 B2 | 3/2020 | Shelton, IV et al. |
| 10,695,081 B2 | 6/2020 | Shelton, IV et al. |
| 10,743,872 B2 | 8/2020 | Leimbach et al. |
| 10,755,813 B2 | 8/2020 | Shelton, IV et al. |
| 10,758,310 B2 | 9/2020 | Shelton, IV et al. |
| 10,849,697 B2 | 12/2020 | Yates et al. |
| 10,881,399 B2 | 1/2021 | Shelton, IV et al. |
| 10,888,321 B2 | 1/2021 | Shelton, IV et al. |
| 10,892,899 B2 | 1/2021 | Shelton, IV et al. |
| 10,892,995 B2 | 1/2021 | Shelton, IV et al. |
| 10,898,622 B2 | 1/2021 | Shelton, IV et al. |
| 10,905,415 B2 | 2/2021 | DiNardo et al. |
| 10,912,567 B2 | 2/2021 | Shelton, IV et al. |
| 10,932,772 B2 | 3/2021 | Shelton, IV et al. |
| 10,932,784 B2 | 3/2021 | Mozdzierz et al. |
| 10,932,872 B2 | 3/2021 | Shelton, IV et al. |
| 10,943,454 B2 | 3/2021 | Shelton, IV et al. |
| 10,944,728 B2 | 3/2021 | Wiener et al. |
| 10,959,728 B2 | 3/2021 | Satti, III et al. |
| 10,966,791 B2 | 4/2021 | Harris et al. |
| 10,987,178 B2 | 4/2021 | Shelton, IV et al. |
| 11,013,563 B2 | 5/2021 | Shelton, IV et al. |
| 11,020,115 B2 | 6/2021 | Scheib et al. |
| 11,026,751 B2 | 6/2021 | Shelton, IV et al. |
| 11,045,591 B2 | 6/2021 | Shelton, IV et al. |
| 11,051,876 B2 | 7/2021 | Shelton, IV et al. |
| 11,056,244 B2 | 7/2021 | Shelton, IV et al. |
| 11,058,498 B2 | 7/2021 | Shelton, IV et al. |
| 11,069,012 B2 | 7/2021 | Shelton, IV et al. |
| 11,076,921 B2 | 8/2021 | Shelton, IV et al. |
| 11,096,693 B2 | 8/2021 | Shelton, IV et al. |
| 11,100,631 B2 | 8/2021 | Yates et al. |
| 11,114,195 B2 | 9/2021 | Shelton, IV et al. |
| 11,132,462 B2 | 9/2021 | Shelton, IV et al. |
| 11,147,607 B2 | 10/2021 | Yates et al. |
| 11,160,605 B2 | 11/2021 | Shelton, IV et al. |
| 11,166,772 B2 | 11/2021 | Shelton, IV et al. |
| 11,179,150 B2 | 11/2021 | Yates et al. |
| 11,179,175 B2 | 11/2021 | Houser et al. |
| 11,179,208 B2 | 11/2021 | Yates et al. |
| 11,202,570 B2 | 12/2021 | Shelton, IV et al. |
| 11,213,359 B2 | 1/2022 | Shelton, IV et al. |
| 11,234,756 B2 | 2/2022 | Shelton, IV et al. |
| 11,253,315 B2 | 2/2022 | Yates et al. |
| 11,257,589 B2 | 2/2022 | Shelton, IV et al. |
| 11,266,468 B2 | 3/2022 | Shelton, IV et al. |
| 11,273,001 B2 | 3/2022 | Shelton, IV et al. |
| 11,278,281 B2 | 3/2022 | Shelton, IV et al. |
| 11,284,936 B2 | 3/2022 | Shelton, IV et al. |
| 11,291,495 B2 | 4/2022 | Yates et al. |
| 11,298,128 B2 | 4/2022 | Messerly et al. |
| 11,304,720 B2 | 4/2022 | Kimball et al. |
| 11,304,745 B2 | 4/2022 | Shelton, IV et al. |
| 11,304,763 B2 | 4/2022 | Shelton, IV et al. |
| 11,308,075 B2 | 4/2022 | Shelton, IV et al. |
| 11,311,306 B2 | 4/2022 | Shelton, IV et al. |
| 11,317,937 B2 | 5/2022 | Nott et al. |
| 11,364,075 B2 | 6/2022 | Yates et al. |
| 11,373,755 B2 | 6/2022 | Shelton, IV et al. |
| 11,376,002 B2 | 7/2022 | Shelton, IV et al. |
| 11,410,259 B2 | 8/2022 | Harris et al. |
| 11,419,630 B2 | 8/2022 | Yates et al. |
| 11,419,667 B2 | 8/2022 | Messerly et al. |
| 11,423,007 B2 | 8/2022 | Shelton, IV et al. |
| 11,432,885 B2 | 9/2022 | Shelton, IV et al. |
| 11,446,052 B2 | 9/2022 | Shelton, IV et al. |
| 11,464,535 B2 | 10/2022 | Shelton, IV et al. |
| 11,464,559 B2 | 10/2022 | Nott et al. |
| 11,529,187 B2 | 12/2022 | Shelton, IV et al. |
| 11,540,855 B2 | 1/2023 | Messerly et al. |
| 11,571,234 B2 | 2/2023 | Nott et al. |
| 11,602,393 B2 | 3/2023 | Shelton, IV et al. |
| 11,607,239 B2 | 3/2023 | Swensgard et al. |
| 11,612,408 B2 | 3/2023 | Yates et al. |
| 11,612,444 B2 | 3/2023 | Shelton, IV et al. |
| 11,633,237 B2 | 4/2023 | Shelton, IV et al. |
| 11,666,331 B2 | 6/2023 | Shelton, IV et al. |
| 11,672,605 B2 | 6/2023 | Messerly et al. |
| 11,678,881 B2 | 6/2023 | Yates et al. |
| 11,696,760 B2 | 7/2023 | Shelton, IV et al. |
| 11,771,454 B2 | 10/2023 | Swensgard et al. |
| 11,771,487 B2 | 10/2023 | Shelton, IV et al. |
| 11,786,245 B2 | 10/2023 | Shelton, IV |
| 11,832,899 B2 | 12/2023 | Shelton, IV et al. |
| 11,844,579 B2 | 12/2023 | Shelton, IV et al. |
| 11,857,152 B2 | 1/2024 | Shelton, IV et al. |
| 11,864,728 B2 | 1/2024 | Shelton, IV et al. |
| 11,896,322 B2 | 2/2024 | Yates et al. |
| 11,896,443 B2 | 2/2024 | Shelton, IV et al. |
| 2004/0092992 A1 | 5/2004 | Adams et al. |
| 2004/0108825 A1 | 6/2004 | Lee et al. |
| 2005/0100867 A1 | 5/2005 | Hilscher et al. |
| 2005/0131390 A1 | 6/2005 | Heinrich et al. |
| 2007/0239028 A1 | 10/2007 | Houser et al. |
| 2007/0270884 A1* | 11/2007 | Smith ............... A61B 17/1114 606/1 |
| 2009/0090763 A1 | 4/2009 | Zemlok et al. |
| 2010/0065609 A1* | 3/2010 | Schwemberger .. A61B 17/1155 227/180.1 |
| 2010/0096431 A1* | 4/2010 | Smith ................ A61B 17/115 227/175.2 |
| 2010/0096435 A1* | 4/2010 | Fuchs ............... A61B 17/1155 227/179.1 |
| 2010/0198220 A1 | 8/2010 | Boudreaux et al. |
| 2010/0258327 A1 | 10/2010 | Esenwein et al. |
| 2011/0006101 A1* | 1/2011 | Hall ................... A61B 17/068 227/175.2 |
| 2011/0017801 A1* | 1/2011 | Zemlok ........... A61B 17/07207 227/175.1 |
| 2011/0022032 A1 | 1/2011 | Zemlok et al. |
| 2011/0121049 A1* | 5/2011 | Malinouskas .......... A61B 90/98 606/1 |
| 2011/0139851 A1* | 6/2011 | McCuen .......... A61B 17/07207 227/175.1 |
| 2011/0204119 A1* | 8/2011 | McCuen ............. A61B 17/068 227/175.1 |
| 2011/0209128 A1 | 8/2011 | Nikara et al. |
| 2011/0290855 A1* | 12/2011 | Moore ................. A61B 34/30 227/176.1 |
| 2011/0295269 A1* | 12/2011 | Swensgard ........... A61B 34/76 606/130 |
| 2011/0306840 A1 | 12/2011 | Allen et al. |
| 2012/0101488 A1 | 4/2012 | Aldridge et al. |
| 2012/0205421 A1* | 8/2012 | Shelton, IV .......... A61B 50/24 227/177.1 |
| 2012/0223121 A1* | 9/2012 | Viola ............. A61B 17/07207 227/175.1 |
| 2013/0008677 A1 | 1/2013 | Huifu |
| 2013/0168435 A1 | 7/2013 | Huang et al. |
| 2013/0175318 A1* | 7/2013 | Felder ................ A61B 17/115 227/175.1 |
| 2013/0197531 A1 | 8/2013 | Boukhny et al. |
| 2014/0148803 A1 | 5/2014 | Taylor |

(56) References Cited

U.S. PATENT DOCUMENTS

| | | | |
|---|---|---|---|
| 2014/0151429 A1* | 6/2014 | Scheib | A61B 17/1155 227/175.1 |
| 2014/0249557 A1* | 9/2014 | Koch, Jr. | A61B 17/07207 606/170 |
| 2014/0263552 A1 | 9/2014 | Hall et al. | |
| 2014/0263565 A1* | 9/2014 | Lytle, IV | A61B 17/07207 227/180.1 |
| 2014/0309666 A1* | 10/2014 | Shelton, IV | A61B 17/115 606/139 |
| 2015/0053743 A1 | 2/2015 | Yates et al. | |
| 2015/0053746 A1 | 2/2015 | Shelton, IV et al. | |
| 2015/0076206 A1* | 3/2015 | Sapre | A61B 17/068 227/175.2 |
| 2015/0083774 A1* | 3/2015 | Measamer | A61B 17/068 227/175.1 |
| 2015/0145682 A1 | 5/2015 | Harris | |
| 2015/0182220 A1 | 7/2015 | Yates et al. | |
| 2015/0196295 A1 | 7/2015 | Shelton, IV et al. | |
| 2015/0257783 A1 | 9/2015 | Levine et al. | |
| 2015/0272575 A1* | 10/2015 | Leimbach | A61B 90/96 227/175.3 |
| 2015/0272583 A1* | 10/2015 | Leimbach | A61L 2/087 227/176.1 |
| 2015/0282866 A1* | 10/2015 | Rothweiler | A61B 18/1445 606/51 |
| 2016/0174998 A1 | 6/2016 | Lal et al. | |
| 2016/0265938 A1* | 9/2016 | Hryb | A61B 17/072 |
| 2016/0314716 A1 | 10/2016 | Grubbs | |
| 2016/0314717 A1 | 10/2016 | Grubbs | |
| 2016/0317172 A1 | 11/2016 | Kumada et al. | |
| 2016/0374672 A1* | 12/2016 | Bear | H02J 7/00 606/219 |
| 2016/0374673 A1* | 12/2016 | Stager | A61B 17/1155 227/176.1 |
| 2016/0379504 A1 | 12/2016 | Bailey et al. | |
| 2017/0209145 A1 | 7/2017 | Swayze et al. | |
| 2017/0249431 A1 | 8/2017 | Shelton, IV et al. | |
| 2017/0296183 A1* | 10/2017 | Shelton, IV | A61B 17/072 |
| 2018/0056496 A1 | 3/2018 | Rubens et al. | |
| 2018/0353186 A1* | 12/2018 | Mozdzierz | A61B 17/072 |
| 2019/0059986 A1 | 2/2019 | Shelton, IV et al. | |
| 2019/0200906 A1 | 7/2019 | Shelton, IV et al. | |
| 2019/0200980 A1 | 7/2019 | Shelton, IV et al. | |
| 2019/0200987 A1 | 7/2019 | Shelton, IV et al. | |
| 2019/0200997 A1 | 7/2019 | Shelton, IV et al. | |
| 2019/0201021 A1 | 7/2019 | Shelton, IV et al. | |
| 2019/0201034 A1 | 7/2019 | Shelton, IV et al. | |
| 2019/0201039 A1 | 7/2019 | Widenhouse et al. | |
| 2019/0201042 A1 | 7/2019 | Nott et al. | |
| 2019/0201087 A1 | 7/2019 | Shelton, IV et al. | |
| 2019/0201090 A1 | 7/2019 | Shelton, IV et al. | |
| 2019/0201102 A1 | 7/2019 | Shelton, IV et al. | |
| 2019/0201112 A1 | 7/2019 | Wiener et al. | |
| 2019/0201113 A1 | 7/2019 | Shelton, IV et al. | |
| 2019/0201115 A1 | 7/2019 | Shelton, IV et al. | |
| 2019/0201118 A1 | 7/2019 | Shelton, IV et al. | |
| 2019/0201130 A1 | 7/2019 | Shelton, IV et al. | |
| 2019/0201139 A1 | 7/2019 | Shelton, IV et al. | |
| 2019/0201140 A1 | 7/2019 | Yates et al. | |
| 2019/0201142 A1 | 7/2019 | Shelton, IV et al. | |
| 2019/0201146 A1 | 7/2019 | Shelton, IV et al. | |
| 2019/0205567 A1 | 7/2019 | Shelton, IV et al. | |
| 2019/0206555 A1 | 7/2019 | Morgan et al. | |
| 2019/0206561 A1 | 7/2019 | Shelton, IV et al. | |
| 2020/0405304 A1 | 12/2020 | Mozdzierz et al. | |
| 2022/0061836 A1 | 3/2022 | Parihar et al. | |

FOREIGN PATENT DOCUMENTS

| | | |
|---|---|---|
| JP | 2014171904 A | 9/2014 |
| WO | WO-9734533 A1 | 9/1997 |
| WO | WO-2007137304 A2 | 11/2007 |

OTHER PUBLICATIONS

IEEE Std 802.3-2012 (Revision of IEEE Std 802.3-2008, published Dec. 28, 2012.

* cited by examiner

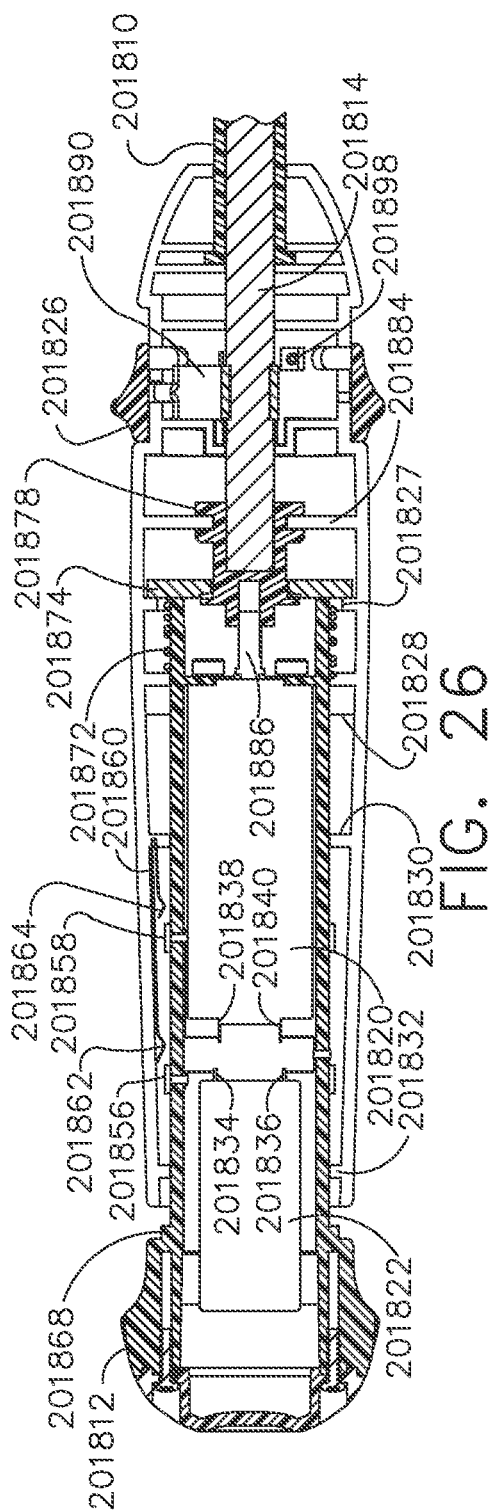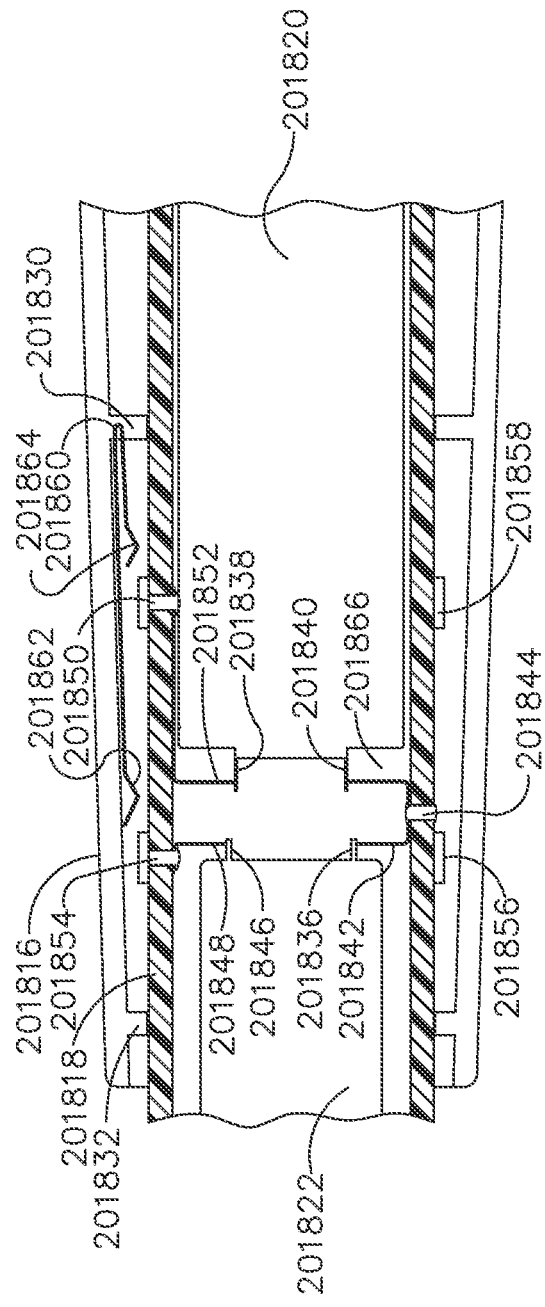
FIG. 26
FIG. 27

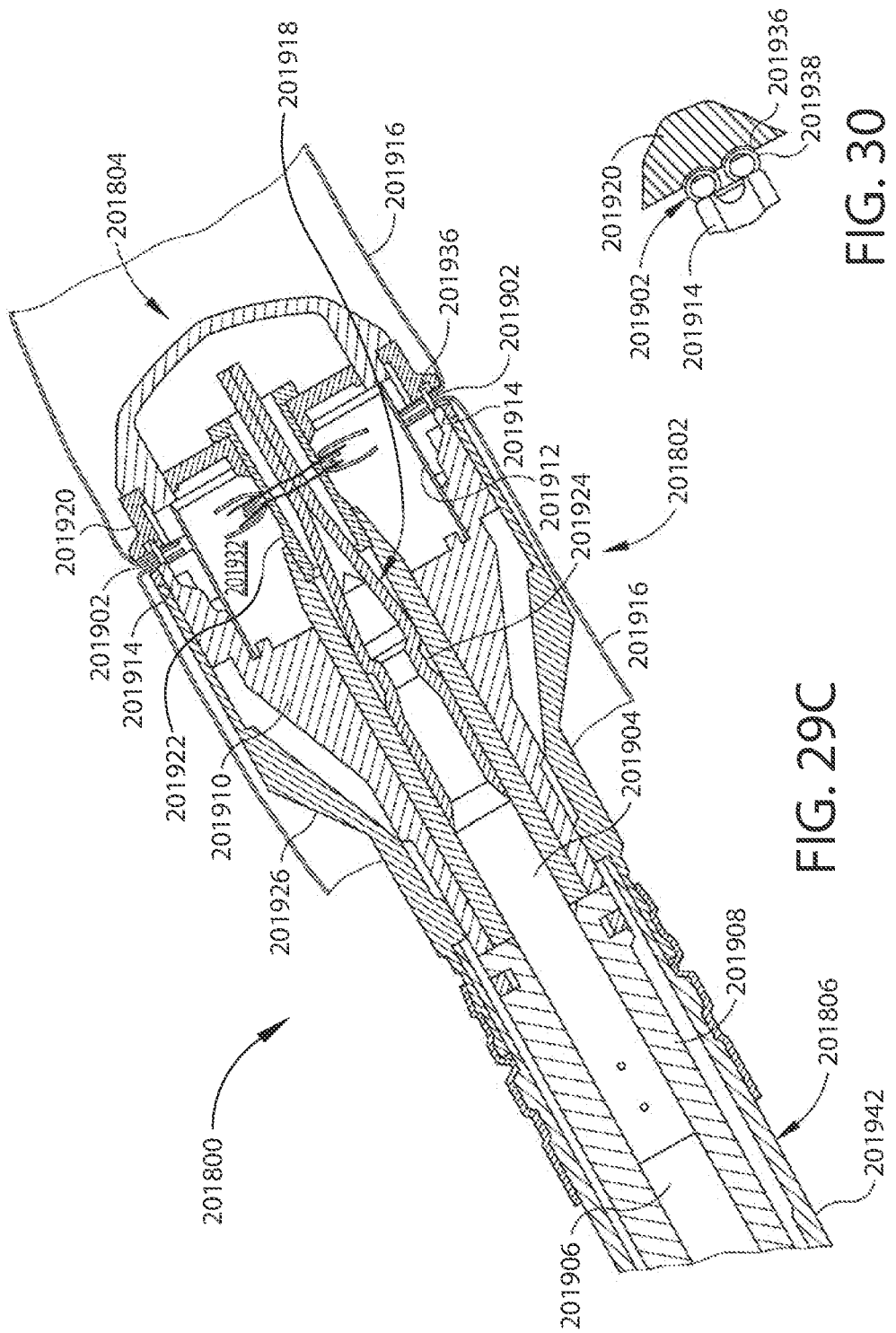

POWERED STAPLING DEVICE CONFIGURED TO ADJUST FORCE, ADVANCEMENT SPEED, AND OVERALL STROKE OF CUTTING MEMBER BASED ON SENSED PARAMETER OF FIRING OR CLAMPING

CROSS REFERENCE TO RELATED APPLICATIONS

This application is a divisional application claiming priority under 35 U.S.C. § 121 to U.S. patent application Ser. No. 16/182,240, entitled POWERED STAPLING DEVICE CONFIGURED TO ADJUST FORCE, ADVANCEMENT SPEED, AND OVERALL STROKE OF CUTTING MEMBER BASED ON SENSED PARAMETER OF FIRING OR CLAMPING, filed Nov. 6, 2018, now U.S. Patent Application Publication No. 2019/0201034 which claims priority under 35 U.S.C. § 119(e) to U.S. Provisional Patent Application No. 62/729,185, titled POWERED STAPLING DEVICE THAT IS CAPABLE OF ADJUSTING FORCE, ADVANCEMENT SPEED, AND OVERALL STROKE OF CUTTING MEMBER OF THE DEVICE BASED ON SENSED PARAMETER OF FIRING OR CLAMPING, filed on Sep. 10, 2018, the disclosure of which is herein incorporated by reference in its entirety.

The present application also claims priority under 35 U.S.C. § 119(e) to U.S. Provisional Patent Application No. 62/659,900, titled METHOD OF HUB COMMUNICATION, filed on Apr. 19, 2018, to U.S. Provisional Patent Application No. 62/692,748, titled SMART ENERGY ARCHITECTURE, filed on Jun. 30, 2018, and to U.S. Provisional Patent Application No. 62/692,768, titled SMART ENERGY DEVICES, filed on Jun. 30, 2018, the disclosure of each of which is herein incorporated by reference in its entirety.

The present application also claims priority under 35 U.S.C. § 119(e) to U.S. Provisional Patent Application No. 62/692,747, titled SMART ACTIVATION OF AN ENERGY DEVICE BY ANOTHER DEVICE, filed on Jun. 30, 2018, the disclosure of each of which is herein incorporated by reference in its entirety.

The present application also claims priority under 35 U.S.C. § 119(e) to U.S. Provisional Patent Application No. 62/650,898 filed on Mar. 30, 2018, titled CAPACITIVE COUPLED RETURN PATH PAD WITH SEPARABLE ARRAY ELEMENTS, to U.S. Provisional Patent Application Ser. No. 62/650,887, titled SURGICAL SYSTEMS WITH OPTIMIZED SENSING CAPABILITIES, filed Mar. 30, 2018, to U.S. Provisional Patent Application Ser. No. 62/650,882, titled SMOKE EVACUATION MODULE FOR INTERACTIVE SURGICAL PLATFORM, filed Mar. 30, 2018, and to U.S. Provisional Patent Application Ser. No. 62/650,877, titled SURGICAL SMOKE EVACUATION SENSING AND CONTROLS, filed Mar. 30, 2018, the disclosure of each of which is herein incorporated by reference in its entirety.

The present application also claims priority under 35 U.S.C. § 119(e) to U.S. Provisional Patent Application Ser. No. 62/640,417, titled TEMPERATURE CONTROL IN ULTRASONIC DEVICE AND CONTROL SYSTEM THEREFOR, filed Mar. 8, 2018, and to U.S. Provisional Patent Application Ser. No. 62/640,415, titled ESTIMATING STATE OF ULTRASONIC END EFFECTOR AND CONTROL SYSTEM THEREFOR, filed Mar. 8, 2018, the disclosure of each of which is herein incorporated by reference in its entirety.

The present application also claims priority under 35 U.S.C. § 119(e) to U.S. Provisional Patent Application Ser. No. 62/611,341, titled INTERACTIVE SURGICAL PLATFORM, filed Dec. 28, 2017, to U.S. Provisional Patent Application Ser. No. 62/611,340, titled CLOUD-BASED MEDICAL ANALYTICS, filed Dec. 28, 2017, and to U.S. Provisional Patent Application Ser. No. 62/611,339, titled ROBOT ASSISTED SURGICAL PLATFORM, filed Dec. 28, 2017, the disclosure of each of which is herein incorporated by reference in its entirety.

BACKGROUND

The present disclosure relates to various surgical systems. Surgical procedures are typically performed in surgical operating theaters or rooms in a healthcare facility such as, for example, a hospital. A sterile field is typically created around the patient. The sterile field may include the scrubbed team members, who are properly attired, and all furniture and fixtures in the area. Various surgical devices and systems are utilized in performance of a surgical procedure.

SUMMARY

In one aspect, the present disclosure provides a surgical stapling instrument that includes an end effector configured to clamp a tissue; a cutting member; a motor coupled to the cutting member, the motor configured to move the cutting member between a first position and a second position; and a control circuit coupled to the motor, the control circuit configured to: sense a parameter associated with clamping of the end effector; and control the motor to adjust a torque applied to the cutting member by the motor.

In another aspect, the present disclosure provides a surgical stapling instrument that includes an end effector configured to clamp a tissue; a cutting member; a motor coupled to the cutting member, the motor configured to move the cutting member between a first position and a second position; and a control circuit coupled to the motor, the control circuit configured to: sense a parameter associated with firing of the cutting member; and control the motor to adjust a torque applied to the cutting member by the motor.

In yet another aspect, the present disclosure provides a powered stapling device that includes a circular stapling head assembly; an anvil; a trocar coupled to the anvil and coupled to motor, wherein the motor in configured to advance and retract the trocar; and a control circuit coupled to the motor, wherein the control circuit is configured to: determine a position of the trocar in one of a plurality of zones; and set an anvil closure rate based on the determined position of the trocar.

FIGURES

The various aspects described herein, both as to organization and methods of operation, together with further objects and advantages thereof, may best be understood by reference to the following description, taken in conjunction with the accompanying drawings as follows.

FIG. 26 depicts a cross sectional view of the handle assembly of the instrument of FIG. 24, in accordance with at least one aspect of the present disclosure.

FIG. 27 depicts an enlarged, partial cross sectional view of the motor and battery assemblies of FIG. 24, in accordance with at least one aspect of the present disclosure.

FIG. 29C depicts an enlarged longitudinal cross-sectional view of the stapling head assembly of FIG. 29A showing a staple driver and blade in a fired position, in accordance with at least one aspect of the present disclosure.

FIG. 30 depicts an enlarged partial cross-sectional view of a staple formed against the anvil, in accordance with at least one aspect of the present disclosure.

DESCRIPTION

Figure 1:
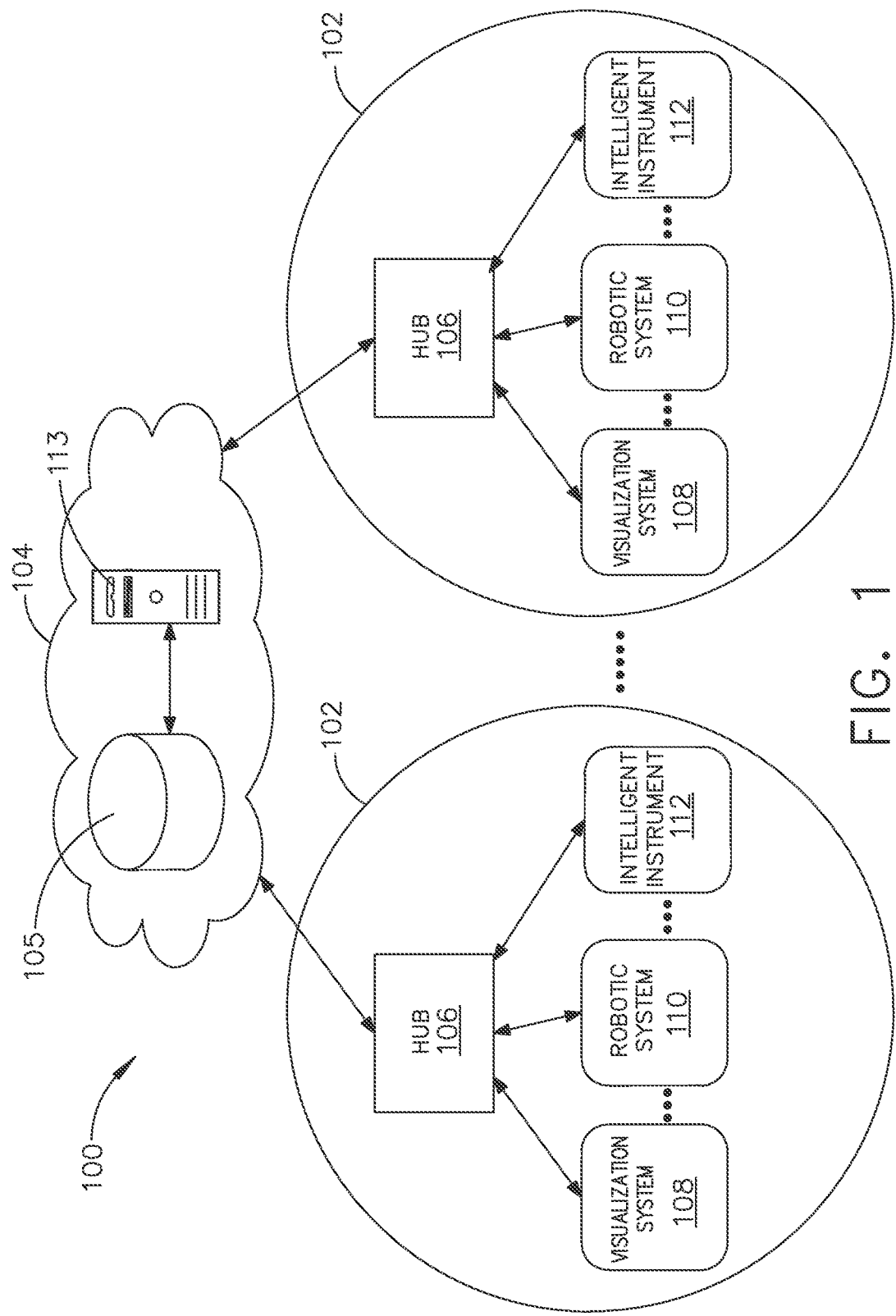
FIG. 1 is a block diagram of a computer-implemented interactive surgical system, in accordance with at least one aspect of the present disclosure.

Applicant of the present application owns the following U.S. patent applications, filed on Nov. 6, 2018, the disclosure of each of which is herein incorporated by reference in its entirety:

U.S. patent application Ser. No. 16/182,224, titled SURGICAL NETWORK, INSTRUMENT, AND CLOUD RESPONSES BASED ON VALIDATION OF RECEIVED DATASET AND AUTHENTICATION OF ITS SOURCE AND INTEGRITY, now U.S. Pat. No. 11,308,075;

U.S. patent application Ser. No. 16/182,230, titled SURGICAL SYSTEM FOR PRESENTING INFORMATION INTERPRETED FROM EXTERNAL DATA, now U.S. Patent Application Publication No. 2019/0200980;

U.S. patent application Ser. No. 16/182,233, titled MODIFICATION OF SURGICAL SYSTEMS CONTROL PROGRAMS BASED ON MACHINE LEARNING, now U.S. Pat. No. 11,832,899;

U.S. patent application Ser. No. 16/182,239, titled ADJUSTMENT OF DEVICE CONTROL PROGRAMS BASED ON STRATIFIED CONTEXTUAL DATA IN ADDITION TO THE DATA, now U.S. Pat. No. 11,423,007;

U.S. patent application Ser. No. 16/182,243, titled SURGICAL HUB AND MODULAR DEVICE RESPONSE ADJUSTMENT BASED ON SITUATIONAL AWARENESS, now U.S. Pat. No. 11,273,001;

U.S. patent application Ser. No. 16/182,248, titled DETECTION AND ESCALATION OF SECURITY RESPONSES OF SURGICAL INSTRUMENTS TO INCREASING SEVERITY THREATS, now U.S. Pat. No. 10,943,454;

U.S. patent application Ser. No. 16/182,251, titled INTERACTIVE SURGICAL SYSTEM, now U.S. Pat. No. 11,278,281;

U.S. patent application Ser. No. 16/182,260, titled AUTOMATED DATA SCALING, ALIGNMENT, AND ORGANIZING BASED ON PREDEFINED PARAMETERS WITHIN SURGICAL NETWORKS, now U.S. Pat. No. 11,056,244;

U.S. patent application Ser. No. 16/182,267, titled SENSING THE PATIENT POSITION AND CONTACT UTILIZING THE MONO-POLAR RETURN PAD ELECTRODE TO PROVIDE SITUATIONAL AWARENESS TO A SURGICAL NETWORK, now U.S. Patent Application Publication No. 2019/0201128;

U.S. patent application Ser. No. 16/182,249, titled POWERED SURGICAL TOOL WITH PREDEFINED ADJUSTABLE CONTROL ALGORITHM FOR CONTROLLING END EFFECTOR PARAMETER, now U.S. Pat. No. 11,234,756;

U.S. patent application Ser. No. 16/182,246, titled ADJUSTMENTS BASED ON AIRBORNE PARTICLE PROPERTIES, now U.S. Pat. No. 11,844,579;

U.S. patent application Ser. No. 16/182,256, titled ADJUSTMENT OF A SURGICAL DEVICE FUNCTION BASED ON SITUATIONAL AWARENESS, now U.S. Pat. No. 11,612,444;

U.S. patent application Ser. No. 16/182,242, titled REAL-TIME ANALYSIS OF COMPREHENSIVE COST OF ALL INSTRUMENTATION USED IN SURGERY UTILIZING DATA FLUIDITY TO TRACK INSTRUMENTS THROUGH STOCKING AND IN-HOUSE PROCESSES, now U.S. Pat. No. 11,257,589;

U.S. patent application Ser. No. 16/182,255, titled USAGE AND TECHNIQUE ANALYSIS OF SURGEON/STAFF PERFORMANCE AGAINST A BASELINE TO OPTIMIZE DEVICE UTILIZATION AND PERFORMANCE FOR BOTH CURRENT AND FUTURE PROCEDURES, now U.S. Pat. No. 11,633,237;

U.S. patent application Ser. No. 16/182,269, titled IMAGE CAPTURING OF THE AREAS OUTSIDE THE ABDOMEN TO IMPROVE PLACEMENT AND CONTROL OF A SURGICAL DEVICE IN USE, now U.S. Pat. No. 11,304,763;

U.S. patent application Ser. No. 16/182,278, titled COMMUNICATION OF DATA WHERE A SURGICAL NETWORK IS USING CONTEXT OF THE DATA AND REQUIREMENTS OF A RECEIVING SYSTEM/USER TO INFLUENCE INCLUSION OR LINKAGE OF DATA AND METADATA TO ESTABLISH CONTINUITY, now U.S. Patent Application Publication No. 2019/0201130;

U.S. patent application Ser. No. 16/182,290, titled SURGICAL NETWORK RECOMMENDATIONS FROM REAL TIME ANALYSIS OF PROCEDURE VARIABLES AGAINST A BASELINE HIGHLIGHTING DIFFERENCES FROM THE OPTIMAL SOLUTION, now U.S. Patent Application Publication No. 2019/0201102;

U.S. patent application Ser. No. 16/182,232, titled CONTROL OF A SURGICAL SYSTEM THROUGH A SURGICAL BARRIER, now U.S. Patent Application Publication No. 2019/0201158;

U.S. patent application Ser. No. 16/182,227, titled SURGICAL NETWORK DETERMINATION OF PRIORITIZATION OF COMMUNICATION, INTERACTION, OR PROCESSING BASED ON SYSTEM OR DEVICE NEEDS, now U.S. Pat. No. 10,892,995;

U.S. patent application Ser. No. 16/182,231, titled WIRELESS PAIRING OF A SURGICAL DEVICE WITH ANOTHER DEVICE WITHIN A STERILE SURGICAL FIELD BASED ON THE USAGE AND SITUATIONAL AWARENESS OF DEVICES, now U.S. Pat. No. 10,758,310;

U.S. patent application Ser. No. 16/182,229, titled ADJUSTMENT OF STAPLE HEIGHT OF AT LEAST ONE ROW OF STAPLES BASED ON THE SENSED TISSUE THICKNESS OR FORCE IN CLOSING, now U.S. Pat. No. 11,096,693;

U.S. patent application Ser. No. 16/182,234, titled STAPLING DEVICE WITH BOTH COMPULSORY AND DISCRETIONARY LOCKOUTS BASED ON SENSED PARAMETERS, now U.S. Patent Application Publication No. 2019/0200997;

U.S. patent application Ser. No. 16/182,235, titled VARIATION OF RADIO FREQUENCY AND ULTRASONIC POWER LEVEL IN COOPERATION WITH VARYING CLAMP ARM PRESSURE TO ACHIEVE PREDEFINED HEAT FLUX OR POWER APPLIED TO TISSUE, now U.S. Pat. No. 11,446,052; and U.S. patent application Ser. No. 16/182,238, titled ULTRASONIC ENERGY DEVICE WHICH VARIES PRESSURE APPLIED BY CLAMP ARM TO PROVIDE THRESHOLD CONTROL PRESSURE AT A CUT PROGRESSION LOCATION, now U.S. Pat. No. 11,419,667.

Applicant of the present application owns the following U.S. patent applications, filed on Sep. 10, 2018, the disclosure of each of which is herein incorporated by reference in its entirety:

U.S. Provisional Patent Application No. 62/729,183, titled A CONTROL FOR A SURGICAL NETWORK OR SURGICAL NETWORK CONNECTED DEVICE THAT ADJUSTS ITS FUNCTION BASED ON A SENSED SITUATION OR USAGE;

U.S. Provisional Patent Application No. 62/729,177, titled AUTOMATED DATA SCALING, ALIGNMENT, AND ORGANIZING BASED ON PREDEFINED PARAMETERS WITHIN A SURGICAL NETWORK BEFORE TRANSMISSION;

U.S. Provisional Patent Application No. 62/729,176, titled INDIRECT COMMAND AND CONTROL OF A FIRST OPERATING ROOM SYSTEM THROUGH THE USE OF A SECOND OPERATING ROOM SYSTEM WITHIN A STERILE FIELD WHERE THE SECOND OPERATING ROOM SYSTEM HAS PRIMARY AND SECONDARY OPERATING MODES;

U.S. Provisional Patent Application No. 62/729,185, titled POWERED STAPLING DEVICE THAT IS CAPABLE OF ADJUSTING FORCE, ADVANCEMENT SPEED, AND OVERALL STROKE OF CUTTING MEMBER OF THE DEVICE BASED ON SENSED PARAMETER OF FIRING OR CLAMPING;

U.S. Provisional Patent Application No. 62/729,184, titled POWERED SURGICAL TOOL WITH A PREDEFINED ADJUSTABLE CONTROL ALGORITHM FOR CONTROLLING AT LEAST ONE END EFFECTOR PARAMETER AND A MEANS FOR LIMITING THE ADJUSTMENT;

U.S. Provisional Patent Application No. 62/729,182, titled SENSING THE PATIENT POSITION AND CONTACT UTILIZING THE MONO POLAR RETURN PAD ELECTRODE TO PROVIDE SITUATIONAL AWARENESS TO THE HUB;

U.S. Provisional Patent Application No. 62/729,191, titled SURGICAL NETWORK RECOMMENDATIONS FROM REAL TIME ANALYSIS OF PROCEDURE VARIABLES AGAINST A BASELINE HIGHLIGHTING DIFFERENCES FROM THE OPTIMAL SOLUTION;

U.S. Provisional Patent Application No. 62/729,195, titled ULTRASONIC ENERGY DEVICE WHICH VARIES PRESSURE APPLIED BY CLAMP ARM TO PROVIDE THRESHOLD CONTROL PRESSURE AT A CUT PROGRESSION LOCATION; and U.S. Provisional Patent Application No. 62/729,186, titled WIRELESS PAIRING OF A SURGICAL DEVICE WITH ANOTHER DEVICE WITHIN A STERILE SURGICAL FIELD BASED ON THE USAGE AND SITUATIONAL AWARENESS OF DEVICES.

Applicant of the present application owns the following U.S. patent applications, filed on Aug. 28, 2018, the disclosure of each of which is herein incorporated by reference in its entirety:

U.S. patent application Ser. No. 16/115,214, titled ESTIMATING STATE OF ULTRASONIC END EFFECTOR AND CONTROL SYSTEM THEREFOR;

U.S. patent application Ser. No. 16/115,205, titled TEMPERATURE CONTROL OF ULTRASONIC END EFFECTOR AND CONTROL SYSTEM THEREFOR;

U.S. patent application Ser. No. 16/115,233, titled RADIO FREQUENCY ENERGY DEVICE FOR DELIVERING COMBINED ELECTRICAL SIGNALS;

U.S. patent application Ser. No. 16/115,208, titled CONTROLLING AN ULTRASONIC SURGICAL INSTRUMENT ACCORDING TO TISSUE LOCATION;

U.S. patent application Ser. No. 16/115,220, titled CONTROLLING ACTIVATION OF AN ULTRASONIC SURGICAL INSTRUMENT ACCORDING TO THE PRESENCE OF TISSUE;

U.S. patent application Ser. No. 16/115,232, titled DETERMINING TISSUE COMPOSITION VIA AN ULTRASONIC SYSTEM;

U.S. patent application Ser. No. 16/115,239, titled DETERMINING THE STATE OF AN ULTRASONIC ELECTROMECHANICAL SYSTEM ACCORDING TO FREQUENCY SHIFT;

U.S. patent application Ser. No. 16/115,247, titled DETERMINING THE STATE OF AN ULTRASONIC END EFFECTOR;

U.S. patent application Ser. No. 16/115,211, titled SITUATIONAL AWARENESS OF ELECTROSURGICAL SYSTEMS;

U.S. patent application Ser. No. 16/115,226, titled MECHANISMS FOR CONTROLLING DIFFERENT ELECTROMECHANICAL SYSTEMS OF AN ELECTROSURGICAL INSTRUMENT;

U.S. patent application Ser. No. 16/115,240, titled DETECTION OF END EFFECTOR IMMERSION IN LIQUID;

U.S. patent application Ser. No. 16/115,249, titled INTERRUPTION OF ENERGY DUE TO INADVERTENT CAPACITIVE COUPLING;

U.S. patent application Ser. No. 16/115,256, titled INCREASING RADIO FREQUENCY TO CREATE PAD-LESS MONOPOLAR LOOP;

U.S. patent application Ser. No. 16/115,223, titled BIPOLAR COMBINATION DEVICE THAT AUTOMATICALLY ADJUSTS PRESSURE BASED ON ENERGY MODALITY; and U.S. patent application Ser. No. 16/115,238, titled ACTIVATION OF ENERGY DEVICES.

Applicant of the present application owns the following U.S. patent applications, filed on Aug. 23, 2018, the disclosure of each of which is herein incorporated by reference in its entirety:

U.S. Provisional Patent Application No. 62/721,995, titled CONTROLLING AN ULTRASONIC SURGICAL INSTRUMENT ACCORDING TO TISSUE LOCATION;

U.S. Provisional Patent Application No. 62/721,998, titled SITUATIONAL AWARENESS OF ELECTROSURGICAL SYSTEMS;

U.S. Provisional Patent Application No. 62/721,999, titled INTERRUPTION OF ENERGY DUE TO INADVERTENT CAPACITIVE COUPLING;

U.S. Provisional Patent Application No. 62/721,994, titled BIPOLAR COMBINATION DEVICE THAT AUTOMATICALLY ADJUSTS PRESSURE BASED ON ENERGY MODALITY; and U.S. Provisional Patent Application No. 62/721,996, titled RADIO FREQUENCY ENERGY DEVICE FOR DELIVERING COMBINED ELECTRICAL SIGNALS.

Applicant of the present application owns the following U.S. patent applications, filed on Jun. 30, 2018, the disclosure of each of which is herein incorporated by reference in its entirety:

U.S. Provisional Patent Application No. 62/692,747, titled SMART ACTIVATION OF AN ENERGY DEVICE BY ANOTHER DEVICE;

U.S. Provisional Patent Application No. 62/692,748, titled SMART ENERGY ARCHITECTURE; and U.S. Provisional Patent Application No. 62/692,768, titled SMART ENERGY DEVICES.

Applicant of the present application owns the following U.S. patent applications, filed on Jun. 29, 2018, the disclosure of each of which is herein incorporated by reference in its entirety:

U.S. patent application Ser. No. 16/024,090, titled CAPACITIVE COUPLED RETURN PATH PAD WITH SEPARABLE ARRAY ELEMENTS;

U.S. patent application Ser. No. 16/024,057, titled CONTROLLING A SURGICAL INSTRUMENT ACCORDING TO SENSED CLOSURE PARAMETERS;

U.S. patent application Ser. No. 16/024,067, titled SYSTEMS FOR ADJUSTING END EFFECTOR PARAMETERS BASED ON PERIOPERATIVE INFORMATION;

U.S. patent application Ser. No. 16/024,075, titled SAFETY SYSTEMS FOR SMART POWERED SURGICAL STAPLING;

U.S. patent application Ser. No. 16/024,083, titled SAFETY SYSTEMS FOR SMART POWERED SURGICAL STAPLING;

U.S. patent application Ser. No. 16/024,094, titled SURGICAL SYSTEMS FOR DETECTING END EFFECTOR TISSUE DISTRIBUTION IRREGULARITIES;

U.S. patent application Ser. No. 16/024,138, titled SYSTEMS FOR DETECTING PROXIMITY OF SURGICAL END EFFECTOR TO CANCEROUS TISSUE;

U.S. patent application Ser. No. 16/024,150, titled SURGICAL INSTRUMENT CARTRIDGE SENSOR ASSEMBLIES;

U.S. patent application Ser. No. 16/024,160, titled VARIABLE OUTPUT CARTRIDGE SENSOR ASSEMBLY;

U.S. patent application Ser. No. 16/024,124, titled SURGICAL INSTRUMENT HAVING A FLEXIBLE ELECTRODE;

U.S. patent application Ser. No. 16/024,132, titled SURGICAL INSTRUMENT HAVING A FLEXIBLE CIRCUIT;

U.S. patent application Ser. No. 16/024,141, titled SURGICAL INSTRUMENT WITH A TISSUE MARKING ASSEMBLY;

U.S. patent application Ser. No. 16/024,162, titled SURGICAL SYSTEMS WITH PRIORITIZED DATA TRANSMISSION CAPABILITIES;

U.S. patent application Ser. No. 16/024,066, titled SURGICAL EVACUATION SENSING AND MOTOR CONTROL;

U.S. patent application Ser. No. 16/024,096, titled SURGICAL EVACUATION SENSOR ARRANGEMENTS;

U.S. patent application Ser. No. 16/024,116, titled SURGICAL EVACUATION FLOW PATHS;

U.S. patent application Ser. No. 16/024,149, titled SURGICAL EVACUATION SENSING AND GENERATOR CONTROL;

U.S. patent application Ser. No. 16/024,180, titled SURGICAL EVACUATION SENSING AND DISPLAY;

U.S. patent application Ser. No. 16/024,245, titled COMMUNICATION OF SMOKE EVACUATION SYSTEM PARAMETERS TO HUB OR CLOUD IN SMOKE EVACUATION MODULE FOR INTERACTIVE SURGICAL PLATFORM;

U.S. patent application Ser. No. 16/024,258, titled SMOKE EVACUATION SYSTEM INCLUDING A SEGMENTED CONTROL CIRCUIT FOR INTERACTIVE SURGICAL PLATFORM;

U.S. patent application Ser. No. 16/024,265, titled SURGICAL EVACUATION SYSTEM WITH A COMMUNICATION CIRCUIT FOR COMMUNICATION BETWEEN A FILTER AND A SMOKE EVACUATION DEVICE; and U.S. patent application Ser. No. 16/024,273, titled DUAL IN-SERIES LARGE AND SMALL DROPLET FILTERS.

Applicant of the present application owns the following U.S. Provisional Patent Applications, filed on Jun. 28, 2018, the disclosure of each of which is herein incorporated by reference in its entirety:

U.S. Provisional Patent Application Ser. No. 62/691,228, titled A METHOD OF USING REINFORCED FLEX CIRCUITS WITH MULTIPLE SENSORS WITH ELECTROSURGICAL DEVICES;

U.S. Provisional Patent Application Ser. No. 62/691,227, titled CONTROLLING A SURGICAL INSTRUMENT ACCORDING TO SENSED CLOSURE PARAMETERS;

U.S. Provisional Patent Application Ser. No. 62/691,230, titled SURGICAL INSTRUMENT HAVING A FLEXIBLE ELECTRODE;

U.S. Provisional Patent Application Ser. No. 62/691,219, titled SURGICAL EVACUATION SENSING AND MOTOR CONTROL;

U.S. Provisional Patent Application Ser. No. 62/691,257, titled COMMUNICATION OF SMOKE EVACUATION SYSTEM PARAMETERS TO HUB OR CLOUD IN SMOKE EVACUATION MODULE FOR INTERACTIVE SURGICAL PLATFORM;

U.S. Provisional Patent Application Ser. No. 62/691,262, titled SURGICAL EVACUATION SYSTEM WITH A COMMUNICATION CIRCUIT FOR COMMUNICATION BETWEEN A FILTER AND A SMOKE EVACUATION DEVICE; and U.S. Provisional Patent Application Ser. No. 62/691,251, titled DUAL IN-SERIES LARGE AND SMALL DROPLET FILTERS.

Applicant of the present application owns the following U.S. Provisional Patent Application, filed on Apr. 19, 2018, the disclosure of which is herein incorporated by reference in its entirety:

U.S. Provisional Patent Application Ser. No. 62/659,900, titled METHOD OF HUB COMMUNICATION.

Applicant of the present application owns the following U.S. Provisional Patent Applications, filed on Mar. 30, 2018, the disclosure of each of which is herein incorporated by reference in its entirety:

U.S. Provisional Patent Application No. 62/650,898 filed on Mar. 30, 2018, titled CAPACITIVE COUPLED RETURN PATH PAD WITH SEPARABLE ARRAY ELEMENTS;

U.S. Provisional Patent Application Ser. No. 62/650,887, titled SURGICAL SYSTEMS WITH OPTIMIZED SENSING CAPABILITIES;

U.S. Provisional Patent Application Ser. No. 62/650,882, titled SMOKE EVACUATION MODULE FOR INTERACTIVE SURGICAL PLATFORM; and U.S. Provisional Patent Application Ser. No. 62/650,877, titled SURGICAL SMOKE EVACUATION SENSING AND CONTROLS.

Applicant of the present application owns the following U.S. patent applications, filed on Mar. 29, 2018, the disclosure of each of which is herein incorporated by reference in its entirety:

U.S. patent application Ser. No. 15/940,641, titled INTERACTIVE SURGICAL SYSTEMS WITH ENCRYPTED COMMUNICATION CAPABILITIES;

U.S. patent application Ser. No. 15/940,648, titled INTERACTIVE SURGICAL SYSTEMS WITH CONDITION HANDLING OF DEVICES AND DATA CAPABILITIES;

U.S. patent application Ser. No. 15/940,656, titled SURGICAL HUB COORDINATION OF CONTROL AND COMMUNICATION OF OPERATING ROOM DEVICES;

U.S. patent application Ser. No. 15/940,666, titled SPATIAL AWARENESS OF SURGICAL HUBS IN OPERATING ROOMS;

U.S. patent application Ser. No. 15/940,670, titled COOPERATIVE UTILIZATION OF DATA DERIVED FROM SECONDARY SOURCES BY INTELLIGENT SURGICAL HUBS;

U.S. patent application Ser. No. 15/940,677, titled SURGICAL HUB CONTROL ARRANGEMENTS;

U.S. patent application Ser. No. 15/940,632, titled DATA STRIPPING METHOD TO INTERROGATE PATIENT RECORDS AND CREATE ANONYMIZED RECORD;

U.S. patent application Ser. No. 15/940,640, titled COMMUNICATION HUB AND STORAGE DEVICE FOR STORING PARAMETERS AND STATUS OF A SURGICAL DEVICE TO BE SHARED WITH CLOUD BASED ANALYTICS SYSTEMS;

U.S. patent application Ser. No. 15/940,645, titled SELF DESCRIBING DATA PACKETS GENERATED AT AN ISSUING INSTRUMENT;

U.S. patent application Ser. No. 15/940,649, titled DATA PAIRING TO INTERCONNECT A DEVICE MEASURED PARAMETER WITH AN OUTCOME;

U.S. patent application Ser. No. 15/940,654, titled SURGICAL HUB SITUATIONAL AWARENESS;

U.S. patent application Ser. No. 15/940,663, titled SURGICAL SYSTEM DISTRIBUTED PROCESSING;

U.S. patent application Ser. No. 15/940,668, titled AGGREGATION AND REPORTING OF SURGICAL HUB DATA;

U.S. patent application Ser. No. 15/940,671, titled SURGICAL HUB SPATIAL AWARENESS TO DETERMINE DEVICES IN OPERATING THEATER;

U.S. patent application Ser. No. 15/940,686, titled DISPLAY OF ALIGNMENT OF STAPLE CARTRIDGE TO PRIOR LINEAR STAPLE LINE;

U.S. patent application Ser. No. 15/940,700, titled STERILE FIELD INTERACTIVE CONTROL DISPLAYS;

U.S. patent application Ser. No. 15/940,629, titled COMPUTER IMPLEMENTED INTERACTIVE SURGICAL SYSTEMS;

U.S. patent application Ser. No. 15/940,704, titled USE OF LASER LIGHT AND RED-GREEN-BLUE COLORATION TO DETERMINE PROPERTIES OF BACK SCATTERED LIGHT;

U.S. patent application Ser. No. 15/940,722, titled CHARACTERIZATION OF TISSUE IRREGULARITIES THROUGH THE USE OF MONO-CHROMATIC LIGHT REFRACTIVITY;

U.S. patent application Ser. No. 15/940,742, titled DUAL CMOS ARRAY IMAGING;

U.S. patent application Ser. No. 15/940,636, titled ADAPTIVE CONTROL PROGRAM UPDATES FOR SURGICAL DEVICES;

U.S. patent application Ser. No. 15/940,653, titled ADAPTIVE CONTROL PROGRAM UPDATES FOR SURGICAL HUBS;

U.S. patent application Ser. No. 15/940,660, titled CLOUD-BASED MEDICAL ANALYTICS FOR CUSTOMIZATION AND RECOMMENDATIONS TO A USER;

U.S. patent application Ser. No. 15/940,679, titled CLOUD-BASED MEDICAL ANALYTICS FOR LINKING OF LOCAL USAGE TRENDS WITH THE RESOURCE ACQUISITION BEHAVIORS OF LARGER DATA SET;

U.S. patent application Ser. No. 15/940,694, titled CLOUD-BASED MEDICAL ANALYTICS FOR MEDICAL FACILITY SEGMENTED INDIVIDUALIZATION OF INSTRUMENT FUNCTION;

U.S. patent application Ser. No. 15/940,634, titled CLOUD-BASED MEDICAL ANALYTICS FOR SECURITY AND AUTHENTICATION TRENDS AND REACTIVE MEASURES;

U.S. patent application Ser. No. 15/940,706, titled DATA HANDLING AND PRIORITIZATION IN A CLOUD ANALYTICS NETWORK;

U.S. patent application Ser. No. 15/940,675, titled CLOUD INTERFACE FOR COUPLED SURGICAL DEVICES;

U.S. patent application Ser. No. 15/940,627, titled DRIVE ARRANGEMENTS FOR ROBOT-ASSISTED SURGICAL PLATFORMS;

U.S. patent application Ser. No. 15/940,637, titled COMMUNICATION ARRANGEMENTS FOR ROBOT-ASSISTED SURGICAL PLATFORMS;

U.S. patent application Ser. No. 15/940,642, titled CONTROLS FOR ROBOT-ASSISTED SURGICAL PLATFORMS;

U.S. patent application Ser. No. 15/940,676, titled AUTOMATIC TOOL ADJUSTMENTS FOR ROBOT-ASSISTED SURGICAL PLATFORMS;

U.S. patent application Ser. No. 15/940,680, titled CONTROLLERS FOR ROBOT-ASSISTED SURGICAL PLATFORMS;

U.S. patent application Ser. No. 15/940,683, titled COOPERATIVE SURGICAL ACTIONS FOR ROBOT-ASSISTED SURGICAL PLATFORMS;

U.S. patent application Ser. No. 15/940,690, titled DISPLAY ARRANGEMENTS FOR ROBOT-ASSISTED SURGICAL PLATFORMS; and U.S. patent application Ser. No. 15/940,711, titled SENSING ARRANGEMENTS FOR ROBOT-ASSISTED SURGICAL PLATFORMS.

Applicant of the present application owns the following U.S. Provisional Patent Applications, filed on Mar. 28, 2018, the disclosure of each of which is herein incorporated by reference in its entirety:

U.S. Provisional Patent Application Ser. No. 62/649,302, titled INTERACTIVE SURGICAL SYSTEMS WITH ENCRYPTED COMMUNICATION CAPABILITIES;

U.S. Provisional Patent Application Ser. No. 62/649,294, titled DATA STRIPPING METHOD TO INTERROGATE PATIENT RECORDS AND CREATE ANONYMIZED RECORD;

U.S. Provisional Patent Application Ser. No. 62/649,300, titled SURGICAL HUB SITUATIONAL AWARENESS;

U.S. Provisional Patent Application Ser. No. 62/649,309, titled SURGICAL HUB SPATIAL AWARENESS TO DETERMINE DEVICES IN OPERATING THEATER;

U.S. Provisional Patent Application Ser. No. 62/649,310, titled COMPUTER IMPLEMENTED INTERACTIVE SURGICAL SYSTEMS;

U.S. Provisional Patent Application Ser. No. 62/649,291, titled USE OF LASER LIGHT AND RED-GREEN-BLUE COLORATION TO DETERMINE PROPERTIES OF BACK SCATTERED LIGHT;

U.S. Provisional Patent Application Ser. No. 62/649,296, titled ADAPTIVE CONTROL PROGRAM UPDATES FOR SURGICAL DEVICES;

U.S. Provisional Patent Application Ser. No. 62/649,333, titled CLOUD-BASED MEDICAL ANALYTICS FOR CUSTOMIZATION AND RECOMMENDATIONS TO A USER;

U.S. Provisional Patent Application Ser. No. 62/649,327, titled CLOUD-BASED MEDICAL ANALYTICS FOR SECURITY AND AUTHENTICATION TRENDS AND REACTIVE MEASURES;

U.S. Provisional Patent Application Ser. No. 62/649,315, titled DATA HANDLING AND PRIORITIZATION IN A CLOUD ANALYTICS NETWORK;

U.S. Provisional Patent Application Ser. No. 62/649,313, titled CLOUD INTERFACE FOR COUPLED SURGICAL DEVICES;

U.S. Provisional Patent Application Ser. No. 62/649,320, titled DRIVE ARRANGEMENTS FOR ROBOT-ASSISTED SURGICAL PLATFORMS;

U.S. Provisional Patent Application Ser. No. 62/649,307, titled AUTOMATIC TOOL ADJUSTMENTS FOR ROBOT-ASSISTED SURGICAL PLATFORMS; and U.S. Provisional Patent Application Ser. No. 62/649,323, titled SENSING ARRANGEMENTS FOR ROBOT-ASSISTED SURGICAL PLATFORMS.

Applicant of the present application owns the following U.S. Provisional Patent Applications, filed on Mar. 8, 2018, the disclosure of each of which is herein incorporated by reference in its entirety:

U.S. Provisional Patent Application Ser. No. 62/640,417, titled TEMPERATURE CONTROL IN ULTRASONIC DEVICE AND CONTROL SYSTEM THEREFOR; and U.S. Provisional Patent Application Ser. No. 62/640,415, titled ESTIMATING STATE OF ULTRASONIC END EFFECTOR AND CONTROL SYSTEM THEREFOR.

Applicant of the present application owns the following U.S. Provisional Patent Applications, filed on Dec. 28, 2017, the disclosure of each of which is herein incorporated by reference in its entirety:

U.S. Provisional Patent Application Serial No. U.S. Provisional Patent Application Ser. No. 62/611,341, titled INTERACTIVE SURGICAL PLATFORM;

U.S. Provisional Patent Application Ser. No. 62/611,340, titled CLOUD-BASED MEDICAL ANALYTICS; and U.S. Provisional Patent Application Ser. No. 62/611,339, titled ROBOT ASSISTED SURGICAL PLATFORM.

Before explaining various aspects of surgical devices and generators in detail, it should be noted that the illustrative examples are not limited in application or use to the details of construction and arrangement of parts illustrated in the accompanying drawings and description. The illustrative examples may be implemented or incorporated in other aspects, variations and modifications, and may be practiced or carried out in various ways. Further, unless otherwise indicated, the terms and expressions employed herein have been chosen for the purpose of describing the illustrative examples for the convenience of the reader and are not for the purpose of limitation thereof. Also, it will be appreciated that one or more of the following-described aspects, expressions of aspects, and/or examples, can be combined with any one or more of the other following-described aspects, expressions of aspects and/or examples.

Surgical Hubs

Referring to FIG. 1, a computer-implemented interactive surgical system 100 includes one or more surgical systems 102 and a cloud-based system (e.g., the cloud 104 that may include a remote server 113 coupled to a storage device 105). Each surgical system 102 includes at least one surgical hub 106 in communication with the cloud 104 that may include a remote server 113. In one example, as illustrated in FIG. 1, the surgical system 102 includes a visualization system 108, a robotic system 110, and a handheld intelligent surgical instrument 112, which are configured to communicate with one another and/or the hub 106. In some aspects, a surgical system 102 may include an M number of hubs 106, an N number of visualization systems 108, an O number of robotic systems 110, and a P number of handheld intelligent surgical instruments 112, where M, N, O, and P are integers greater than or equal to one.

In various aspects, the intelligent instruments 112 as described herein with reference to FIGS. 1-7 may be implemented as a circular powered stapling device 201800 (FIGS. 24-30), 201502 (FIGS. 31-33), 201532 (FIGS. 34-35), 201610 (FIGS. 36-40). The intelligent instruments 112 (e.g., devices $1_a$-$1_n$) such as the circular powered stapling device 201800 (FIGS. 24-30), 201502 (FIGS. 31-33), 201532 (FIGS. 34-35), 201610 (FIGS. 36-40) are configured to operate in a surgical data network 201 as described with reference to FIG. 8.

Figure 2:
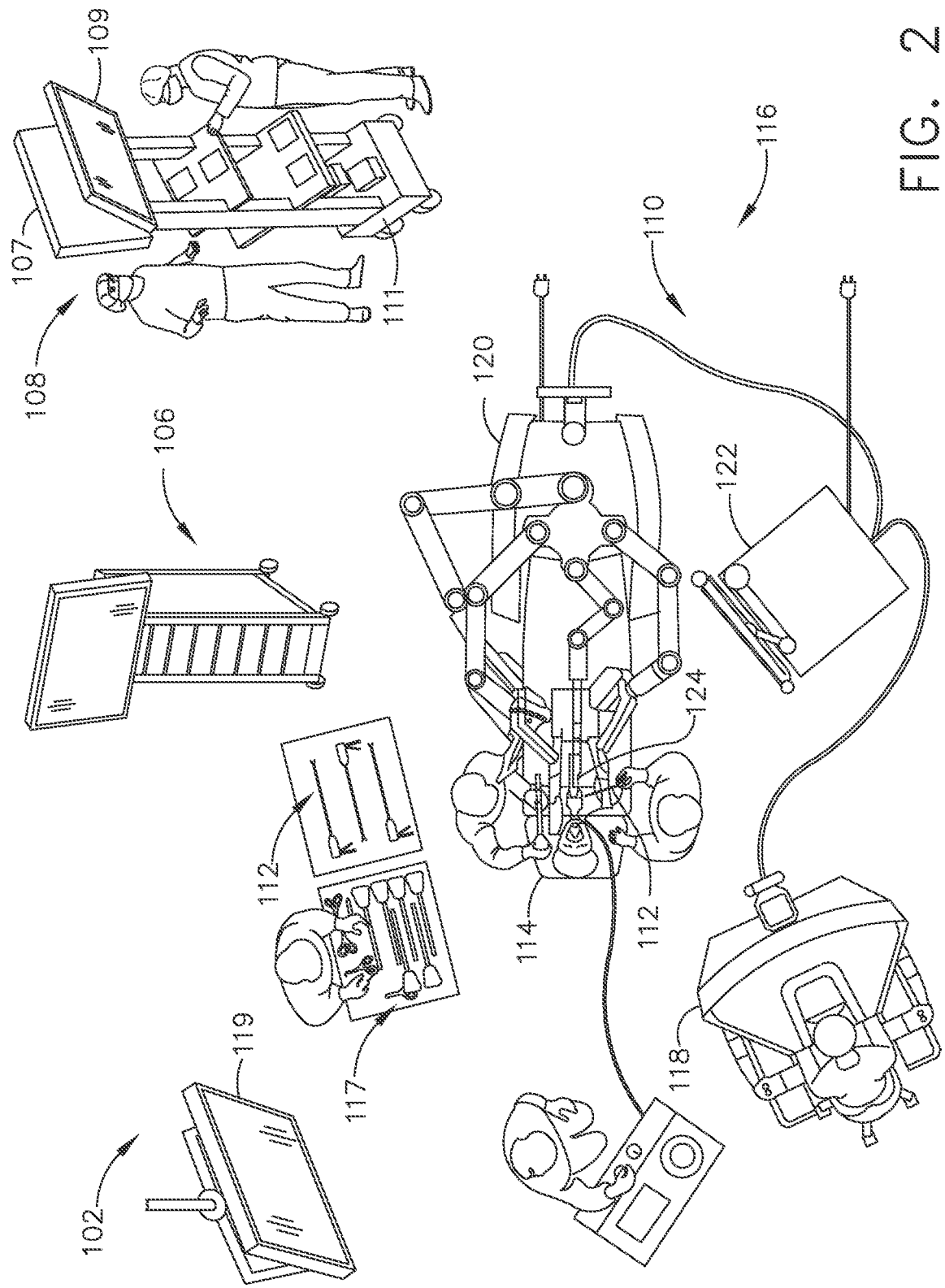
FIG. 2 is a surgical system being used to perform a surgical procedure in an operating room, in accordance with at least one aspect of the present disclosure.

FIG. 2 depicts an example of a surgical system 102 being used to perform a surgical procedure on a patient who is lying down on an operating table 114 in a surgical operating room 116. A robotic system 110 is used in the surgical procedure as a part of the surgical system 102. The robotic system 110 includes a surgeon's console 118, a patient side cart 120 (surgical robot), and a surgical robotic hub 122. The patient side cart 120 can manipulate at least one removably coupled surgical tool 117 through a minimally invasive incision in the body of the patient while the surgeon views the surgical site through the surgeon's console 118. An image of the surgical site can be obtained by a medical imaging device 124, which can be manipulated by the patient side cart 120 to orient the imaging device 124. The robotic hub 122 can be used to process the images of the surgical site for subsequent display to the surgeon through the surgeon's console 118.

Other types of robotic systems can be readily adapted for use with the surgical system 102. Various examples of robotic systems and surgical tools that are suitable for use with the present disclosure are described in U.S. Provisional Patent Application Ser. No. 62/611,339, titled ROBOT ASSISTED SURGICAL PLATFORM, filed Dec. 28, 2017, the disclosure of which is herein incorporated by reference in its entirety.

Various examples of cloud-based analytics that are performed by the cloud 104, and are suitable for use with the present disclosure, are described in U.S. Provisional Patent Application Ser. No. 62/611,340, titled CLOUD-BASED MEDICAL ANALYTICS, filed Dec. 28, 2017, the disclosure of which is herein incorporated by reference in its entirety.

In various aspects, the imaging device 124 includes at least one image sensor and one or more optical components. Suitable image sensors include, but are not limited to, Charge-Coupled Device (CCD) sensors and Complementary Metal-Oxide Semiconductor (CMOS) sensors.

The optical components of the imaging device 124 may include one or more illumination sources and/or one or more lenses. The one or more illumination sources may be directed to illuminate portions of the surgical field. The one or more image sensors may receive light reflected or refracted from the surgical field, including light reflected or refracted from tissue and/or surgical instruments.

The one or more illumination sources may be configured to radiate electromagnetic energy in the visible spectrum as well as the invisible spectrum. The visible spectrum, sometimes referred to as the optical spectrum or luminous spectrum, is that portion of the electromagnetic spectrum that is visible to (i.e., can be detected by) the human eye and may be referred to as visible light or simply light. A typical human eye will respond to wavelengths in air that are from about 380 nm to about 750 nm.

The invisible spectrum (i.e., the non-luminous spectrum) is that portion of the electromagnetic spectrum that lies below and above the visible spectrum (i.e., wavelengths below about 380 nm and above about 750 nm). The invisible spectrum is not detectable by the human eye. Wavelengths greater than about 750 nm are longer than the red visible spectrum, and they become invisible infrared (IR), microwave, and radio electromagnetic radiation. Wavelengths less than about 380 nm are shorter than the violet spectrum, and they become invisible ultraviolet, x-ray, and gamma ray electromagnetic radiation.

In various aspects, the imaging device 124 is configured for use in a minimally invasive procedure. Examples of imaging devices suitable for use with the present disclosure include, but are not limited to, an arthroscope, angioscope, bronchoscope, choledochoscope, colonoscope, cytoscope, duodenoscope, enteroscope, esophagogastro-duodenoscope (gastroscope), endoscope, laryngoscope, nasopharyngo-neproscope, sigmoidoscope, thoracoscope, and uretero-scope.

In one aspect, the imaging device employs multi-spectrum monitoring to discriminate topography and underlying structures. A multi-spectral image is one that captures image data within specific wavelength ranges across the electromagnetic spectrum. The wavelengths may be separated by filters or by the use of instruments that are sensitive to particular wavelengths, including light from frequencies beyond the visible light range, e.g., IR and ultraviolet. Spectral imaging can allow extraction of additional information the human eye fails to capture with its receptors for red, green, and blue. The use of multi-spectral imaging is described in greater detail under the heading "Advanced Imaging Acquisition Module" in U.S. Provisional Patent Application Ser. No. 62/611,341, titled INTERACTIVE SURGICAL PLATFORM, filed Dec. 28, 2017, the disclosure of which is herein incorporated by reference in its entirety. Multi-spectrum monitoring can be a useful tool in relocating a surgical field after a surgical task is completed to perform one or more of the previously described tests on the treated tissue.

It is axiomatic that strict sterilization of the operating room and surgical equipment is required during any surgery. The strict hygiene and sterilization conditions required in a "surgical theater," i.e., an operating or treatment room, necessitate the highest possible sterility of all medical devices and equipment. Part of that sterilization process is the need to sterilize anything that comes in contact with the patient or penetrates the sterile field, including the imaging device 124 and its attachments and components. It will be appreciated that the sterile field may be considered a specified area, such as within a tray or on a sterile towel, that is considered free of microorganisms, or the sterile field may be considered an area, immediately around a patient, who has been prepared for a surgical procedure. The sterile field may include the scrubbed team members, who are properly attired, and all furniture and fixtures in the area.

In various aspects, the visualization system 108 includes one or more imaging sensors, one or more image-processing units, one or more storage arrays, and one or more displays that are strategically arranged with respect to the sterile field, as illustrated in FIG. 2. In one aspect, the visualization system 108 includes an interface for HL7, PACS, and EMR. Various components of the visualization system 108 are described under the heading "Advanced Imaging Acquisition Module" in U.S. Provisional Patent Application Ser. No. 62/611,341, titled INTERACTIVE SURGICAL PLATFORM, filed Dec. 28, 2017, the disclosure of which is herein incorporated by reference in its entirety.

As illustrated in FIG. 2, a primary display 119 is positioned in the sterile field to be visible to an operator at the operating table 114. In addition, a visualization tower 111 is positioned outside the sterile field. The visualization tower 111 includes a first non-sterile display 107 and a second non-sterile display 109, which face away from each other. The visualization system 108, guided by the hub 106, is configured to utilize the displays 107, 109, and 119 to coordinate information flow to operators inside and outside the sterile field. For example, the hub 106 may cause the visualization system 108 to display a snapshot of a surgical site, as recorded by an imaging device 124, on a non-sterile display 107 or 109, while maintaining a live feed of the surgical site on the primary display 119. The snapshot on the non-sterile display 107 or 109 can permit a non-sterile operator to perform a diagnostic step relevant to the surgical procedure, for example.

In one aspect, the hub 106 is also configured to route a diagnostic input or feedback entered by a non-sterile operator at the visualization tower 111 to the primary display 119 within the sterile field, where it can be viewed by a sterile operator at the operating table. In one example, the input can be in the form of a modification to the snapshot displayed on the non-sterile display 107 or 109, which can be routed to the primary display 119 by the hub 106.

Referring to FIG. 2, a surgical instrument 112 is being used in the surgical procedure as part of the surgical system 102. The hub 106 is also configured to coordinate information flow to a display of the surgical instrument 112. For example, coordinate information flow is further described in U.S. Provisional Patent Application Ser. No. 62/611,341, titled INTERACTIVE SURGICAL PLATFORM, filed Dec. 28, 2017, the disclosure of which is herein incorporated by reference in its entirety. A diagnostic input or feedback entered by a non-sterile operator at the visualization tower 111 can be routed by the hub 106 to the surgical instrument display 115 within the sterile field, where it can be viewed by the operator of the surgical instrument 112. Example surgical instruments that are suitable for use with the surgical system 102 are described under the heading "Surgical Instrument Hardware" in U.S. Provisional Patent Application Ser. No. 62/611,341, titled INTERACTIVE SURGICAL PLATFORM, filed Dec. 28, 2017, the disclosure of which is herein incorporated by reference in its entirety, for example.

Figure 3:
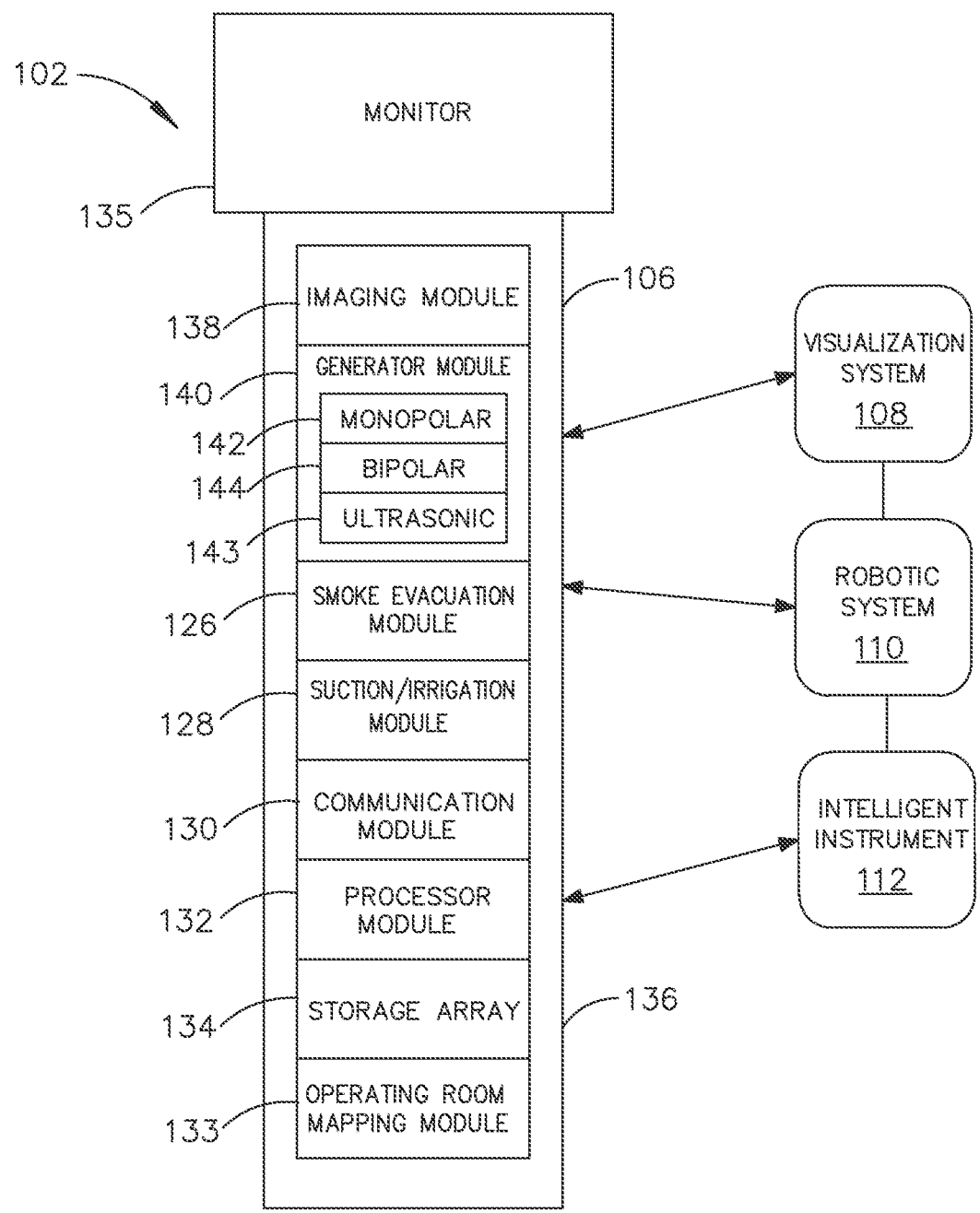
FIG. 3 is a surgical hub paired with a visualization system, a robotic system, and an intelligent instrument, in accordance with at least one aspect of the present disclosure.

Referring now to FIG. 3, a hub 106 is depicted in communication with a visualization system 108, a robotic system 110, and a handheld intelligent surgical instrument 112. The hub 106 includes a hub display 135, an imaging module 138, a generator module 140, a communication module 130, a processor module 132, and a storage array 134. In certain aspects, as illustrated in FIG. 3, the hub 106 further includes a smoke evacuation module 126 and/or a suction/irrigation module 128.

During a surgical procedure, energy application to tissue, for sealing and/or cutting, is generally associated with smoke evacuation, suction of excess fluid, and/or irrigation of the tissue. Fluid, power, and/or data lines from different sources are often entangled during the surgical procedure. Valuable time can be lost addressing this issue during a surgical procedure. Detangling the lines may necessitate disconnecting the lines from their respective modules, which may require resetting the modules. The hub modular enclosure 136 offers a unified environment for managing the power, data, and fluid lines, which reduces the frequency of entanglement between such lines.

Aspects of the present disclosure present a surgical hub for use in a surgical procedure that involves energy application to tissue at a surgical site. The surgical hub includes a hub enclosure and a combo generator module slidably receivable in a docking station of the hub enclosure. The docking station includes data and power contacts. The combo generator module includes two or more of an ultrasonic energy generator component, a bipolar RF energy generator component, and a monopolar RF energy generator component that are housed in a single unit. In one aspect, the combo generator module also includes a smoke evacuation component, at least one energy delivery cable for connecting the combo generator module to a surgical instrument, at least one smoke evacuation component configured to evacuate smoke, fluid, and/or particulates generated by the application of therapeutic energy to the tissue, and a fluid line extending from the remote surgical site to the smoke evacuation component.

In one aspect, the fluid line is a first fluid line and a second fluid line extends from the remote surgical site to a suction and irrigation module slidably received in the hub enclosure. In one aspect, the hub enclosure comprises a fluid interface.

Certain surgical procedures may require the application of more than one energy type to the tissue. One energy type may be more beneficial for cutting the tissue, while another different energy type may be more beneficial for sealing the tissue. For example, a bipolar generator can be used to seal the tissue while an ultrasonic generator can be used to cut the sealed tissue. Aspects of the present disclosure present a solution where a hub modular enclosure 136 is configured to accommodate different generators, and facilitate an interactive communication therebetween. One of the advantages of the hub modular enclosure 136 is enabling the quick removal and/or replacement of various modules.

Aspects of the present disclosure present a modular surgical enclosure for use in a surgical procedure that involves energy application to tissue. The modular surgical enclosure includes a first energy-generator module, configured to generate a first energy for application to the tissue, and a first docking station comprising a first docking port that includes first data and power contacts, wherein the first energy-generator module is slidably movable into an electrical engagement with the power and data contacts and wherein the first energy-generator module is slidably movable out of the electrical engagement with the first power and data contacts, Further to the above, the modular surgical enclosure also includes a second energy-generator module configured to generate a second energy, different than the first energy, for application to the tissue, and a second docking station comprising a second docking port that includes second data and power contacts, wherein the second energy-generator module is slidably movable into an electrical engagement with the power and data contacts, and wherein the second energy-generator module is slidably movable out of the electrical engagement with the second power and data contacts.

In addition, the modular surgical enclosure also includes a communication bus between the first docking port and the second docking port, configured to facilitate communication between the first energy-generator module and the second energy-generator module.

Figure 5:
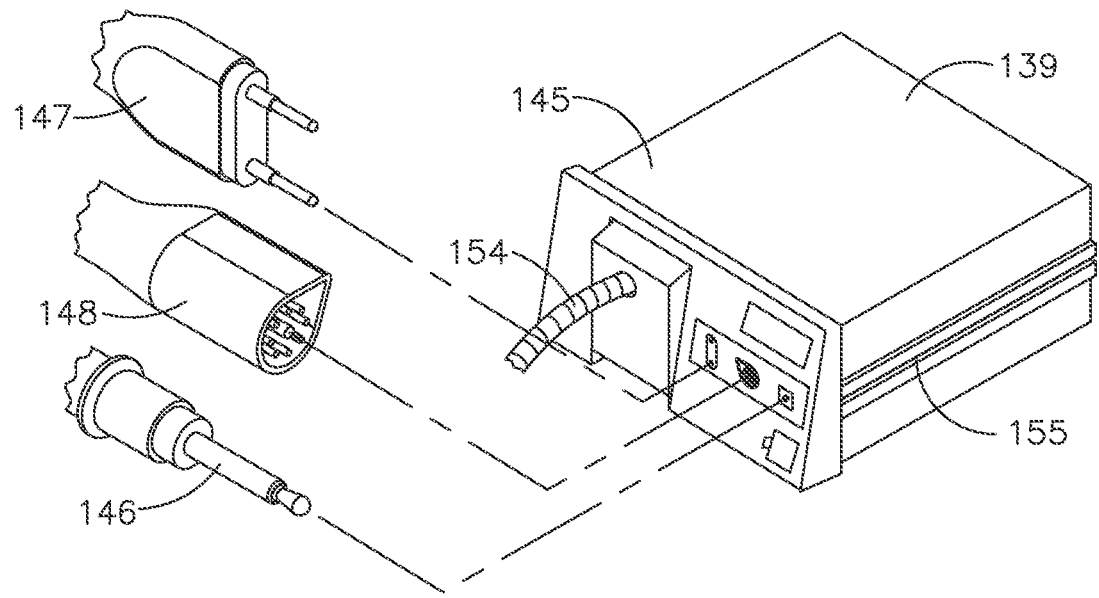
FIG. 5 is a perspective view of a combo generator module with bipolar, ultrasonic, and monopolar contacts and a smoke evacuation component, in accordance with at least one aspect of the present disclosure.

Referring to FIGS. 3-7, aspects of the present disclosure are presented for a hub modular enclosure 136 that allows the modular integration of a generator module 140, a smoke evacuation module 126, and a suction/irrigation module 128. The hub modular enclosure 136 further facilitates interactive communication between the modules 140, 126, 128. As illustrated in FIG. 5, the generator module 140 can be a generator module with integrated monopolar, bipolar, and ultrasonic components supported in a single housing unit 139 slidably insertable into the hub modular enclosure 136. As illustrated in FIG. 5, the generator module 140 can be configured to connect to a monopolar device 146, a bipolar device 147, and an ultrasonic device 148. Alternatively, the generator module 140 may comprise a series of monopolar, bipolar, and/or ultrasonic generator modules that interact through the hub modular enclosure 136. The hub modular enclosure 136 can be configured to facilitate the insertion of multiple generators and interactive communication between the generators docked into the hub modular enclosure 136 so that the generators would act as a single generator.

In one aspect, the hub modular enclosure 136 comprises a modular power and communication backplane 149 with external and wireless communication headers to enable the removable attachment of the modules 140, 126, 128 and interactive communication therebetween.

Figure 4:
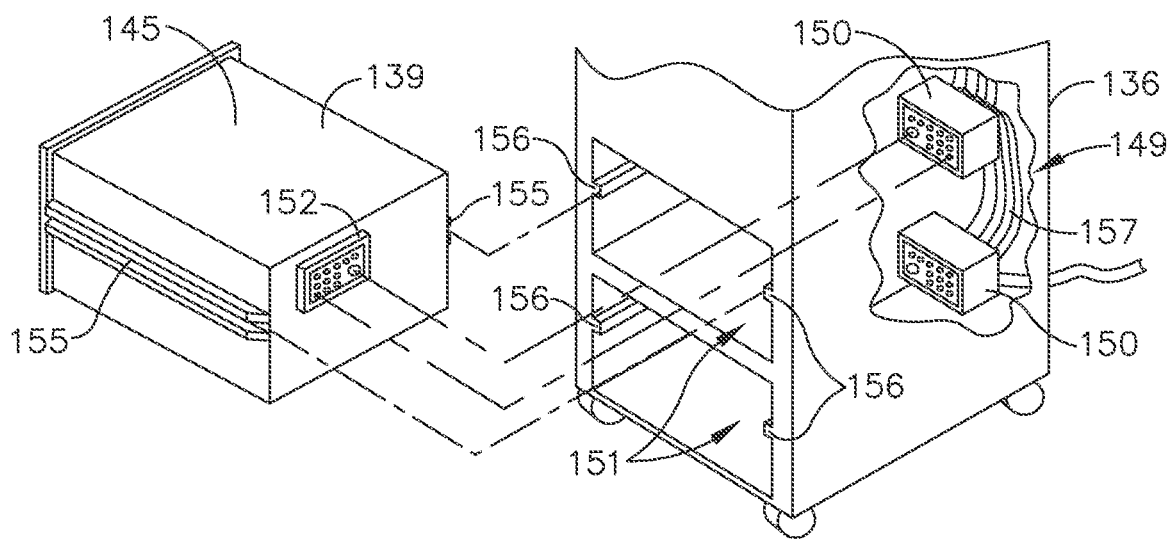
FIG. 4 is a partial perspective view of a surgical hub enclosure, and of a combo generator module slidably receivable in a drawer of the surgical hub enclosure, in accordance with at least one aspect of the present disclosure.

In one aspect, the hub modular enclosure 136 includes docking stations, or drawers, 151, herein also referred to as drawers, which are configured to slidably receive the modules 140, 126, 128. FIG. 4 illustrates a partial perspective view of a surgical hub enclosure 136, and a combo generator module 145 slidably receivable in a docking station 151 of the surgical hub enclosure 136. A docking port 152 with power and data contacts on a rear side of the combo generator module 145 is configured to engage a corresponding docking port 150 with power and data contacts of a corresponding docking station 151 of the hub modular enclosure 136 as the combo generator module 145 is slid into position within the corresponding docking station 151 of the hub module enclosure 136. In one aspect, the combo generator module 145 includes a bipolar, ultrasonic, and monopolar module and a smoke evacuation module integrated together into a single housing unit 139, as illustrated in FIG. 5.

In various aspects, the smoke evacuation module 126 includes a fluid line 154 that conveys captured/collected smoke and/or fluid away from a surgical site and to, for example, the smoke evacuation module 126. Vacuum suction originating from the smoke evacuation module 126 can draw the smoke into an opening of a utility conduit at the surgical site. The utility conduit, coupled to the fluid line, can be in the form of a flexible tube terminating at the smoke evacuation module 126. The utility conduit and the fluid line define a fluid path extending toward the smoke evacuation module 126 that is received in the hub enclosure 136.

In various aspects, the suction/irrigation module 128 is coupled to a surgical tool comprising an aspiration fluid line and a suction fluid line. In one example, the aspiration and suction fluid lines are in the form of flexible tubes extending from the surgical site toward the suction/irrigation module 128. One or more drive systems can be configured to cause irrigation and aspiration of fluids to and from the surgical site.

In one aspect, the surgical tool includes a shaft having an end effector at a distal end thereof and at least one energy treatment associated with the end effector, an aspiration tube, and an irrigation tube. The aspiration tube can have an inlet port at a distal end thereof and the aspiration tube extends through the shaft. Similarly, an irrigation tube can extend through the shaft and can have an inlet port in proximity to the energy deliver implement. The energy deliver implement is configured to deliver ultrasonic and/or RF energy to the surgical site and is coupled to the generator module 140 by a cable extending initially through the shaft.

The irrigation tube can be in fluid communication with a fluid source, and the aspiration tube can be in fluid communication with a vacuum source. The fluid source and/or the vacuum source can be housed in the suction/irrigation module 128. In one example, the fluid source and/or the vacuum source can be housed in the hub enclosure 136 separately from the suction/irrigation module 128. In such example, a fluid interface can be configured to connect the suction/irrigation module 128 to the fluid source and/or the vacuum source.

In one aspect, the modules 140, 126, 128 and/or their corresponding docking stations on the hub modular enclosure 136 may include alignment features that are configured to align the docking ports of the modules into engagement with their counterparts in the docking stations of the hub modular enclosure 136. For example, as illustrated in FIG. 4, the combo generator module 145 includes side brackets 155 that are configured to slidably engage with corresponding brackets 156 of the corresponding docking station 151 of the hub modular enclosure 136. The brackets cooperate to guide the docking port contacts of the combo generator module 145 into an electrical engagement with the docking port contacts of the hub modular enclosure 136.

In some aspects, the drawers 151 of the hub modular enclosure 136 are the same, or substantially the same size, and the modules are adjusted in size to be received in the drawers 151. For example, the side brackets 155 and/or 156 can be larger or smaller depending on the size of the module. In other aspects, the drawers 151 are different in size and are each designed to accommodate a particular module.

Furthermore, the contacts of a particular module can be keyed for engagement with the contacts of a particular drawer to avoid inserting a module into a drawer with mismatching contacts.

As illustrated in FIG. 4, the docking port 150 of one drawer 151 can be coupled to the docking port 150 of another drawer 151 through a communications link 157 to facilitate an interactive communication between the modules housed in the hub modular enclosure 136. The docking ports 150 of the hub modular enclosure 136 may alternatively, or additionally, facilitate a wireless interactive communication between the modules housed in the hub modular enclosure 136. Any suitable wireless communication can be employed, such as for example Air Titan-Bluetooth.

Figure 6:
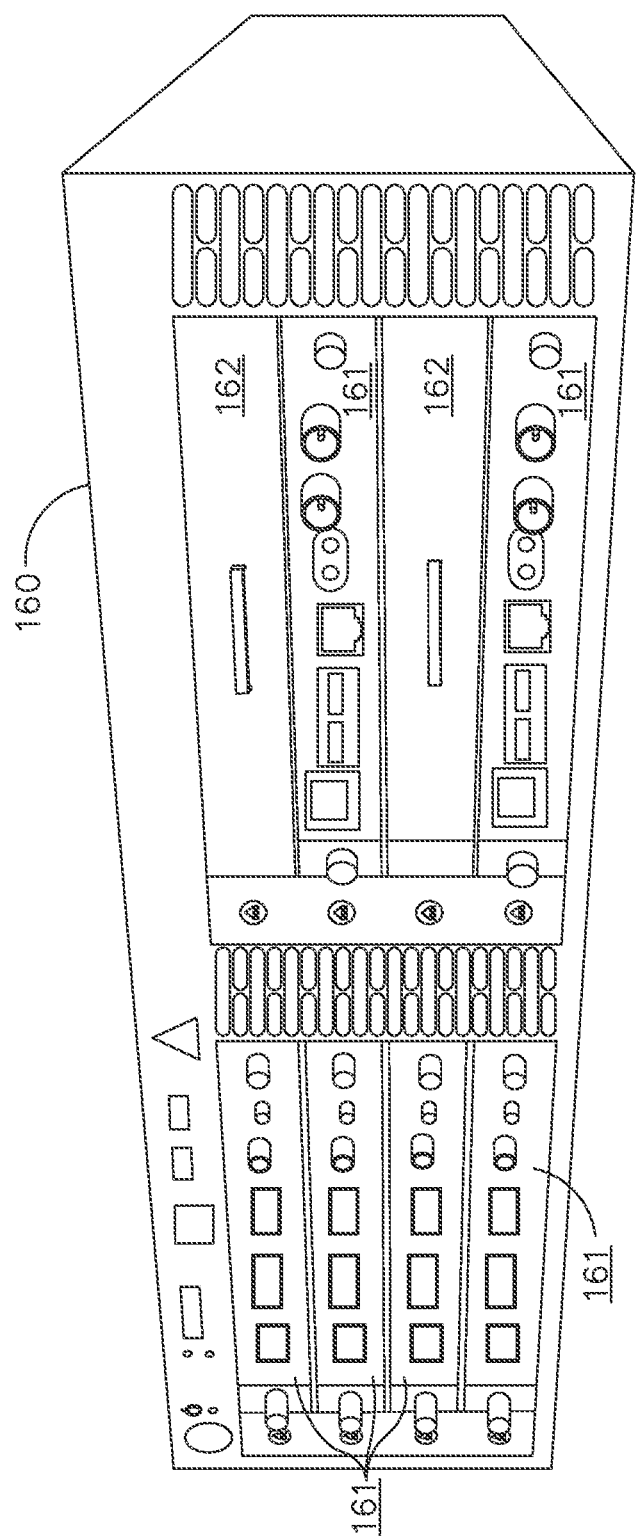
FIG. 6 illustrates individual power bus attachments for a plurality of lateral docking ports of a lateral modular housing configured to receive a plurality of modules, in accordance with at least one aspect of the present disclosure.

FIG. 6 illustrates individual power bus attachments for a plurality of lateral docking ports of a lateral modular housing 160 configured to receive a plurality of modules of a surgical hub 206. The lateral modular housing 160 is configured to laterally receive and interconnect the modules 161. The modules 161 are slidably inserted into docking stations 162 of lateral modular housing 160, which includes a backplane for interconnecting the modules 161. As illustrated in FIG. 6, the modules 161 are arranged laterally in the lateral modular housing 160. Alternatively, the modules 161 may be arranged vertically in a lateral modular housing.

Figure 7:
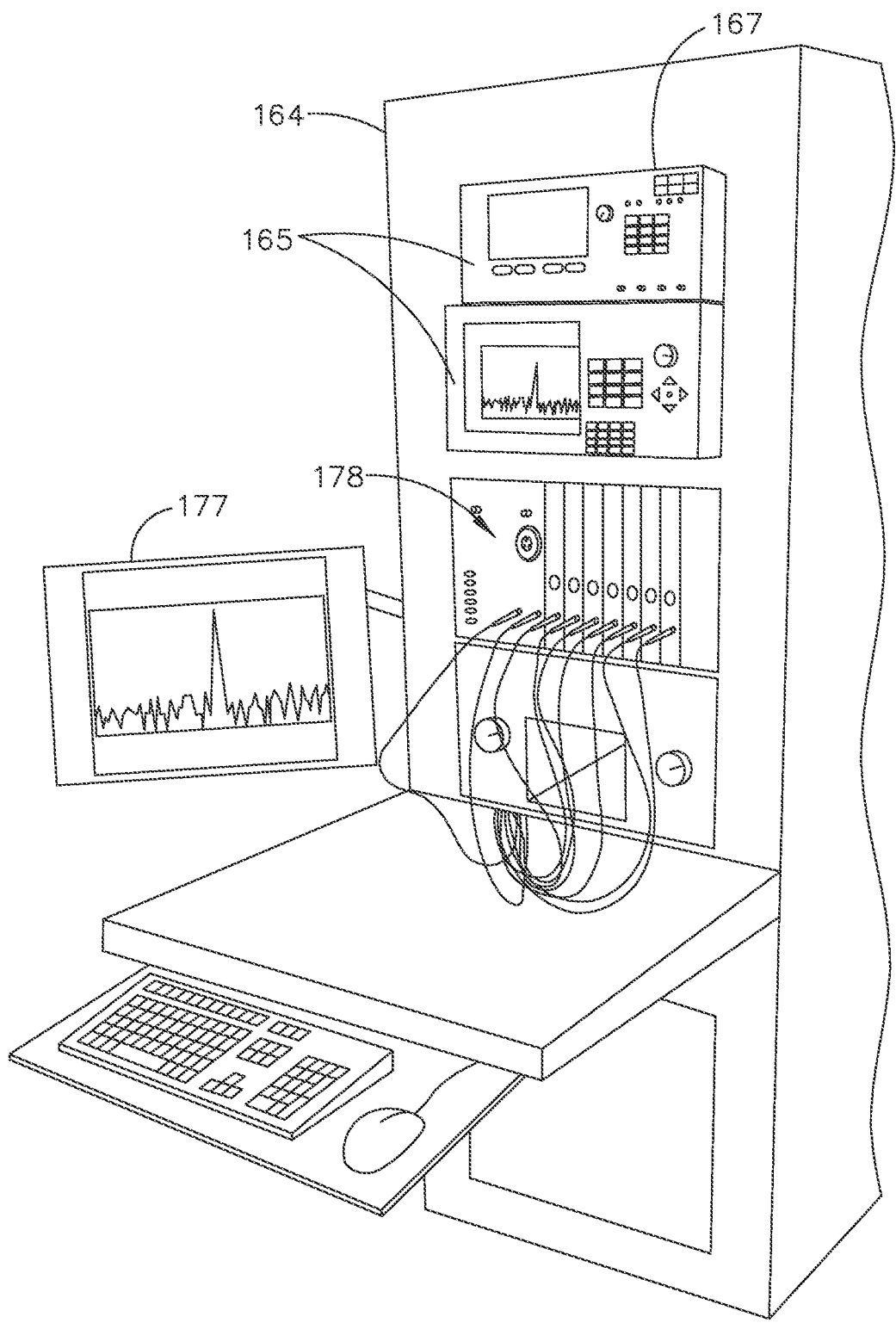
FIG. 7 illustrates a vertical modular housing configured to receive a plurality of modules, in accordance with at least one aspect of the present disclosure.

FIG. 7 illustrates a vertical modular housing 164 configured to receive a plurality of modules 165 of the surgical hub 106. The modules 165 are slidably inserted into docking stations, or drawers, 167 of vertical modular housing 164, which includes a backplane for interconnecting the modules 165. Although the drawers 167 of the vertical modular housing 164 are arranged vertically, in certain instances, a vertical modular housing 164 may include drawers that are arranged laterally. Furthermore, the modules 165 may interact with one another through the docking ports of the vertical modular housing 164. In the example of FIG. 7, a display 177 is provided for displaying data relevant to the operation of the modules 165. In addition, the vertical modular housing 164 includes a master module 178 housing a plurality of sub-modules that are slidably received in the master module 178.

In various aspects, the imaging module 138 comprises an integrated video processor and a modular light source and is adapted for use with various imaging devices. In one aspect, the imaging device is comprised of a modular housing that can be assembled with a light source module and a camera module. The housing can be a disposable housing. In at least one example, the disposable housing is removably coupled to a reusable controller, a light source module, and a camera module. The light source module and/or the camera module can be selectively chosen depending on the type of surgical procedure. In one aspect, the camera module comprises a CCD sensor. In another aspect, the camera module comprises a CMOS sensor. In another aspect, the camera module is configured for scanned beam imaging. Likewise, the light source module can be configured to deliver a white light or a different light, depending on the surgical procedure.

During a surgical procedure, removing a surgical device from the surgical field and replacing it with another surgical device that includes a different camera or a different light source can be inefficient. Temporarily losing sight of the surgical field may lead to undesirable consequences. The module imaging device of the present disclosure is configured to permit the replacement of a light source module or a camera module midstream during a surgical procedure, without having to remove the imaging device from the surgical field.

In one aspect, the imaging device comprises a tubular housing that includes a plurality of channels. A first channel is configured to slidably receive the camera module, which can be configured for a snap-fit engagement with the first channel. A second channel is configured to slidably receive the light source module, which can be configured for a snap-fit engagement with the second channel. In another example, the camera module and/or the light source module can be rotated into a final position within their respective channels. A threaded engagement can be employed in lieu of the snap-fit engagement.

In various examples, multiple imaging devices are placed at different positions in the surgical field to provide multiple views. The imaging module 138 can be configured to switch between the imaging devices to provide an optimal view. In various aspects, the imaging module 138 can be configured to integrate the images from the different imaging device.

Various image processors and imaging devices suitable for use with the present disclosure are described in U.S. Pat. No. 7,995,045, titled COMBINED SBI AND CONVENTIONAL IMAGE PROCESSOR, which issued on Aug. 9, 2011, which is herein incorporated by reference in its entirety. In addition, U.S. Pat. No. 7,982,776, titled SBI MOTION ARTIFACT REMOVAL APPARATUS AND METHOD, which issued on Jul. 19, 2011, which is herein incorporated by reference in its entirety, describes various systems for removing motion artifacts from image data. Such systems can be integrated with the imaging module 138. Furthermore, U.S. Patent Application Publication No. 2011/0306840, titled CONTROLLABLE MAGNETIC SOURCE TO FIXTURE INTRACORPOREAL APPARATUS, which published on Dec. 15, 2011, and U.S. Patent Application Publication No. 2014/0243597, titled SYSTEM FOR PERFORMING A MINIMALLY INVASIVE SURGICAL PROCEDURE, which published on Aug. 28, 2014, each of which is herein incorporated by reference in its entirety.

Figure 8:
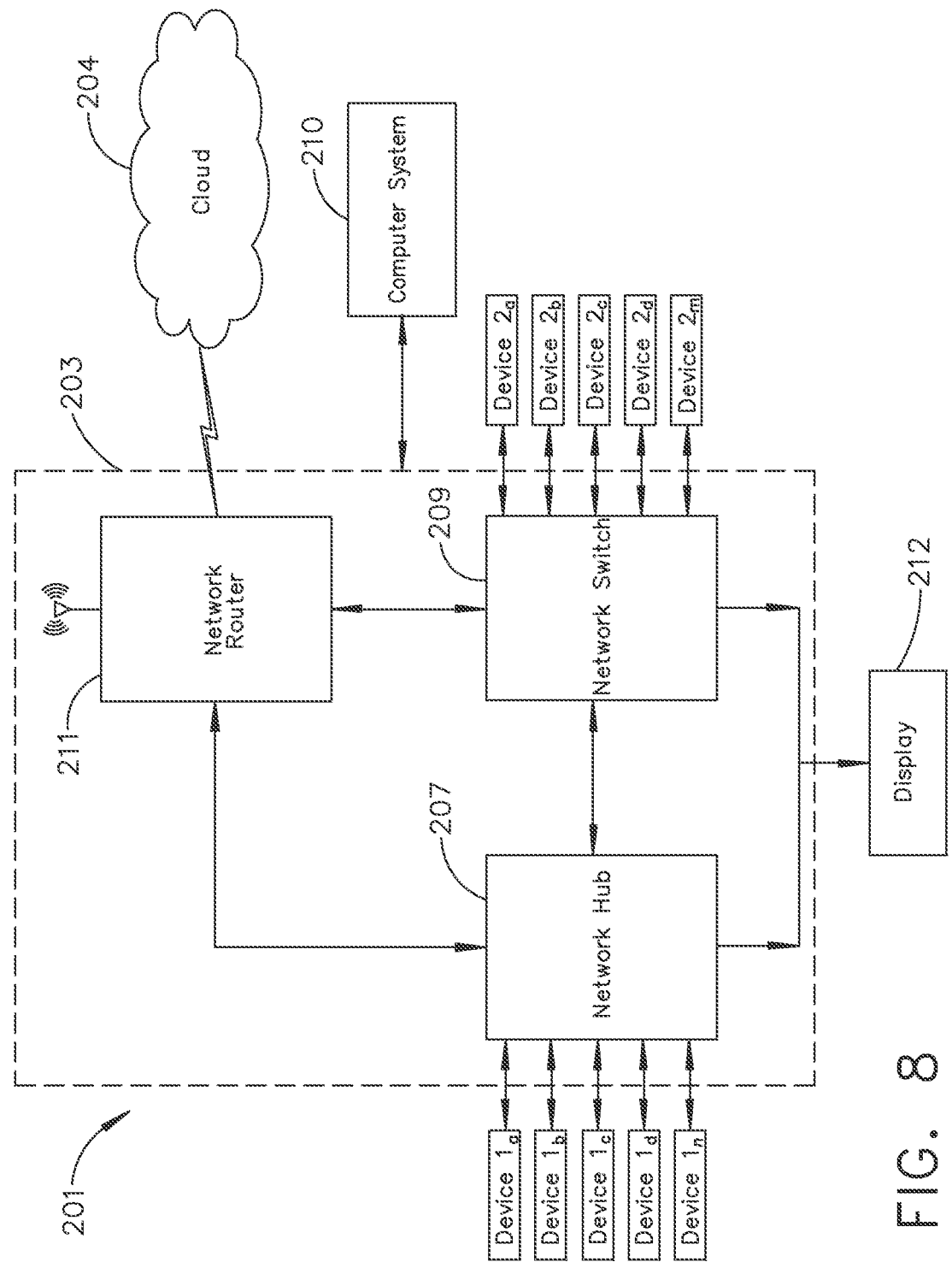
FIG. 8 illustrates a surgical data network comprising a modular communication hub configured to connect modular devices located in one or more operating theaters of a healthcare facility, or any room in a healthcare facility specially equipped for surgical operations, to the cloud, in accordance with at least one aspect of the present disclosure.

FIG. 8 illustrates a surgical data network 201 comprising a modular communication hub 203 configured to connect modular devices located in one or more operating theaters of a healthcare facility, or any room in a healthcare facility specially equipped for surgical operations, to a cloud-based system (e.g., the cloud 204 that may include a remote server 213 coupled to a storage device 205). In one aspect, the modular communication hub 203 comprises a network hub 207 and/or a network switch 209 in communication with a network router. The modular communication hub 203 also can be coupled to a local computer system 210 to provide local computer processing and data manipulation. The surgical data network 201 may be configured as passive, intelligent, or switching. A passive surgical data network serves as a conduit for the data, enabling it to go from one device (or segment) to another and to the cloud computing resources. An intelligent surgical data network includes additional features to enable the traffic passing through the surgical data network to be monitored and to configure each port in the network hub 207 or network switch 209. An intelligent surgical data network may be referred to as a manageable hub or switch. A switching hub reads the destination address of each packet and then forwards the packet to the correct port.

Modular devices 1a-1n located in the operating theater may be coupled to the modular communication hub 203. The network hub 207 and/or the network switch 209 may be coupled to a network router 211 to connect the devices 1a-1n to the cloud 204 or the local computer system 210. Data associated with the devices 1a-1n may be transferred to cloud-based computers via the router for remote data processing and manipulation. Data associated with the devices 1a-1n may also be transferred to the local computer system 210 for local data processing and manipulation. Modular devices 2a-2m located in the same operating theater also may be coupled to a network switch 209. The network switch 209 may be coupled to the network hub 207 and/or the network router 211 to connect to the devices 2a-2m to the cloud 204. Data associated with the devices 2a-2n may be transferred to the cloud 204 via the network router 211 for data processing and manipulation. Data associated with the devices 2a-2m may also be transferred to the local computer system 210 for local data processing and manipulation.

It will be appreciated that the surgical data network 201 may be expanded by interconnecting multiple network hubs 207 and/or multiple network switches 209 with multiple network routers 211. The modular communication hub 203 may be contained in a modular control tower configured to receive multiple devices 1a-1n/2a-2m. The local computer system 210 also may be contained in a modular control tower. The modular communication hub 203 is connected to a display 212 to display images obtained by some of the devices 1a-1n/2a-2m, for example during surgical procedures. In various aspects, the devices 1a-1n/2a-2m may include, for example, various modules such as an imaging module 138 coupled to an endoscope, a generator module 140 coupled to an energy-based surgical device, a smoke evacuation module 126, a suction/irrigation module 128, a communication module 130, a processor module 132, a storage array 134, a surgical device coupled to a display, and/or a non-contact sensor module, among other modular devices that may be connected to the modular communication hub 203 of the surgical data network 201.

In one aspect, the surgical data network 201 may comprise a combination of network hub(s), network switch(es), and network router(s) connecting the devices 1a-1n/2a-2m to the cloud. Any one of or all of the devices 1a-1n/2a-2m coupled to the network hub or network switch may collect data in real time and transfer the data to cloud computers for data processing and manipulation. It will be appreciated that cloud computing relies on sharing computing resources rather than having local servers or personal devices to handle software applications. The word "cloud" may be used as a metaphor for "the Internet," although the term is not limited as such. Accordingly, the term "cloud computing" may be used herein to refer to "a type of Internet-based computing," where different services—such as servers, storage, and applications—are delivered to the modular communication hub 203 and/or computer system 210 located in the surgical theater (e.g., a fixed, mobile, temporary, or field operating room or space) and to devices connected to the modular communication hub 203 and/or computer system 210 through the Internet. The cloud infrastructure may be maintained by a cloud service provider. In this context, the cloud service provider may be the entity that coordinates the usage and control of the devices 1a-1n/2a-2m located in one or more operating theaters. The cloud computing services can perform a large number of calculations based on the data gathered by smart surgical instruments, robots, and other computerized devices located in the operating theater. The hub hardware enables multiple devices or connections to be connected to a computer that communicates with the cloud computing resources and storage.

Applying cloud computer data processing techniques on the data collected by the devices 1a-1n/2a-2m, the surgical data network provides improved surgical outcomes, reduced costs, and improved patient satisfaction. At least some of the devices 1a-1n/2a-2m may be employed to view tissue states to assess leaks or perfusion of sealed tissue after a tissue sealing and cutting procedure. At least some of the devices 1a-1n/2a-2m may be employed to identify pathology, such as the effects of diseases, using the cloud-based computing to examine data including images of samples of body tissue for diagnostic purposes. This includes localization and margin confirmation of tissue and phenotypes. At least some of the devices 1a-1n/2a-2m may be employed to identify anatomical structures of the body using a variety of sensors integrated with imaging devices and techniques such as overlaying images captured by multiple imaging devices. The data gathered by the devices 1a-1n/2a-2m, including image data, may be transferred to the cloud 204 or the local computer system 210 or both for data processing and manipulation including image processing and manipulation. The data may be analyzed to improve surgical procedure outcomes by determining if further treatment, such as the application of endoscopic intervention, emerging technologies, a targeted radiation, targeted intervention, and precise robotics to tissue-specific sites and conditions, may be pursued. Such data analysis may further employ outcome analytics processing, and using standardized approaches may provide beneficial feedback to either confirm surgical treatments and the behavior of the surgeon or suggest modifications to surgical treatments and the behavior of the surgeon.

In one implementation, the operating theater devices 1a-1n may be connected to the modular communication hub 203 over a wired channel or a wireless channel depending on the configuration of the devices 1a-1n to a network hub. The network hub 207 may be implemented, in one aspect, as a local network broadcast device that works on the physical layer of the Open System Interconnection (OSI) model. The network hub provides connectivity to the devices 1a-1n located in the same operating theater network. The network hub 207 collects data in the form of packets and sends them to the router in half duplex mode. The network hub 207 does not store any media access control/Internet Protocol (MAC/IP) to transfer the device data. Only one of the devices 1a-1n can send data at a time through the network hub 207. The network hub 207 has no routing tables or intelligence regarding where to send information and broadcasts all network data across each connection and to a remote server 213 (FIG. 9) over the cloud 204. The network hub 207 can detect basic network errors such as collisions, but having all information broadcast to multiple ports can be a security risk and cause bottlenecks.

In another implementation, the operating theater devices 2a-2m may be connected to a network switch 209 over a wired channel or a wireless channel. The network switch 209 works in the data link layer of the OSI model. The network switch 209 is a multicast device for connecting the devices 2a-2m located in the same operating theater to the network. The network switch 209 sends data in the form of frames to the network router 211 and works in full duplex mode. Multiple devices 2a-2m can send data at the same time through the network switch 209. The network switch 209 stores and uses MAC addresses of the devices 2a-2m to transfer data.

The network hub 207 and/or the network switch 209 are coupled to the network router 211 for connection to the cloud 204. The network router 211 works in the network layer of the OSI model. The network router 211 creates a route for transmitting data packets received from the network hub 207 and/or network switch 211 to cloud-based computer resources for further processing and manipulation of the data collected by any one of or all the devices 1a-1n/2a-2m. The network router 211 may be employed to connect two or more different networks located in different locations, such as, for example, different operating theaters of the same healthcare facility or different networks located in different operating theaters of different healthcare facilities. The network router 211 sends data in the form of packets to the cloud 204 and works in full duplex mode. Multiple devices can send data at the same time. The network router 211 uses IP addresses to transfer data.

In one example, the network hub 207 may be implemented as a USB hub, which allows multiple USB devices to be connected to a host computer. The USB hub may expand a single USB port into several tiers so that there are more ports available to connect devices to the host system computer. The network hub 207 may include wired or wireless capabilities to receive information over a wired channel or a wireless channel. In one aspect, a wireless USB short-range, high-bandwidth wireless radio communication protocol may be employed for communication between the devices 1a-1n and devices 2a-2m located in the operating theater.

In other examples, the operating theater devices 1a-1n/2a-2m may communicate to the modular communication hub 203 via Bluetooth wireless technology standard for exchanging data over short distances (using short-wavelength UHF radio waves in the ISM band from 2.4 to 2.485 GHz) from fixed and mobile devices and building personal area networks (PANs). In other aspects, the operating theater devices 1a-1n/2a-2m may communicate to the modular communication hub 203 via a number of wireless or wired communication standards or protocols, including but not limited to Wi-Fi (IEEE 802.11 family), WiMAX (IEEE 802.16 family), IEEE 802.20, long-term evolution (LTE), and Ev-DO, HSPA+, HSDPA+, HSUPA+, EDGE, GSM, GPRS, CDMA, TDMA, DECT, and Ethernet derivatives thereof, as well as any other wireless and wired protocols that are designated as 3G, 4G, 5G, and beyond. The computing module may include a plurality of communication modules. For instance, a first communication module may be dedicated to shorter-range wireless communications such as Wi-Fi and Bluetooth, and a second communication module may be dedicated to longer-range wireless communications such as GPS, EDGE, GPRS, CDMA, WiMAX, LTE, Ev-DO, and others.

The modular communication hub 203 may serve as a central connection for one or all of the operating theater devices 1a-1n/2a-2m and handles a data type known as frames. Frames carry the data generated by the devices 1a-1n/2a-2m. When a frame is received by the modular communication hub 203, it is amplified and transmitted to the network router 211, which transfers the data to the cloud computing resources by using a number of wireless or wired communication standards or protocols, as described herein.

The modular communication hub 203 can be used as a standalone device or be connected to compatible network hubs and network switches to form a larger network. The modular communication hub 203 is generally easy to install, configure, and maintain, making it a good option for networking the operating theater devices 1*a*-1*n*/2*a*-2*m*.

Figure 9:
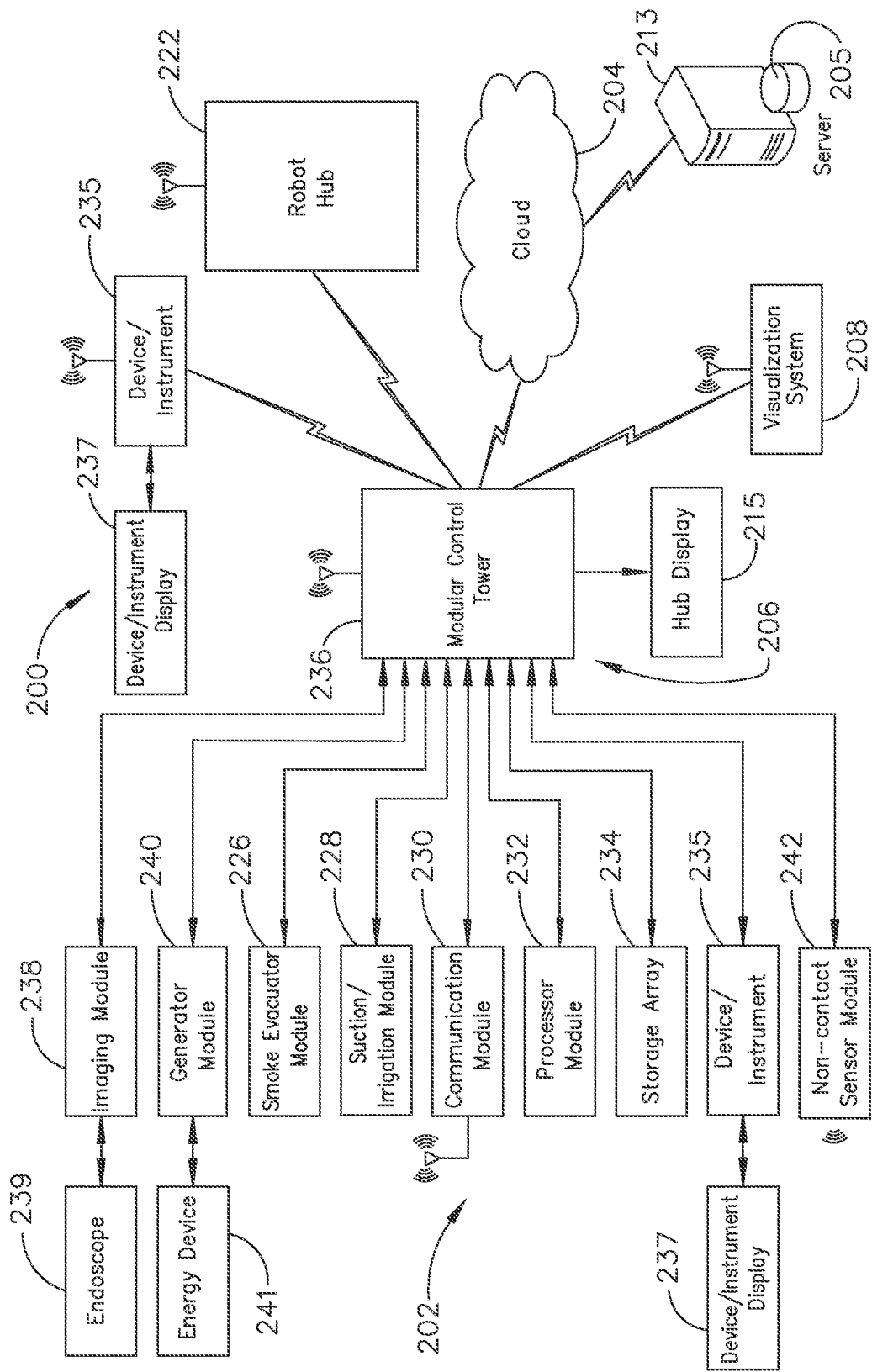
FIG. 9 illustrates a computer-implemented interactive surgical system, in accordance with at least one aspect of the present disclosure.
Figure 10:
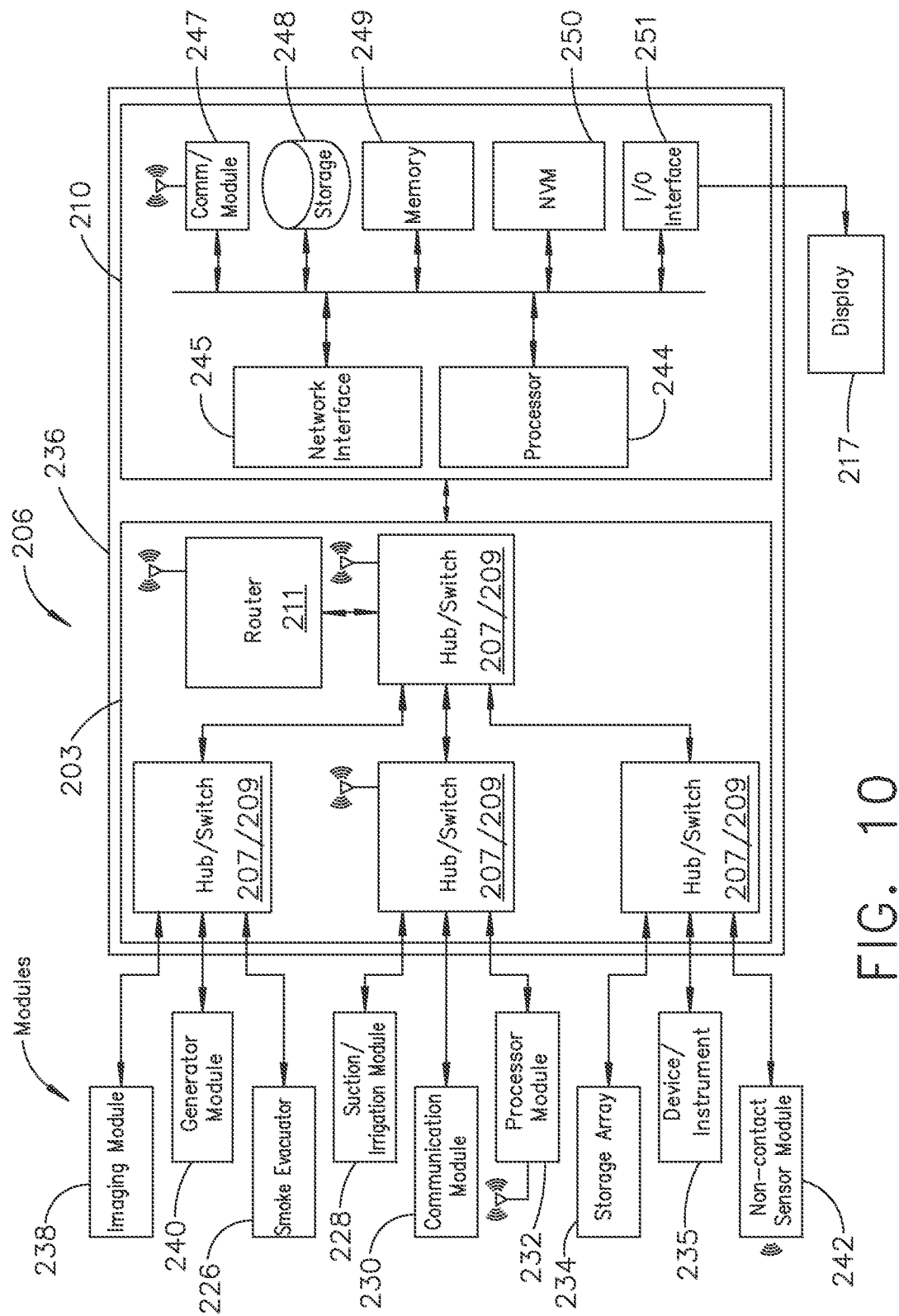
FIG. 10 illustrates a surgical hub comprising a plurality of modules coupled to the modular control tower, in accordance with at least one aspect of the present disclosure.

FIG. 9 illustrates a computer-implemented interactive surgical system 200. The computer-implemented interactive surgical system 200 is similar in many respects to the computer-implemented interactive surgical system 100. For example, the computer-implemented interactive surgical system 200 includes one or more surgical systems 202, which are similar in many respects to the surgical systems 102. Each surgical system 202 includes at least one surgical hub 206 in communication with a cloud 204 that may include a remote server 213. In one aspect, the computer-implemented interactive surgical system 200 comprises a modular control tower 236 connected to multiple operating theater devices such as, for example, intelligent surgical instruments, robots, and other computerized devices located in the operating theater. As shown in FIG. 10, the modular control tower 236 comprises a modular communication hub 203 coupled to a computer system 210. As illustrated in the example of FIG. 9, the modular control tower 236 is coupled to an imaging module 238 that is coupled to an endoscope 239, a generator module 240 that is coupled to an energy device 241, a smoke evacuator module 226, a suction/irrigation module 228, a communication module 230, a processor module 232, a storage array 234, a smart device/instrument 235 optionally coupled to a display 237, and a non-contact sensor module 242. The operating theater devices are coupled to cloud computing resources and data storage via the modular control tower 236. A robot hub 222 also may be connected to the modular control tower 236 and to the cloud computing resources. The devices/instruments 235, visualization systems 208, among others, may be coupled to the modular control tower 236 via wired or wireless communication standards or protocols, as described herein. The modular control tower 236 may be coupled to a hub display 215 (e.g., monitor, screen) to display and overlay images received from the imaging module, device/instrument display, and/or other visualization systems 208. The hub display also may display data received from devices connected to the modular control tower in conjunction with images and overlaid images.

FIG. 10 illustrates a surgical hub 206 comprising a plurality of modules coupled to the modular control tower 236. The modular control tower 236 comprises a modular communication hub 203, e.g., a network connectivity device, and a computer system 210 to provide local processing, visualization, and imaging, for example. As shown in FIG. 10, the modular communication hub 203 may be connected in a tiered configuration to expand the number of modules (e.g., devices) that may be connected to the modular communication hub 203 and transfer data associated with the modules to the computer system 210, cloud computing resources, or both. As shown in FIG. 10, each of the network hubs/switches in the modular communication hub 203 includes three downstream ports and one upstream port. The upstream network hub/switch is connected to a processor to provide a communication connection to the cloud computing resources and a local display 217. Communication to the cloud 204 may be made either through a wired or a wireless communication channel.

The surgical hub 206 employs a non-contact sensor module 242 to measure the dimensions of the operating theater and generate a map of the surgical theater using either ultrasonic or laser-type non-contact measurement devices. An ultrasound-based non-contact sensor module scans the operating theater by transmitting a burst of ultrasound and receiving the echo when it bounces off the perimeter walls of an operating theater as described under the heading "Surgical Hub Spatial Awareness Within an Operating Room" in U.S. Provisional Patent Application Ser. No. 62/611,341, titled INTERACTIVE SURGICAL PLATFORM, filed Dec. 28, 2017, which is herein incorporated by reference in its entirety, in which the sensor module is configured to determine the size of the operating theater and to adjust Bluetooth-pairing distance limits. A laser-based non-contact sensor module scans the operating theater by transmitting laser light pulses, receiving laser light pulses that bounce off the perimeter walls of the operating theater, and comparing the phase of the transmitted pulse to the received pulse to determine the size of the operating theater and to adjust Bluetooth pairing distance limits, for example.

The computer system 210 comprises a processor 244 and a network interface 245. The processor 244 is coupled to a communication module 247, storage 248, memory 249, non-volatile memory 250, and input/output interface 251 via a system bus. The system bus can be any of several types of bus structure(s) including the memory bus or memory controller, a peripheral bus or external bus, and/or a local bus using any variety of available bus architectures including, but not limited to, 9-bit bus, Industrial Standard Architecture (ISA), Micro-Charnel Architecture (MSA), Extended ISA (EISA), Intelligent Drive Electronics (IDE), VESA Local Bus (VLB), Peripheral Component Interconnect (PCI), USB, Advanced Graphics Port (AGP), Personal Computer Memory Card International Association bus (PCMCIA), Small Computer Systems Interface (SCSI), or any other proprietary bus.

The processor 244 may be any single-core or multicore processor such as those known under the trade name ARM Cortex by Texas Instruments. In one aspect, the processor may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle serial random access memory (SRAM), an internal read-only memory (ROM) loaded with StellarisWare® software, a 2 KB electrically erasable programmable read-only memory (EEPROM), and/or one or more pulse width modulation (PWM) modules, one or more quadrature encoder inputs (QEI) analogs, one or more 12-bit analog-to-digital converters (ADCs) with 12 analog input channels, details of which are available for the product datasheet.

In one aspect, the processor 244 may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The system memory includes volatile memory and non-volatile memory. The basic input/output system (BIOS), containing the basic routines to transfer information between elements within the computer system, such as during start-up, is stored in non-volatile memory. For example, the non-volatile memory can include ROM, programmable ROM (PROM), electrically programmable ROM (EPROM), EEPROM, or flash memory. Volatile memory includes random-access memory (RAM), which acts as external cache memory. Moreover, RAM is available in many forms such as SRAM, dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM).

The computer system 210 also includes removable/non-removable, volatile/non-volatile computer storage media, such as for example disk storage. The disk storage includes, but is not limited to, devices like a magnetic disk drive, floppy disk drive, tape drive, Jaz drive, Zip drive, LS-60 drive, flash memory card, or memory stick. In addition, the disk storage can include storage media separately or in combination with other storage media including, but not limited to, an optical disc drive such as a compact disc ROM device (CD-ROM), compact disc recordable drive (CD-R Drive), compact disc rewritable drive (CD-RW Drive), or a digital versatile disc ROM drive (DVD-ROM). To facilitate the connection of the disk storage devices to the system bus, a removable or non-removable interface may be employed.

It is to be appreciated that the computer system 210 includes software that acts as an intermediary between users and the basic computer resources described in a suitable operating environment. Such software includes an operating system. The operating system, which can be stored on the disk storage, acts to control and allocate resources of the computer system. System applications take advantage of the management of resources by the operating system through program modules and program data stored either in the system memory or on the disk storage. It is to be appreciated that various components described herein can be implemented with various operating systems or combinations of operating systems.

A user enters commands or information into the computer system 210 through input device(s) coupled to the I/O interface 251. The input devices include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processor through the system bus via interface port(s). The interface port(s) include, for example, a serial port, a parallel port, a game port, and a USB. The output device(s) use some of the same types of ports as input device(s). Thus, for example, a USB port may be used to provide input to the computer system and to output information from the computer system to an output device. An output adapter is provided to illustrate that there are some output devices like monitors, displays, speakers, and printers, among other output devices that require special adapters. The output adapters include, by way of illustration and not limitation, video and sound cards that provide a means of connection between the output device and the system bus. It should be noted that other devices and/or systems of devices, such as remote computer(s), provide both input and output capabilities.

The computer system 210 can operate in a networked environment using logical connections to one or more remote computers, such as cloud computer(s), or local computers. The remote cloud computer(s) can be a personal computer, server, router, network PC, workstation, microprocessor-based appliance, peer device, or other common network node, and the like, and typically includes many or all of the elements described relative to the computer system. For purposes of brevity, only a memory storage device is illustrated with the remote computer(s). The remote computer(s) is logically connected to the computer system through a network interface and then physically connected via a communication connection. The network interface encompasses communication networks such as local area networks (LANs) and wide area networks (WANs). LAN technologies include Fiber Distributed Data Interface (FDDI), Copper Distributed Data Interface (CDDI), Ethernet/IEEE 802.3, Token Ring/IEEE 802.5 and the like. WAN technologies include, but are not limited to, point-to-point links, circuit-switching networks like Integrated Services Digital Networks (ISDN) and variations thereon, packet-switching networks, and Digital Subscriber Lines (DSL).

In various aspects, the computer system 210 of FIG. 10, the imaging module 238 and/or visualization system 208, and/or the processor module 232 of FIGS. 9-10, may comprise an image processor, image-processing engine, media processor, or any specialized digital signal processor (DSP) used for the processing of digital images. The image processor may employ parallel computing with single instruction, multiple data (SIMD) or multiple instruction, multiple data (MIMD) technologies to increase speed and efficiency. The digital image-processing engine can perform a range of tasks. The image processor may be a system on a chip with multicore processor architecture.

The communication connection(s) refers to the hardware/software employed to connect the network interface to the bus. While the communication connection is shown for illustrative clarity inside the computer system, it can also be external to the computer system 210. The hardware/software necessary for connection to the network interface includes, for illustrative purposes only, internal and external technologies such as modems, including regular telephone-grade modems, cable modems, and DSL modems, ISDN adapters, and Ethernet cards.

In various aspects, the devices/instruments 235 described with reference to FIGS. 9-10, may be implemented as a circular powered stapling device 201800 (FIGS. 24-30), 201502 (FIGS. 31-33), 201532 (FIGS. 34-35), 201610 (FIGS. 36-40). Accordingly, the circular powered stapling device 201800 (FIGS. 24-30), 201502 (FIGS. 31-33), 201532 (FIGS. 34-35), 201610 (FIGS. 36-40) is configured to interface with the modular control tower 236 ant the surgical hub 206. Once connected to the surgical hub 206 the circular powered stapling device 201800 (FIGS. 24-30), 201502 (FIGS. 31-33), 201532 (FIGS. 34-35), 201610 (FIGS. 36-40) is configured to interface with the cloud 204, the server 213, other hub connected instruments, the hub display 215, or the visualization system 209, or combinations thereof. Further, once connected to hub 206, the circular powered stapling device 201800 (FIGS. 24-30), 201502 (FIGS. 31-33), 201532 (FIGS. 34-35), 201610 (FIGS. 36-40) may utilize the processing circuits available in the hub local computer system 210.

Figure 11:
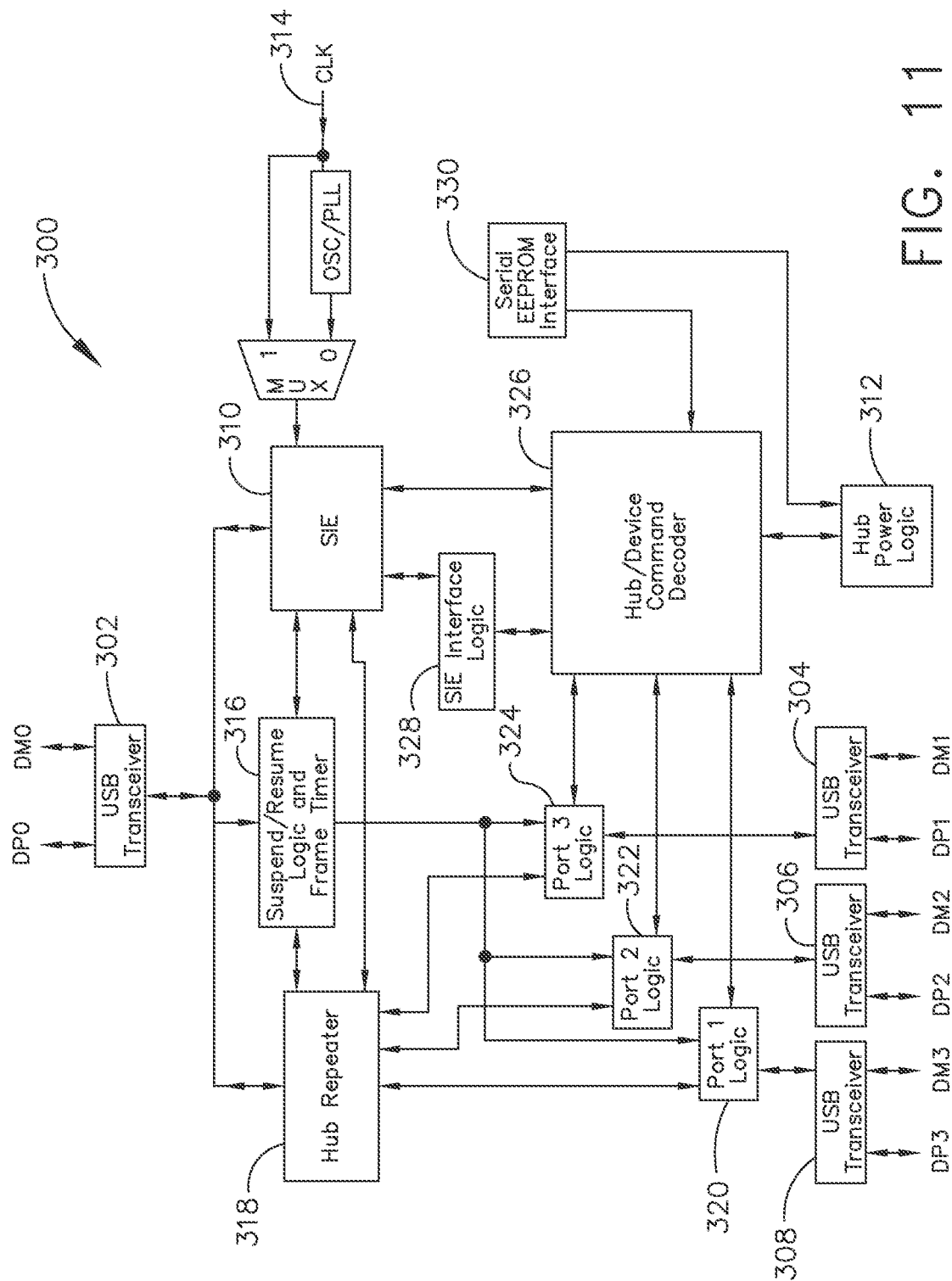
FIG. 11 illustrates one aspect of a Universal Serial Bus (USB) network hub device, in accordance with at least one aspect of the present disclosure.

FIG. 11 illustrates a functional block diagram of one aspect of a USB network hub 300 device, in accordance with at least one aspect of the present disclosure. In the illustrated aspect, the USB network hub device 300 employs a TUSB2036 integrated circuit hub by Texas Instruments. The USB network hub 300 is a CMOS device that provides an upstream USB transceiver port 302 and up to three downstream USB transceiver ports 304, 306, 308 in compliance with the USB 2.0 specification. The upstream USB transceiver port 302 is a differential root data port comprising a differential data minus (DM0) input paired with a differential data plus (DP0) input. The three downstream USB transceiver ports 304, 306, 308 are differential data ports where each port includes differential data plus (DP1-DP3) outputs paired with differential data minus (DM1-DM3) outputs.

The USB network hub 300 device is implemented with a digital state machine instead of a microcontroller, and no firmware programming is required. Fully compliant USB transceivers are integrated into the circuit for the upstream USB transceiver port 302 and all downstream USB transceiver ports 304, 306, 308. The downstream USB transceiver ports 304, 306, 308 support both full-speed and low-speed devices by automatically setting the slew rate according to the speed of the device attached to the ports. The USB network hub 300 device may be configured either in bus-powered or self-powered mode and includes a hub power logic 312 to manage power.

The USB network hub 300 device includes a serial interface engine 310 (SIE). The SIE 310 is the front end of the USB network hub 300 hardware and handles most of the protocol described in chapter 8 of the USB specification. The SIE 310 typically comprehends signaling up to the transaction level. The functions that it handles could include: packet recognition, transaction sequencing, SOP, EOP, RESET, and RESUME signal detection/generation, clock/data separation, non-return-to-zero invert (NRZI) data encoding/decoding and bit-stuffing, CRC generation and checking (token and data), packet ID (PID) generation and checking/decoding, and/or serial-parallel/parallel-serial conversion. The 310 receives a clock input 314 and is coupled to a suspend/resume logic and frame timer 316 circuit and a hub repeater circuit 318 to control communication between the upstream USB transceiver port 302 and the downstream USB transceiver ports 304, 306, 308 through port logic circuits 320, 322, 324. The SIE 310 is coupled to a command decoder 326 via interface logic to control commands from a serial EEPROM via a serial EEPROM interface 330.

In various aspects, the USB network hub 300 can connect 127 functions configured in up to six logical layers (tiers) to a single computer. Further, the USB network hub 300 can connect to all peripherals using a standardized four-wire cable that provides both communication and power distribution. The power configurations are bus-powered and self-powered modes. The USB network hub 300 may be configured to support four modes of power management: a bus-powered hub, with either individual-port power management or ganged-port power management, and the self-powered hub, with either individual-port power management or ganged-port power management. In one aspect, using a USB cable, the USB network hub 300, the upstream USB transceiver port 302 is plugged into a USB host controller, and the downstream USB transceiver ports 304, 306, 308 are exposed for connecting USB compatible devices, and so forth.

Additional details regarding the structure and function of the surgical hub and/or surgical hub networks can be found in U.S. Provisional Patent Application No. 62/659,900, titled METHOD OF HUB COMMUNICATION, filed Apr. 19, 2018, which is hereby incorporated by reference herein in its entirety.

Cloud System Hardware and Functional Modules

Figure 12:
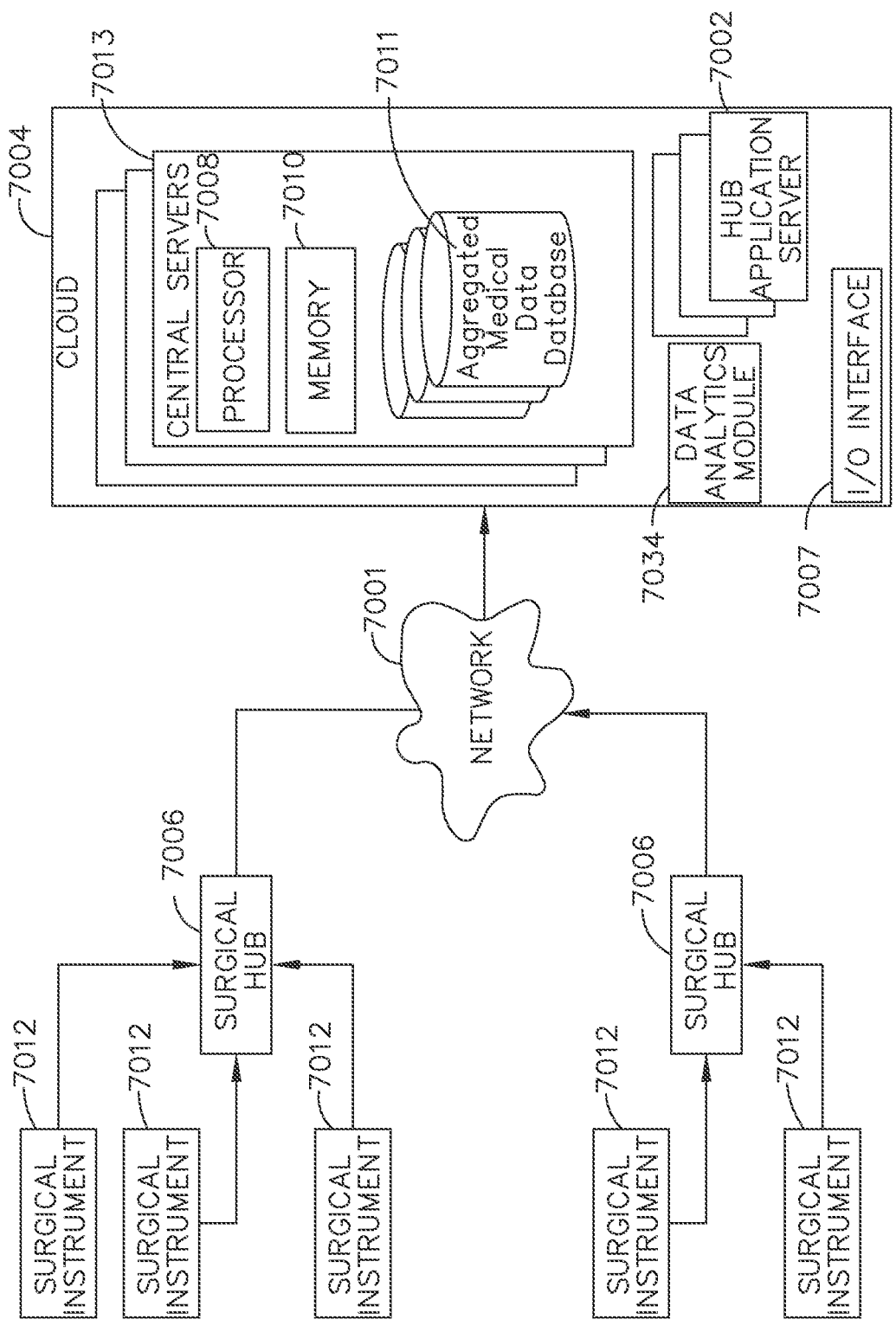
FIG. 12 is a block diagram of a cloud computing system comprising a plurality of smart surgical instruments coupled to surgical hubs that may connect to the cloud component of the cloud computing system, in accordance with at least one aspect of the present disclosure.

FIG. 12 is a block diagram of the computer-implemented interactive surgical system, in accordance with at least one aspect of the present disclosure. In one aspect, the computer-implemented interactive surgical system is configured to monitor and analyze data related to the operation of various surgical systems that include surgical hubs, surgical instruments, robotic devices and operating theaters or healthcare facilities. The computer-implemented interactive surgical system comprises a cloud-based analytics system. Although the cloud-based analytics system is described as a surgical system, it is not necessarily limited as such and could be a cloud-based medical system generally. As illustrated in FIG. 12, the cloud-based analytics system comprises a plurality of surgical instruments 7012 (may be the same or similar to instruments 112), a plurality of surgical hubs 7006 (may be the same or similar to hubs 106), and a surgical data network 7001 (may be the same or similar to network 201) to couple the surgical hubs 7006 to the cloud 7004 (may be the same or similar to cloud 204). Each of the plurality of surgical hubs 7006 is communicatively coupled to one or more surgical instruments 7012. The hubs 7006 are also communicatively coupled to the cloud 7004 of the computer-implemented interactive surgical system via the network 7001. The cloud 7004 is a remote centralized source of hardware and software for storing, manipulating, and communicating data generated based on the operation of various surgical systems. As shown in FIG. 12, access to the cloud 7004 is achieved via the network 7001, which may be the Internet or some other suitable computer network. Surgical hubs 7006 that are coupled to the cloud 7004 can be considered the client side of the cloud computing system (i.e., cloud-based analytics system). Surgical instruments 7012 are paired with the surgical hubs 7006 for control and implementation of various surgical procedures or operations as described herein.

In addition, surgical instruments 7012 may comprise transceivers for data transmission to and from their corresponding surgical hubs 7006 (which may also comprise transceivers). Combinations of surgical instruments 7012 and corresponding hubs 7006 may indicate particular locations, such as operating theaters in healthcare facilities (e.g., hospitals), for providing medical operations. For example, the memory of a surgical hub 7006 may store location data. As shown in FIG. 12, the cloud 7004 comprises central servers 7013 (which may be same or similar to remote server 113 in FIG. 1 and/or remote server 213 in FIG. 9), hub application servers 7002, data analytics modules 7034, and an input/output ("I/O") interface 7007. The central servers 7013 of the cloud 7004 collectively administer the cloud computing system, which includes monitoring requests by client surgical hubs 7006 and managing the processing capacity of the cloud 7004 for executing the requests. Each of the central servers 7013 comprises one or more processors 7008 coupled to suitable memory devices 7010 which can include volatile memory such as random-access memory (RAM) and non-volatile memory such as magnetic storage devices. The memory devices 7010 may comprise machine executable instructions that when executed cause the processors 7008 to execute the data analytics modules 7034 for the cloud-based data analysis, operations, recommendations and other operations described below. Moreover, the processors 7008 can execute the data analytics modules 7034 independently or in conjunction with hub applications independently executed by the hubs 7006. The central servers 7013 also comprise aggregated medical data databases 2212, which can reside in the memory 2210.

Based on connections to various surgical hubs 7006 via the network 7001, the cloud 7004 can aggregate data from specific data generated by various surgical instruments 7012 and their corresponding hubs 7006. Such aggregated data may be stored within the aggregated medical databases 7011 of the cloud 7004. In particular, the cloud 7004 may advantageously perform data analysis and operations on the aggregated data to yield insights and/or perform functions that individual hubs 7006 could not achieve on their own. To this end, as shown in FIG. 12, the cloud 7004 and the surgical hubs 7006 are communicatively coupled to transmit and receive information. The I/O interface 7007 is connected to the plurality of surgical hubs 7006 via the network 7001. In this way, the I/O interface 7007 can be configured to transfer information between the surgical hubs 7006 and the aggregated medical data databases 7012. Accordingly, the I/O interface 7007 may facilitate read/write operations of the cloud-based analytics system. Such read/write operations may be executed in response to requests from hubs 7006. These requests could be transmitted to the hubs 7006 through the hub applications. The I/O interface 7007 may include one or more high speed data ports, which may include universal serial bus (USB) ports, IEEE 1394 ports, as well as Wi-Fi and Bluetooth I/O interfaces for connecting the cloud 7004 to hubs 7006. The hub application servers 7002 of the cloud 7004 are configured to host and supply shared capabilities to software applications (e.g. hub applications) executed by surgical hubs 7006. For example, the hub application servers 7002 may manage requests made by the hub applications through the hubs 7006, control access to the aggregated medical data databases 7011, and perform load balancing. The data analytics modules 7034 are described in further detail with reference to FIG. 13.

The particular cloud computing system configuration described in the present disclosure is specifically designed to address various issues arising in the context of medical operations and procedures performed using medical devices, such as the surgical instruments 7012, 112. In particular, the surgical instruments 7012 may be digital surgical devices configured to interact with the cloud 7004 for implementing techniques to improve the performance of surgical operations. Various surgical instruments 7012 and/or surgical hubs 7006 may comprise touch controlled user interfaces such that clinicians may control aspects of interaction between the surgical instruments 7012 and the cloud 7004. Other suitable user interfaces for control such as auditory controlled user interfaces can also be used.

Figure 13:
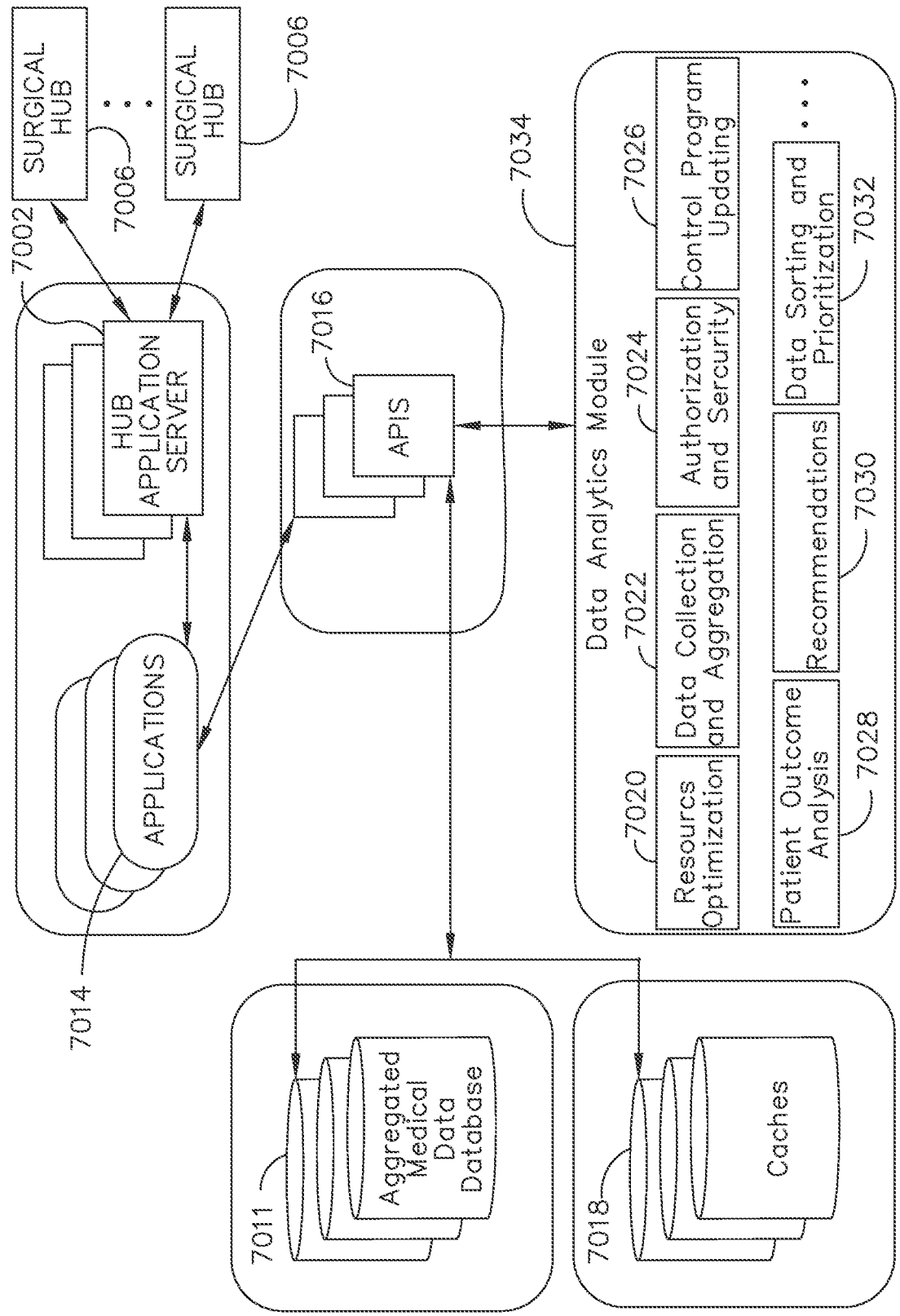
FIG. 13 is a functional module architecture of a cloud computing system, in accordance with at least one aspect of the present disclosure.

FIG. 13 is a block diagram which illustrates the functional architecture of the computer-implemented interactive surgical system, in accordance with at least one aspect of the present disclosure. The cloud-based analytics system includes a plurality of data analytics modules 7034 that may be executed by the processors 7008 of the cloud 7004 for providing data analytic solutions to problems specifically arising in the medical field. As shown in FIG. 13, the functions of the cloud-based data analytics modules 7034 may be assisted via hub applications 7014 hosted by the hub application servers 7002 that may be accessed on surgical hubs 7006. The cloud processors 7008 and hub applications 7014 may operate in conjunction to execute the data analytics modules 7034. Application program interfaces (APIs) 7016 define the set of protocols and routines corresponding to the hub applications 7014. Additionally, the APIs 7016 manage the storing and retrieval of data into and from the aggregated medical data databases 7011 for the operations of the applications 7014. The caches 7018 also store data (e.g., temporarily) and are coupled to the APIs 7016 for more efficient retrieval of data used by the applications 7014. The data analytics modules 7034 in FIG. 13 include modules for resource optimization 7020, data collection and aggregation 7022, authorization and security 7024, control program updating 7026, patient outcome analysis 7028, recommendations 7030, and data sorting and prioritization 7032. Other suitable data analytics modules could also be implemented by the cloud 7004, according to some aspects. In one aspect, the data analytics modules are used for specific recommendations based on analyzing trends, outcomes, and other data.

For example, the data collection and aggregation module 7022 could be used to generate self-describing data (e.g., metadata) including identification of notable features or configuration (e.g., trends), management of redundant data sets, and storage of the data in paired data sets which can be grouped by surgery but not necessarily keyed to actual surgical dates and surgeons. In particular, pair data sets generated from operations of surgical instruments 7012 can comprise applying a binary classification, e.g., a bleeding or a non-bleeding event. More generally, the binary classification may be characterized as either a desirable event (e.g., a successful surgical procedure) or an undesirable event (e.g., a misfired or misused surgical instrument 7012). The aggregated self-describing data may correspond to individual data received from various groups or subgroups of surgical hubs 7006. Accordingly, the data collection and aggregation module 7022 can generate aggregated metadata or other organized data based on raw data received from the surgical hubs 7006. To this end, the processors 7008 can be operationally coupled to the hub applications 7014 and aggregated medical data databases 7011 for executing the data analytics modules 7034. The data collection and aggregation module 7022 may store the aggregated organized data into the aggregated medical data databases 2212.

The resource optimization module 7020 can be configured to analyze this aggregated data to determine an optimal usage of resources for a particular or group of healthcare facilities. For example, the resource optimization module 7020 may determine an optimal order point of surgical stapling instruments 7012 for a group of healthcare facilities based on corresponding predicted demand of such instruments 7012. The resource optimization module 7020 might also assess the resource usage or other operational configurations of various healthcare facilities to determine whether resource usage could be improved. Similarly, the recommendations module 7030 can be configured to analyze aggregated organized data from the data collection and aggregation module 7022 to provide recommendations. For example, the recommendations module 7030 could recommend to healthcare facilities (e.g., medical service providers such as hospitals) that a particular surgical instrument 7012 should be upgraded to an improved version based on a higher than expected error rate, for example. Additionally, the recommendations module 7030 and/or resource optimization module 7020 could recommend better supply chain parameters such as product reorder points and provide suggestions of different surgical instrument 7012, uses thereof, or procedure steps to improve surgical outcomes. The healthcare facilities can receive such recommendations via corresponding surgical hubs 7006. More specific recommendations regarding parameters or configurations of various surgical instruments 7012 can also be provided. Hubs 7006 and/or surgical instruments 7012 each could also have display screens that display data or recommendations provided by the cloud 7004.

The patient outcome analysis module 7028 can analyze surgical outcomes associated with currently used operational parameters of surgical instruments 7012. The patient outcome analysis module 7028 may also analyze and assess other potential operational parameters. In this connection, the recommendations module 7030 could recommend using these other potential operational parameters based on yielding better surgical outcomes, such as better sealing or less bleeding. For example, the recommendations module 7030 could transmit recommendations to a surgical hub 7006 regarding when to use a particular cartridge for a corresponding stapling surgical instrument 7012. Thus, the cloud-based analytics system, while controlling for common variables, may be configured to analyze the large collection of raw data and to provide centralized recommendations over multiple healthcare facilities (advantageously determined based on aggregated data). For example, the cloud-based analytics system could analyze, evaluate, and/or aggregate data based on type of medical practice, type of patient, number of patients, geographic similarity between medical providers, which medical providers/facilities use similar types of instruments, etc., in a way that no single healthcare facility alone would be able to analyze independently.

The control program updating module 7026 could be configured to implement various surgical instrument 7012 recommendations when corresponding control programs are updated. For example, the patient outcome analysis module 7028 could identify correlations linking specific control parameters with successful (or unsuccessful) results. Such correlations may be addressed when updated control programs are transmitted to surgical instruments 7012 via the control program updating module 7026. Updates to instruments 7012 that are transmitted via a corresponding hub 7006 may incorporate aggregated performance data that was gathered and analyzed by the data collection and aggregation module 7022 of the cloud 7004. Additionally, the patient outcome analysis module 7028 and recommendations module 7030 could identify improved methods of using instruments 7012 based on aggregated performance data.

The cloud-based analytics system may include security features implemented by the cloud 7004. These security features may be managed by the authorization and security module 7024. Each surgical hub 7006 can have associated unique credentials such as username, password, and other suitable security credentials. These credentials could be stored in the memory 7010 and be associated with a permitted cloud access level. For example, based on providing accurate credentials, a surgical hub 7006 may be granted access to communicate with the cloud to a predetermined extent (e.g., may only engage in transmitting or receiving certain defined types of information). To this end, the aggregated medical data databases 7011 of the cloud 7004 may comprise a database of authorized credentials for verifying the accuracy of provided credentials. Different credentials may be associated with varying levels of permission for interaction with the cloud 7004, such as a predetermined access level for receiving the data analytics generated by the cloud 7004.

Furthermore, for security purposes, the cloud could maintain a database of hubs 7006, instruments 7012, and other devices that may comprise a "black list" of prohibited devices. In particular, a surgical hub 7006 listed on the black list may not be permitted to interact with the cloud, while surgical instruments 7012 listed on the black list may not have functional access to a corresponding hub 7006 and/or may be prevented from fully functioning when paired to its corresponding hub 7006. Additionally or alternatively, the cloud 7004 may flag instruments 7012 based on incompatibility or other specified criteria. In this manner, counterfeit medical devices and improper reuse of such devices throughout the cloud-based analytics system can be identified and addressed.

The surgical instruments 7012 may use wireless transceivers to transmit wireless signals that may represent, for example, authorization credentials for access to corresponding hubs 7006 and the cloud 7004. Wired transceivers may also be used to transmit signals. Such authorization credentials can be stored in the respective memory devices of the surgical instruments 7012. The authorization and security module 7024 can determine whether the authorization credentials are accurate or counterfeit. The authorization and security module 7024 may also dynamically generate authorization credentials for enhanced security. The credentials could also be encrypted, such as by using hash based encryption. Upon transmitting proper authorization, the surgical instruments 7012 may transmit a signal to the corresponding hubs 7006 and ultimately the cloud 7004 to indicate that the instruments 7012 are ready to obtain and transmit medical data. In response, the cloud 7004 may transition into a state enabled for receiving medical data for storage into the aggregated medical data databases 7011. This data transmission readiness could be indicated by a light indicator on the instruments 7012, for example. The cloud 7004 can also transmit signals to surgical instruments 7012 for updating their associated control programs. The cloud 7004 can transmit signals that are directed to a particular class of surgical instruments 7012 (e.g., electrosurgical instruments) so that software updates to control programs are only transmitted to the appropriate surgical instruments 7012. Moreover, the cloud 7004 could be used to implement system wide solutions to address local or global problems based on selective data transmission and authorization credentials. For example, if a group of surgical instruments 7012 are identified as having a common manufacturing defect, the cloud 7004 may change the authorization credentials corresponding to this group to implement an operational lockout of the group.

The cloud-based analytics system may allow for monitoring multiple healthcare facilities (e.g., medical facilities like hospitals) to determine improved practices and recommend changes (via the recommendations module 2030, for example) accordingly. Thus, the processors 7008 of the cloud 7004 can analyze data associated with an individual healthcare facility to identify the facility and aggregate the data with other data associated with other healthcare facilities in a group. Groups could be defined based on similar operating practices or geographical location, for example. In this way, the cloud 7004 may provide healthcare facility group wide analysis and recommendations. The cloud-based analytics system could also be used for enhanced situational awareness. For example, the processors 7008 may predictively model the effects of recommendations on the cost and effectiveness for a particular facility (relative to overall operations and/or various medical procedures). The cost and effectiveness associated with that particular facility can also be compared to a corresponding local zone of other facilities or any other comparable facilities.

The data sorting and prioritization module 7032 may prioritize and sort data based on criticality (e.g., the severity of a medical event associated with the data, unexpectedness, suspiciousness). This sorting and prioritization may be used in conjunction with the functions of the other data analytics modules 7034 described above to improve the cloud-based analytics and operations described herein. For example, the data sorting and prioritization module 7032 can assign a priority to the data analysis performed by the data collection and aggregation module 7022 and patient outcome analysis modules 7028. Different prioritization levels can result in particular responses from the cloud 7004 (corresponding to a level of urgency) such as escalation for an expedited response, special processing, exclusion from the aggregated medical data databases 7011, or other suitable responses. Moreover, if necessary, the cloud 7004 can transmit a request (e.g. a push message) through the hub application servers for additional data from corresponding surgical instruments 7012. The push message can result in a notification displayed on the corresponding hubs 7006 for requesting supporting or additional data. This push message may be required in situations in which the cloud detects a significant irregularity or outlier and the cloud cannot determine the cause of the irregularity. The central servers 7013 may be programmed to trigger this push message in certain significant circumstances, such as when data is determined to be different from an expected value beyond a predetermined threshold or when it appears security has been compromised, for example.

In various aspects, the surgical instrument(s) 7012 described above with reference to FIGS. 12 and 13, may be implemented as a circular powered stapling device 201800 (FIGS. 24-30), 201502 (FIGS. 31-33), 201532 (FIGS. 34-35), 201610 (FIGS. 36-40). Accordingly, the circular powered stapling device 201800 (FIGS. 24-30), 201502 (FIGS. 31-33), 201532 (FIGS. 34-35), 201610 (FIGS. 36-40) is configured to interface with the surgical hub 7006 and the network 2001, which is configured to interface with cloud 7004. Accordingly, the processing power provided by the central servers 7013 and the data analytics module 7034 are configured to process information (e.g., data and control) from the circular powered stapling device 201800 (FIGS. 24-30), 201502 (FIGS. 31-33), 201532 (FIGS. 34-35), 201610 (FIGS. 36-40). Additional details regarding the cloud analysis system can be found in U.S. Provisional Patent Application No. 62/659,900, titled METHOD OF HUB COMMUNICATION, filed Apr. 19, 2018, which is hereby incorporated by reference herein in its entirety.

Situational Awareness

Although an "intelligent" device including control algorithms that respond to sensed data can be an improvement over a "dumb" device that operates without accounting for sensed data, some sensed data can be incomplete or inconclusive when considered in isolation, i.e., without the context of the type of surgical procedure being performed or the type of tissue that is being operated on. Without knowing the procedural context (e.g., knowing the type of tissue being operated on or the type of procedure being performed), the control algorithm may control the modular device incorrectly or suboptimally given the particular context-free sensed data. For example, the optimal manner for a control algorithm to control a surgical instrument in response to a particular sensed parameter can vary according to the particular tissue type being operated on. This is due to the fact that different tissue types have different properties (e.g., resistance to tearing) and thus respond differently to actions taken by surgical instruments. Therefore, it may be desirable for a surgical instrument to take different actions even when the same measurement for a particular parameter is sensed. As one specific example, the optimal manner in which to control a surgical stapling and cutting instrument in response to the instrument sensing an unexpectedly high force to close its end effector will vary depending upon whether the tissue type is susceptible or resistant to tearing. For tissues that are susceptible to tearing, such as lung tissue, the instrument's control algorithm would optimally ramp down the motor in response to an unexpectedly high force to close to avoid tearing the tissue. For tissues that are resistant to tearing, such as stomach tissue, the instrument's control algorithm would optimally ramp up the motor in response to an unexpectedly high force to close to ensure that the end effector is clamped properly on the tissue. Without knowing whether lung or stomach tissue has been clamped, the control algorithm may make a suboptimal decision.

Figure 14:
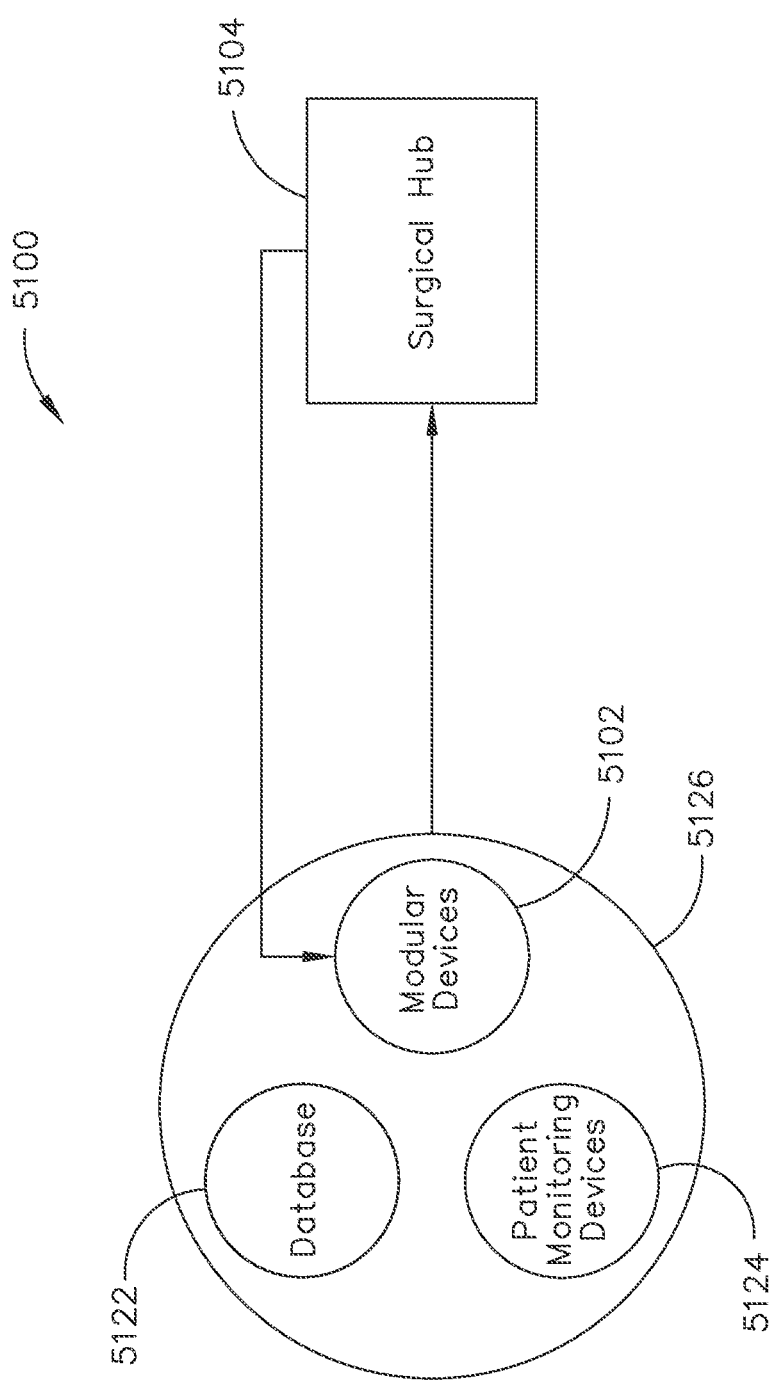
FIG. 14 illustrates a diagram of a situationally aware surgical system, in accordance with at least one aspect of the present disclosure.

One solution utilizes a surgical hub including a system that is configured to derive information about the surgical procedure being performed based on data received from various data sources and then control the paired modular devices accordingly. In other words, the surgical hub is configured to infer information about the surgical procedure from received data and then control the modular devices paired to the surgical hub based upon the inferred context of the surgical procedure. FIG. 14 illustrates a diagram of a situationally aware surgical system 5100, in accordance with at least one aspect of the present disclosure. In some exemplifications, the data sources 5126 include, for example, the modular devices 5102 (which can include sensors configured to detect parameters associated with the patient and/or the modular device itself), databases 5122 (e.g., an EMR database containing patient records), and patient monitoring devices 5124 (e.g., a blood pressure (BP) monitor and an electrocardiography (EKG) monitor).

A surgical hub 5104, which may be similar to the hub 106 in many respects, can be configured to derive the contextual information pertaining to the surgical procedure from the data based upon, for example, the particular combination(s) of received data or the particular order in which the data is received from the data sources 5126. The contextual information inferred from the received data can include, for example, the type of surgical procedure being performed, the particular step of the surgical procedure that the surgeon is performing, the type of tissue being operated on, or the body cavity that is the subject of the procedure. This ability by some aspects of the surgical hub 5104 to derive or infer information related to the surgical procedure from received data can be referred to as "situational awareness." In one exemplification, the surgical hub 5104 can incorporate a situational awareness system, which is the hardware and/or programming associated with the surgical hub 5104 that derives contextual information pertaining to the surgical procedure from the received data.

The situational awareness system of the surgical hub 5104 can be configured to derive the contextual information from the data received from the data sources 5126 in a variety of different ways. In one exemplification, the situational awareness system includes a pattern recognition system, or machine learning system (e.g., an artificial neural network), that has been trained on training data to correlate various inputs (e.g., data from databases 5122, patient monitoring devices 5124, and/or modular devices 5102) to corresponding contextual information regarding a surgical procedure. In other words, a machine learning system can be trained to accurately derive contextual information regarding a surgical procedure from the provided inputs. In another exemplification, the situational awareness system can include a lookup table storing pre-characterized contextual information regarding a surgical procedure in association with one or more inputs (or ranges of inputs) corresponding to the contextual information. In response to a query with one or more inputs, the lookup table can return the corresponding contextual information for the situational awareness system for controlling the modular devices 5102. In one exemplification, the contextual information received by the situational awareness system of the surgical hub 5104 is associated with a particular control adjustment or set of control adjustments for one or more modular devices 5102. In another exemplification, the situational awareness system includes a further machine learning system, lookup table, or other such system, which generates or retrieves one or more control adjustments for one or more modular devices 5102 when provided the contextual information as input.

A surgical hub 5104 incorporating a situational awareness system provides a number of benefits for the surgical system 5100. One benefit includes improving the interpretation of sensed and collected data, which would in turn improve the processing accuracy and/or the usage of the data during the course of a surgical procedure. To return to a previous example, a situationally aware surgical hub 5104 could determine what type of tissue was being operated on; therefore, when an unexpectedly high force to close the surgical instrument's end effector is detected, the situationally aware surgical hub 5104 could correctly ramp up or ramp down the motor of the surgical instrument for the type of tissue.

As another example, the type of tissue being operated can affect the adjustments that are made to the compression rate and load thresholds of a surgical stapling and cutting instrument for a particular tissue gap measurement. A situationally aware surgical hub 5104 could infer whether a surgical procedure being performed is a thoracic or an abdominal procedure, allowing the surgical hub 5104 to determine whether the tissue clamped by an end effector of the surgical stapling and cutting instrument is lung (for a thoracic procedure) or stomach (for an abdominal procedure) tissue. The surgical hub 5104 could then adjust the compression rate and load thresholds of the surgical stapling and cutting instrument appropriately for the type of tissue.

As yet another example, the type of body cavity being operated in during an insufflation procedure can affect the function of a smoke evacuator. A situationally aware surgical hub 5104 could determine whether the surgical site is under pressure (by determining that the surgical procedure is utilizing insufflation) and determine the procedure type. As a procedure type is generally performed in a specific body cavity, the surgical hub 5104 could then control the motor rate of the smoke evacuator appropriately for the body cavity being operated in. Thus, a situationally aware surgical hub 5104 could provide a consistent amount of smoke evacuation for both thoracic and abdominal procedures.

As yet another example, the type of procedure being performed can affect the optimal energy level for an ultrasonic surgical instrument or radio frequency (RF) electrosurgical instrument to operate at. Arthroscopic procedures, for example, require higher energy levels because the end effector of the ultrasonic surgical instrument or RF electrosurgical instrument is immersed in fluid. A situationally aware surgical hub 5104 could determine whether the surgical procedure is an arthroscopic procedure. The surgical hub 5104 could then adjust the RF power level or the ultrasonic amplitude of the generator (i.e., "energy level") to compensate for the fluid filled environment. Relatedly, the type of tissue being operated on can affect the optimal energy level for an ultrasonic surgical instrument or RF electrosurgical instrument to operate at. A situationally aware surgical hub 5104 could determine what type of surgical procedure is being performed and then customize the energy level for the ultrasonic surgical instrument or RF electrosurgical instrument, respectively, according to the expected tissue profile for the surgical procedure. Furthermore, a situationally aware surgical hub 5104 can be configured to adjust the energy level for the ultrasonic surgical instrument or RF electrosurgical instrument throughout the course of a surgical procedure, rather than just on a procedure-by-procedure basis. A situationally aware surgical hub 5104 could determine what step of the surgical procedure is being performed or will subsequently be performed and then update the control algorithms for the generator and/or ultrasonic surgical instrument or RF electrosurgical instrument to set the energy level at a value appropriate for the expected tissue type according to the surgical procedure step.

As yet another example, data can be drawn from additional data sources 5126 to improve the conclusions that the surgical hub 5104 draws from one data source 5126. A situationally aware surgical hub 5104 could augment data that it receives from the modular devices 5102 with contextual information that it has built up regarding the surgical procedure from other data sources 5126. For example, a situationally aware surgical hub 5104 can be configured to determine whether hemostasis has occurred (i.e., whether bleeding at a surgical site has stopped) according to video or image data received from a medical imaging device. However, in some cases the video or image data can be inconclusive. Therefore, in one exemplification, the surgical hub 5104 can be further configured to compare a physiologic measurement (e.g., blood pressure sensed by a BP monitor communicably connected to the surgical hub 5104) with the visual or image data of hemostasis (e.g., from a medical imaging device 124 (FIG. 2) communicably coupled to the surgical hub 5104) to make a determination on the integrity of the staple line or tissue weld. In other words, the situational awareness system of the surgical hub 5104 can consider the physiological measurement data to provide additional context in analyzing the visualization data. The additional context can be useful when the visualization data may be inconclusive or incomplete on its own.

Another benefit includes proactively and automatically controlling the paired modular devices 5102 according to the particular step of the surgical procedure that is being performed to reduce the number of times that medical personnel are required to interact with or control the surgical system 5100 during the course of a surgical procedure. For example, a situationally aware surgical hub 5104 could proactively activate the generator to which an RF electrosurgical instrument is connected if it determines that a subsequent step of the procedure requires the use of the instrument. Proactively activating the energy source allows the instrument to be ready for use a soon as the preceding step of the procedure is completed.

As another example, a situationally aware surgical hub 5104 could determine whether the current or subsequent step of the surgical procedure requires a different view or degree of magnification on the display according to the feature(s) at the surgical site that the surgeon is expected to need to view. The surgical hub 5104 could then proactively change the displayed view (supplied by, e.g., a medical imaging device for the visualization system 108) accordingly so that the display automatically adjusts throughout the surgical procedure.

As yet another example, a situationally aware surgical hub 5104 could determine which step of the surgical procedure is being performed or will subsequently be performed and whether particular data or comparisons between data will be required for that step of the surgical procedure. The surgical hub 5104 can be configured to automatically call up data screens based upon the step of the surgical procedure being performed, without waiting for the surgeon to ask for the particular information.

Another benefit includes checking for errors during the setup of the surgical procedure or during the course of the surgical procedure. For example, a situationally aware surgical hub 5104 could determine whether the operating theater is setup properly or optimally for the surgical procedure to be performed. The surgical hub 5104 can be configured to determine the type of surgical procedure being performed, retrieve the corresponding checklists, product location, or setup needs (e.g., from a memory), and then compare the current operating theater layout to the standard layout for the type of surgical procedure that the surgical hub 5104 determines is being performed. In one exemplification, the surgical hub 5104 can be configured to compare the list of items for the procedure scanned by a suitable scanner for example and/or a list of devices paired with the surgical hub 5104 to a recommended or anticipated manifest of items and/or devices for the given surgical procedure. If there are any discontinuities between the lists, the surgical hub 5104 can be configured to provide an alert indicating that a particular modular device 5102, patient monitoring device 5124, and/or other surgical item is missing. In one exemplification, the surgical hub 5104 can be configured to determine the relative distance or position of the modular devices 5102 and patient monitoring devices 5124 via proximity sensors, for example. The surgical hub 5104 can compare the relative positions of the devices to a recommended or anticipated layout for the particular surgical procedure. If there are any discontinuities between the layouts, the surgical hub 5104 can be configured to provide an alert indicating that the current layout for the surgical procedure deviates from the recommended layout.

As another example, a situationally aware surgical hub 5104 could determine whether the surgeon (or other medical personnel) was making an error or otherwise deviating from the expected course of action during the course of a surgical procedure. For example, the surgical hub 5104 can be configured to determine the type of surgical procedure being performed, retrieve the corresponding list of steps or order of equipment usage (e.g., from a memory), and then compare the steps being performed or the equipment being used during the course of the surgical procedure to the expected steps or equipment for the type of surgical procedure that the surgical hub 5104 determined is being performed. In one exemplification, the surgical hub 5104 can be configured to provide an alert indicating that an unexpected action is being performed or an unexpected device is being utilized at the particular step in the surgical procedure.

Overall, the situational awareness system for the surgical hub 5104 improves surgical procedure outcomes by adjusting the surgical instruments (and other modular devices 5102) for the particular context of each surgical procedure (such as adjusting to different tissue types) and validating actions during a surgical procedure. The situational awareness system also improves surgeons' efficiency in performing surgical procedures by automatically suggesting next steps, providing data, and adjusting displays and other modular devices 5102 in the surgical theater according to the specific context of the procedure.

In one aspect, as described hereinbelow with reference to FIGS. 24-40, the modular device 5102 is implemented as a circular powered stapling device 201800 (FIGS. 24-30), 201502 (FIGS. 31-33), 201532 (FIGS. 34-35), 201610 (FIGS. 36-40). Accordingly, the modular device 5102 implemented as a circular powered stapling device 201800 (FIGS. 24-30), 201502 (FIGS. 31-33), 201532 (FIGS. 34-35), 201610 (FIGS. 36-40) is configured to operate as a data source 5126 and to interact with the database 5122 and patient monitoring devices 5124. The modular device 5102 implemented as a circular powered stapling device 201800 (FIGS. 24-30), 201502 (FIGS. 31-33), 201532 (FIGS. 34-35), 201610 (FIGS. 36-40) is further configured to interact with the surgical hub 5104 to provide information (e.g., data and control) to the surgical hub 5104 and receive information (e.g., data and control) from the surgical hub 5104.

Figure 15:
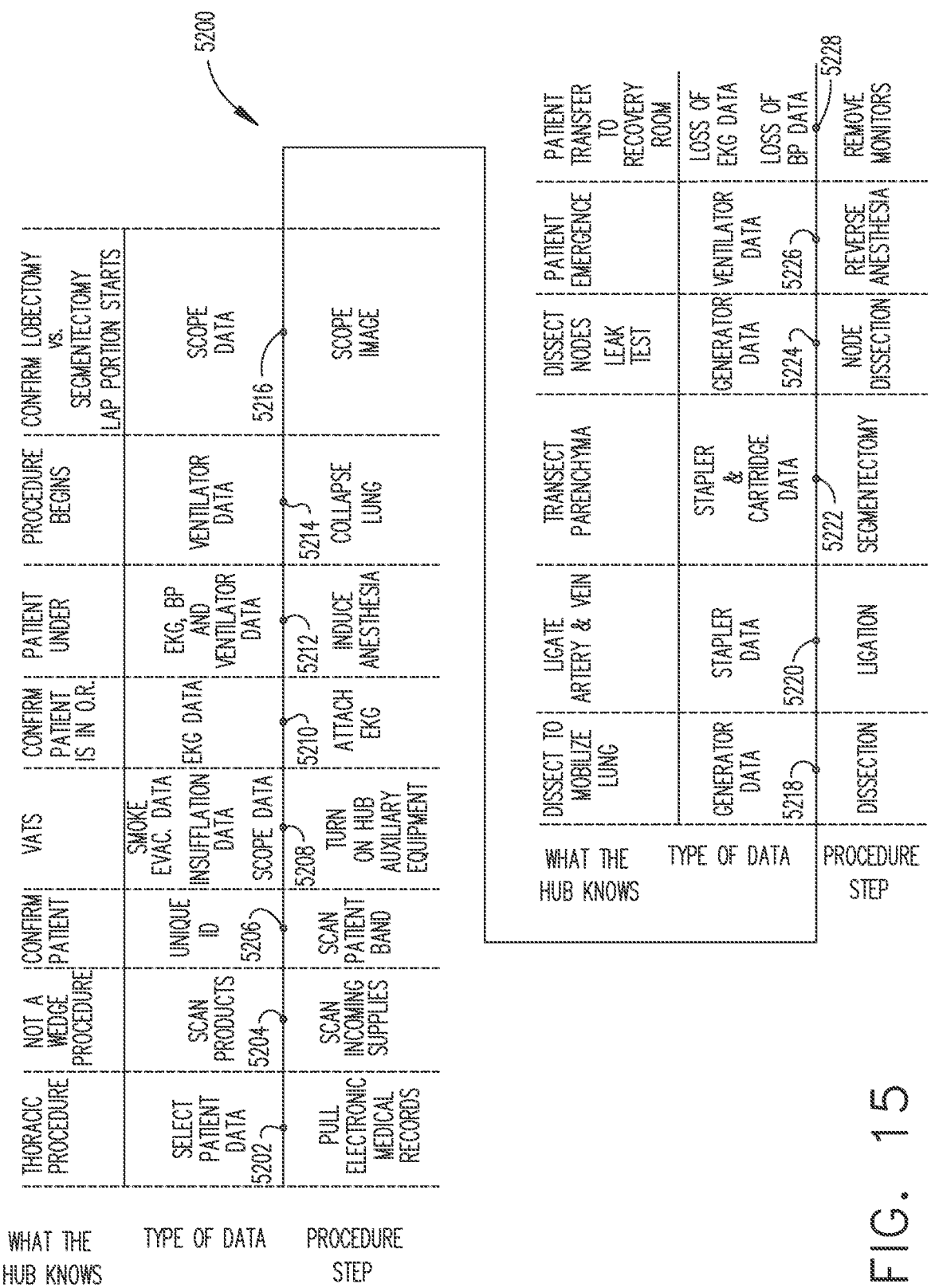
FIG. 15 is a timeline depicting situational awareness of a surgical hub, in accordance with at least one aspect of the present disclosure.

Referring now to FIG. 15, a timeline 5200 depicting situational awareness of a hub, such as the surgical hub 106 or 206 (FIGS. 1-11), for example, is depicted. The timeline 5200 is an illustrative surgical procedure and the contextual information that the surgical hub 106, 206 can derive from the data received from the data sources at each step in the surgical procedure. The timeline 5200 depicts the typical steps that would be taken by the nurses, surgeons, and other medical personnel during the course of a lung segmentectomy procedure, beginning with setting up the operating theater and ending with transferring the patient to a postoperative recovery room.

The situationally aware surgical hub 106, 206 receives data from the data sources throughout the course of the surgical procedure, including data generated each time medical personnel utilize a modular device that is paired with the surgical hub 106, 206. The surgical hub 106, 206 can receive this data from the paired modular devices and other data sources and continually derive inferences (i.e., contextual information) about the ongoing procedure as new data is received, such as which step of the procedure is being performed at any given time. The situational awareness system of the surgical hub 106, 206 is able to, for example, record data pertaining to the procedure for generating reports, verify the steps being taken by the medical personnel, provide data or prompts (e.g., via a display screen) that may be pertinent for the particular procedural step, adjust modular devices based on the context (e.g., activate monitors, adjust the field of view (FOV) of the medical imaging device, or change the energy level of an ultrasonic surgical instrument or RF electrosurgical instrument), and take any other such action described above.

As the first step 5202 in this illustrative procedure, the hospital staff members retrieve the patient's EMR from the hospital's EMR database. Based on select patient data in the EMR, the surgical hub 106, 206 determines that the procedure to be performed is a thoracic procedure.

Second step 5204, the staff members scan the incoming medical supplies for the procedure. The surgical hub 106, 206 cross-references the scanned supplies with a list of supplies that are utilized in various types of procedures and confirms that the mix of supplies corresponds to a thoracic procedure. Further, the surgical hub 106, 206 is also able to determine that the procedure is not a wedge procedure (because the incoming supplies either lack certain supplies that are necessary for a thoracic wedge procedure or do not otherwise correspond to a thoracic wedge procedure).

Third step 5206, the medical personnel scan the patient band via a scanner that is communicably connected to the surgical hub 106, 206. The surgical hub 106, 206 can then confirm the patient's identity based on the scanned data.

Fourth step 5208, the medical staff turns on the auxiliary equipment. The auxiliary equipment being utilized can vary according to the type of surgical procedure and the techniques to be used by the surgeon, but in this illustrative case they include a smoke evacuator, insufflator, and medical imaging device. When activated, the auxiliary equipment that are modular devices can automatically pair with the surgical hub 106, 206 that is located within a particular vicinity of the modular devices as part of their initialization process. The surgical hub 106, 206 can then derive contextual information about the surgical procedure by detecting the types of modular devices that pair with it during this pre-operative or initialization phase. In this particular example, the surgical hub 106, 206 determines that the surgical procedure is a VATS procedure based on this particular combination of paired modular devices. Based on the combination of the data from the patient's EMR, the list of medical supplies to be used in the procedure, and the type of modular devices that connect to the hub, the surgical hub 106, 206 can generally infer the specific procedure that the surgical team will be performing. Once the surgical hub 106, 206 knows what specific procedure is being performed, the surgical hub 106, 206 can then retrieve the steps of that procedure from a memory or from the cloud and then cross-reference the data it subsequently receives from the connected data sources (e.g., modular devices and patient monitoring devices) to infer what step of the surgical procedure the surgical team is performing.

Fifth step 5210, the staff members attach the EKG electrodes and other patient monitoring devices to the patient. The EKG electrodes and other patient monitoring devices are able to pair with the surgical hub 106, 206. As the surgical hub 106, 206 begins receiving data from the patient monitoring devices, the surgical hub 106, 206 thus confirms that the patient is in the operating theater.

Sixth step 5212, the medical personnel induce anesthesia in the patient. The surgical hub 106, 206 can infer that the patient is under anesthesia based on data from the modular devices and/or patient monitoring devices, including EKG data, blood pressure data, ventilator data, or combinations thereof, for example. Upon completion of the sixth step 5212, the pre-operative portion of the lung segmentectomy procedure is completed and the operative portion begins.

Seventh step 5214, the patient's lung that is being operated on is collapsed (while ventilation is switched to the contralateral lung). The surgical hub 106, 206 can infer from the ventilator data that the patient's lung has been collapsed, for example. The surgical hub 106, 206 can infer that the operative portion of the procedure has commenced as it can compare the detection of the patient's lung collapsing to the expected steps of the procedure (which can be accessed or retrieved previously) and thereby determine that collapsing the lung is the first operative step in this particular procedure.

Eighth step 5216, the medical imaging device (e.g., a scope) is inserted and video from the medical imaging device is initiated. The surgical hub 106, 206 receives the medical imaging device data (i.e., video or image data) through its connection to the medical imaging device. Upon receipt of the medical imaging device data, the surgical hub 106, 206 can determine that the laparoscopic portion of the surgical procedure has commenced. Further, the surgical hub 106, 206 can determine that the particular procedure being performed is a segmentectomy, as opposed to a lobectomy (note that a wedge procedure has already been discounted by the surgical hub 106, 206 based on data received at the second step 5204 of the procedure). The data from the medical imaging device 124 (FIG. 2) can be utilized to determine contextual information regarding the type of procedure being performed in a number of different ways, including by determining the angle at which the medical imaging device is oriented with respect to the visualization of the patient's anatomy, monitoring the number or medical imaging devices being utilized (i.e., that are activated and paired with the surgical hub 106, 206), and monitoring the types of visualization devices utilized. For example, one technique for performing a VATS lobectomy places the camera in the lower anterior corner of the patient's chest cavity above the diaphragm, whereas one technique for performing a VATS segmentectomy places the camera in an anterior intercostal position relative to the segmental fissure. Using pattern recognition or machine learning techniques, for example, the situational awareness system can be trained to recognize the positioning of the medical imaging device according to the visualization of the patient's anatomy. As another example, one technique for performing a VATS lobectomy utilizes a single medical imaging device, whereas another technique for performing a VATS segmentectomy utilizes multiple cameras. As yet another example, one technique for performing a VATS segmentectomy utilizes an infrared light source (which can be communicably coupled to the surgical hub as part of the visualization system) to visualize the segmental fissure, which is not utilized in a VATS lobectomy. By tracking any or all of this data from the medical imaging device, the surgical hub 106, 206 can thereby determine the specific type of surgical procedure being performed and/or the technique being used for a particular type of surgical procedure.

Ninth step 5218, the surgical team begins the dissection step of the procedure. The surgical hub 106, 206 can infer that the surgeon is in the process of dissecting to mobilize the patient's lung because it receives data from the RF or ultrasonic generator indicating that an energy instrument is being fired. The surgical hub 106, 206 can cross-reference the received data with the retrieved steps of the surgical procedure to determine that an energy instrument being fired at this point in the process (i.e., after the completion of the previously discussed steps of the procedure) corresponds to the dissection step. In certain instances, the energy instrument can be an energy tool mounted to a robotic arm of a robotic surgical system.

Tenth step 5220, the surgical team proceeds to the ligation step of the procedure. The surgical hub 106, 206 can infer that the surgeon is ligating arteries and veins because it receives data from the surgical stapling and cutting instrument indicating that the instrument is being fired. Similarly to the prior step, the surgical hub 106, 206 can derive this inference by cross-referencing the receipt of data from the surgical stapling and cutting instrument with the retrieved steps in the process. In certain instances, the surgical instrument can be a surgical tool mounted to a robotic arm of a robotic surgical system.

Eleventh step 5222, the segmentectomy portion of the procedure is performed. The surgical hub 106, 206 can infer that the surgeon is transecting the parenchyma based on data from the surgical stapling and cutting instrument, including data from its cartridge. The cartridge data can correspond to the size or type of staple being fired by the instrument, for example. As different types of staples are utilized for different types of tissues, the cartridge data can thus indicate the type of tissue being stapled and/or transected. In this case, the type of staple being fired is utilized for parenchyma (or other similar tissue types), which allows the surgical hub 106, 206 to infer that the segmentectomy portion of the procedure is being performed.

Twelfth step 5224, the node dissection step is then performed. The surgical hub 106, 206 can infer that the surgical team is dissecting the node and performing a leak test based on data received from the generator indicating that an RF or ultrasonic instrument is being fired. For this particular procedure, an RF or ultrasonic instrument being utilized after parenchyma was transected corresponds to the node dissection step, which allows the surgical hub 106, 206 to make this inference. It should be noted that surgeons regularly switch back and forth between surgical stapling/cutting instruments and surgical energy (i.e., RF or ultrasonic) instruments depending upon the particular step in the procedure because different instruments are better adapted for particular tasks. Therefore, the particular sequence in which the stapling/cutting instruments and surgical energy instruments are used can indicate what step of the procedure the surgeon is performing. Moreover, in certain instances, robotic tools can be utilized for one or more steps in a surgical procedure and/or handheld surgical instruments can be utilized for one or more steps in the surgical procedure. The surgeon(s) can alternate between robotic tools and handheld surgical instruments and/or can use the devices concurrently, for example. Upon completion of the twelfth step 5224, the incisions are closed up and the post-operative portion of the procedure begins.

Thirteenth step 5226, the patient's anesthesia is reversed. The surgical hub 106, 206 can infer that the patient is emerging from the anesthesia based on the ventilator data (i.e., the patient's breathing rate begins increasing), for example.

Lastly, the fourteenth step 5228 is that the medical personnel remove the various patient monitoring devices from the patient. The surgical hub 106, 206 can thus infer that the patient is being transferred to a recovery room when the hub loses EKG, BP, and other data from the patient monitoring devices. As can be seen from the description of this illustrative procedure, the surgical hub 106, 206 can determine or infer when each step of a given surgical procedure is taking place according to data received from the various data sources that are communicably coupled to the surgical hub 106, 206.

In various aspects, the circular powered stapling device 201800 (FIGS. 24-30), 201502 (FIGS. 31-33), 201532 (FIGS. 34-35), 201610 (FIGS. 36-40) is configured to operate in a situational awareness in a hub environment, such as the surgical hub 106 or 206 (FIGS. 1-11), for example, as depicted by the timeline 5200. Situational awareness is further described in U.S. Provisional Patent Application Ser. No. 62/659,900, titled METHOD OF HUB COMMUNICATION, filed Apr. 19, 2018, which is herein incorporated by reference in its entirety. In certain instances, operation of a robotic surgical system, including the various robotic surgical systems disclosed herein, for example, can be controlled by the hub 106, 206 based on its situational awareness and/or feedback from the components thereof and/or based on information from the cloud 104.

Surgical Instrument Hardware

Figure 16:
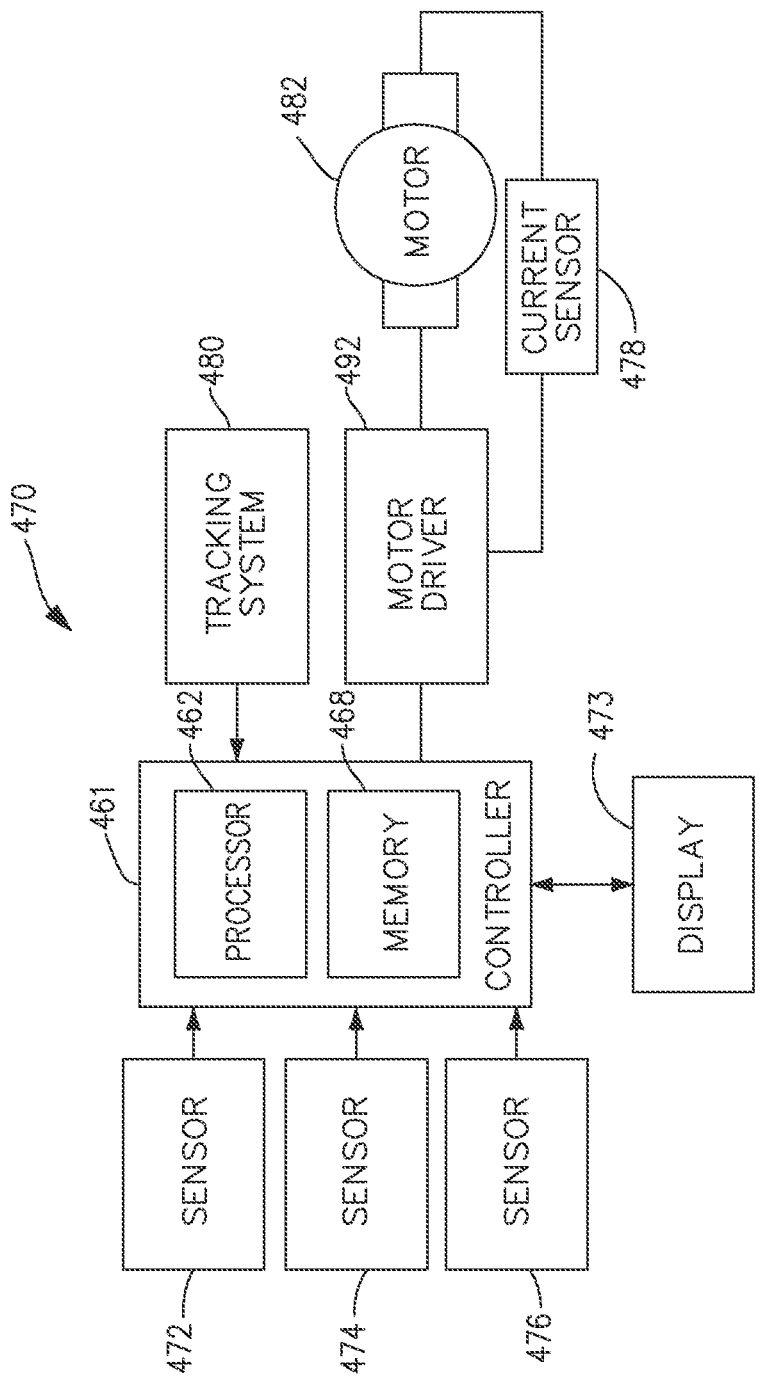
FIG. 16 illustrates a logic diagram of a control system of a surgical instrument or tool, in accordance with at least one aspect of the present disclosure.

FIG. 16 illustrates a logic diagram of a control system 470 of a surgical instrument or tool in accordance with one or more aspects of the present disclosure. The system 470 comprises a control circuit. The control circuit includes a microcontroller 461 comprising a processor 462 and a memory 468. One or more of sensors 472, 474, 476, for example, provide real-time feedback to the processor 462. A motor 482, driven by a motor driver 492, operably couples a longitudinally movable displacement member to drive the knife element, trocar, or anvil of a powered circular stapling device. A tracking system 480 is configured to determine the position of the longitudinally movable displacement member. The position information is provided to the processor 462, which can be programmed or configured to determine the position of the longitudinally movable drive member as well as the position of a firing member, firing bar, and knife element. Additional motors may be provided at the tool driver interface to control knife firing, closure tube travel, shaft rotation, and articulation. A display 473 displays a variety of operating conditions of the instruments and may include touch screen functionality for data input. Information displayed on the display 473 may be overlaid with images acquired via endoscopic imaging modules.

In one aspect, the microcontroller 461 may be any single-core or multicore processor such as those known under the trade name ARM Cortex by Texas Instruments. In one aspect, the main microcontroller 461 may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle SRAM, and internal ROM loaded with StellarisWare® software, a 2 KB EEPROM, one or more PWM modules, one or more QEI analogs, and/or one or more 12-bit ADCs with 12 analog input channels, details of which are available for the product datasheet.

In one aspect, the microcontroller 461 may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The microcontroller 461 may be programmed to perform various functions such as precise control over the speed and position of the knife and articulation systems. In one aspect, the microcontroller 461 includes a processor 462 and a memory 468. The electric motor 482 may be a brushed direct current (DC) motor with a gearbox and mechanical links to an articulation or knife system. In one aspect, a motor driver 492 may be an A3941 available from Allegro Microsystems, Inc. Other motor drivers may be readily substituted for use in the tracking system 480 comprising an absolute positioning system. A detailed description of an absolute positioning system is described in U.S. Patent Application Publication No. 2017/0296213, titled SYSTEMS AND METHODS FOR CONTROLLING A SURGICAL STAPLING AND CUTTING INSTRUMENT, which published on Oct. 19, 2017, which is herein incorporated by reference in its entirety.

The microcontroller 461 may be programmed to provide precise control over the speed and position of displacement members and articulation systems. The microcontroller 461 may be configured to compute a response in the software of the microcontroller 461. The computed response is compared to a measured response of the actual system to obtain an "observed" response, which is used for actual feedback decisions. The observed response is a favorable, tuned value that balances the smooth, continuous nature of the simulated response with the measured response, which can detect outside influences on the system.

In one aspect, the motor 482 may be controlled by the motor driver 492 and can be employed by the firing system of the surgical instrument or tool. In various forms, the motor 482 may be a brushed DC driving motor having a maximum rotational speed of approximately 25,000 RPM. In other arrangements, the motor 482 may include a brushless motor, a cordless motor, a synchronous motor, a stepper motor, or any other suitable electric motor. The motor driver 492 may comprise an H-bridge driver comprising field-effect transistors (FETs), for example. The motor 482 can be powered by a power assembly releasably mounted to the handle assembly or tool housing for supplying control power to the surgical instrument or tool. The power assembly may comprise a battery which may include a number of battery cells connected in series that can be used as the power source to power the surgical instrument or tool. In certain circumstances, the battery cells of the power assembly may be replaceable and/or rechargeable. In at least one example, the battery cells can be lithium-ion batteries which can be couplable to and separable from the power assembly.

The motor driver 492 may be an A3941 available from Allegro Microsystems, Inc. The A3941 492 is a full-bridge controller for use with external N-channel power metal-oxide semiconductor field-effect transistors (MOSFETs) specifically designed for inductive loads, such as brush DC motors. The driver 492 comprises a unique charge pump regulator that provides full (>10 V) gate drive for battery voltages down to 7 V and allows the A3941 to operate with a reduced gate drive, down to 5.5 V. A bootstrap capacitor may be employed to provide the above battery supply voltage required for N-channel MOSFETs. An internal charge pump for the high-side drive allows DC (100% duty cycle) operation. The full bridge can be driven in fast or slow decay modes using diode or synchronous rectification. In the slow decay mode, current recirculation can be through the high-side or the lowside FETs. The power FETs are protected from shoot-through by resistor-adjustable dead time. Integrated diagnostics provide indications of undervoltage, overtemperature, and power bridge faults and can be configured to protect the power MOSFETs under most short circuit conditions. Other motor drivers may be readily substituted for use in the tracking system 480 comprising an absolute positioning system.

The tracking system 480 comprises a controlled motor drive circuit arrangement comprising a position sensor 472 according to one aspect of this disclosure. The position sensor 472 for an absolute positioning system provides a unique position signal corresponding to the location of a displacement member. In one aspect, the displacement member represents a longitudinally movable drive member comprising a rack of drive teeth for meshing engagement with a corresponding drive gear of a gear reducer assembly. In other aspects, the displacement member represents the firing member, which could be adapted and configured to include a rack of drive teeth. In yet another aspect, the displacement member represents a firing bar or the knife, each of which can be adapted and configured to include a rack of drive teeth. Accordingly, as used herein, the term displacement member is used generically to refer to any movable member of the surgical instrument or tool such as the drive member, the firing member, the firing bar, the knife, trocar or anvil of a powered circular stapling device, or any element that can be displaced. In one aspect, the longitudinally movable drive member is coupled to the firing member, the firing bar, and the knife. Accordingly, the absolute positioning system can, in effect, track the linear displacement of the knife by tracking the linear displacement of the longitudinally movable drive member. In various other aspects, the displacement member may be coupled to any position sensor 472 suitable for measuring linear displacement. Thus, the longitudinally movable drive member, the firing member, the firing bar, or the knife, or combinations thereof, may be coupled to any suitable linear displacement sensor. Linear displacement sensors may include contact or non-contact displacement sensors. Linear displacement sensors may comprise linear variable differential transformers (LVDT), differential variable reluctance transducers (DVRT), a slide potentiometer, a magnetic sensing system comprising a movable magnet and a series of linearly arranged Hall effect sensors, a magnetic sensing system comprising a fixed magnet and a series of movable, linearly arranged Hall effect sensors, an optical sensing system comprising a movable light source and a series of linearly arranged photo diodes or photo detectors, an optical sensing system comprising a fixed light source and a series of movable linearly, arranged photo diodes or photo detectors, or any combination thereof.

The electric motor 482 can include a rotatable shaft that operably interfaces with a gear assembly that is mounted in meshing engagement with a set, or rack, of drive teeth on the displacement member. A sensor element may be operably coupled to a gear assembly such that a single revolution of the position sensor 472 element corresponds to some linear longitudinal translation of the displacement member. An arrangement of gearing and sensors can be connected to the linear actuator, via a rack and pinion arrangement, or a rotary actuator, via a spur gear or other connection. A power source supplies power to the absolute positioning system and an output indicator may display the output of the absolute positioning system. The displacement member represents the longitudinally movable drive member comprising a rack of drive teeth formed thereon for meshing engagement with a corresponding drive gear of the gear reducer assembly. The displacement member represents the longitudinally movable firing member, firing bar, knife, or combinations thereof.

A single revolution of the sensor element associated with the position sensor 472 is equivalent to a longitudinal linear displacement d1 of the of the displacement member, where d1 is the longitudinal linear distance that the displacement member moves from point "a" to point "b" after a single revolution of the sensor element coupled to the displacement member. The sensor arrangement may be connected via a gear reduction that results in the position sensor 472 completing one or more revolutions for the full stroke of the displacement member. The position sensor 472 may complete multiple revolutions for the full stroke of the displacement member.

A series of switches, where n is an integer greater than one, may be employed alone or in combination with a gear reduction to provide a unique position signal for more than one revolution of the position sensor 472. The state of the switches are fed back to the microcontroller 461 that applies logic to determine a unique position signal corresponding to the longitudinal linear displacement d1+d2+ . . . dn of the displacement member. The output of the position sensor 472 is provided to the microcontroller 461. The position sensor 472 of the sensor arrangement may comprise a magnetic sensor, an analog rotary sensor like a potentiometer, or an array of analog Hall-effect elements, which output a unique combination of position signals or values.

The position sensor 472 may comprise any number of magnetic sensing elements, such as, for example, magnetic sensors classified according to whether they measure the total magnetic field or the vector components of the magnetic field. The techniques used to produce both types of magnetic sensors encompass many aspects of physics and electronics. The technologies used for magnetic field sensing include search coil, fluxgate, optically pumped, nuclear precession, SQUID, Hall-effect, anisotropic magnetoresistance, giant magnetoresistance, magnetic tunnel junctions, giant magnetoimpedance, magnetostrictive/piezoelectric composites, magnetodiode, magnetotransistor, fiber-optic, magneto-optic, and microelectromechanical systems-based magnetic sensors, among others.

In one aspect, the position sensor 472 for the tracking system 480 comprising an absolute positioning system comprises a magnetic rotary absolute positioning system. The position sensor 472 may be implemented as an AS5055EQFT single-chip magnetic rotary position sensor available from Austria Microsystems, AG. The position sensor 472 is interfaced with the microcontroller 461 to provide an absolute positioning system. The position sensor 472 is a low-voltage and low-power component and includes four Hall-effect elements in an area of the position sensor 472 that is located above a magnet. A high-resolution ADC and a smart power management controller are also provided on the chip. A coordinate rotation digital computer (CORDIC) processor, also known as the digit-by-digit method and Volder's algorithm, is provided to implement a simple and efficient algorithm to calculate hyperbolic and trigonometric functions that require only addition, subtraction, bitshift, and table lookup operations. The angle position, alarm bits, and magnetic field information are transmitted over a standard serial communication interface, such as a serial peripheral interface (SPI) interface, to the microcontroller 461. The position sensor 472 provides 12 or 14 bits of resolution. The position sensor 472 may be an AS5055 chip provided in a small QFN 16-pin 4×4×0.85 mm package.

The tracking system 480 comprising an absolute positioning system may comprise and/or be programmed to implement a feedback controller, such as a PID, state feedback, and adaptive controller. A power source converts the signal from the feedback controller into a physical input to the system: in this case the voltage. Other examples include a PWM of the voltage, current, and force. Other sensor(s) may be provided to measure physical parameters of the physical system in addition to the position measured by the position sensor 472. In some aspects, the other sensor(s) can include sensor arrangements such as those described in U.S. Pat. No. 9,345,481, titled STAPLE CARTRIDGE TISSUE THICKNESS SENSOR SYSTEM, which issued on May 24, 2016, which is herein incorporated by reference in its entirety; U.S. Patent Application Publication No. 2014/0263552, titled STAPLE CARTRIDGE TISSUE THICKNESS SENSOR SYSTEM, which published on Sep. 18, 2014, which is herein incorporated by reference in its entirety; and U.S. patent application Ser. No. 15/628,175, titled TECHNIQUES FOR ADAPTIVE CONTROL OF MOTOR VELOCITY OF A SURGICAL STAPLING AND CUTTING INSTRUMENT, filed Jun. 20, 2017, which is herein incorporated by reference in its entirety. In a digital signal processing system, an absolute positioning system is coupled to a digital data acquisition system where the output of the absolute positioning system will have a finite resolution and sampling frequency. The absolute positioning system may comprise a compare-and-combine circuit to combine a computed response with a measured response using algorithms, such as a weighted average and a theoretical control loop, that drive the computed response towards the measured response. The computed response of the physical system takes into account properties like mass, inertial, viscous friction, inductance resistance, etc., to predict what the states and outputs of the physical system will be by knowing the input.

The absolute positioning system provides an absolute position of the displacement member upon power-up of the instrument, without retracting or advancing the displacement member to a reset (zero or home) position as may be required with conventional rotary encoders that merely count the number of steps forwards or backwards that the motor 482 has taken to infer the position of a device actuator, drive bar, knife, or the like.

A sensor 474, such as, for example, a strain gauge or a micro-strain gauge, is configured to measure one or more parameters of the end effector, such as, for example, the amplitude of the strain exerted on the anvil during a clamping operation, which can be indicative of the closure forces applied to the anvil. The measured strain is converted to a digital signal and provided to the processor 462. Alternatively, or in addition to the sensor 474, a sensor 476, such as, for example, a load sensor, can measure the closure force applied by the closure drive system to the anvil. The sensor 476, such as, for example, a load sensor, can measure the firing force applied to a knife in a firing stroke of the surgical instrument or tool. The knife is configured to engage a wedge sled, which is configured to upwardly cam staple drivers to force out staples into deforming contact with an anvil. The knife also includes a sharpened cutting edge that can be used to sever tissue as the knife is advanced distally by the firing bar. Alternatively, a current sensor 478 can be employed to measure the current drawn by the motor 482. The force required to advance the firing member can correspond to the current drawn by the motor 482, for example. The measured force is converted to a digital signal and provided to the processor 462.

In one form, the strain gauge sensor 474 can be used to measure the force applied to the tissue by the end effector. A strain gauge can be coupled to the end effector to measure the force on the tissue being treated by the end effector. A system for measuring forces applied to the tissue grasped by the end effector comprises a strain gauge sensor 474, such as, for example, a micro-strain gauge, that is configured to measure one or more parameters of the end effector, for example. In one aspect, the strain gauge sensor 474 can measure the amplitude or magnitude of the strain exerted on a jaw member of an end effector during a clamping operation, which can be indicative of the tissue compression. The measured strain is converted to a digital signal and provided to a processor 462 of the microcontroller 461. A load sensor 476 can measure the force used to operate the knife element, for example, to cut the tissue captured between the anvil and the staple cartridge. A magnetic field sensor can be employed to measure the thickness of the captured tissue. The measurement of the magnetic field sensor also may be converted to a digital signal and provided to the processor 462.

The measurements of the tissue compression, the tissue thickness, and/or the force required to close the end effector on the tissue, as respectively measured by the sensors 474, 476, can be used by the microcontroller 461 to characterize the selected position of the firing member and/or the corresponding value of the speed of the firing member. In one instance, a memory 468 may store a technique, an equation, and/or a lookup table which can be employed by the microcontroller 461 in the assessment.

The control system 470 of the surgical instrument or tool also may comprise wired or wireless communication circuits to communicate with the modular communication hub as shown in FIGS. 1-14. The control system 470 may be employed by the motorized circular stapling instrument 201800 (FIGS. 24-30), 201502 (FIGS. 31-32), 201532 (FIGS. 34-35), 201610 (FIGS. 36-40) to control aspects of the motorized circular stapling instruments 201800, 201502, 201532 201610. Aspects of the control system 470 may be employed by the motorized circular stapling instruments

201800, 201502, 201532, 201610 to sense the position of the anvil, tissue compression forces, among others, by employing 472, 474, 476, the tracking system 480, and current sensor 478 to provide feedback to the controller 461.

Figure 17:
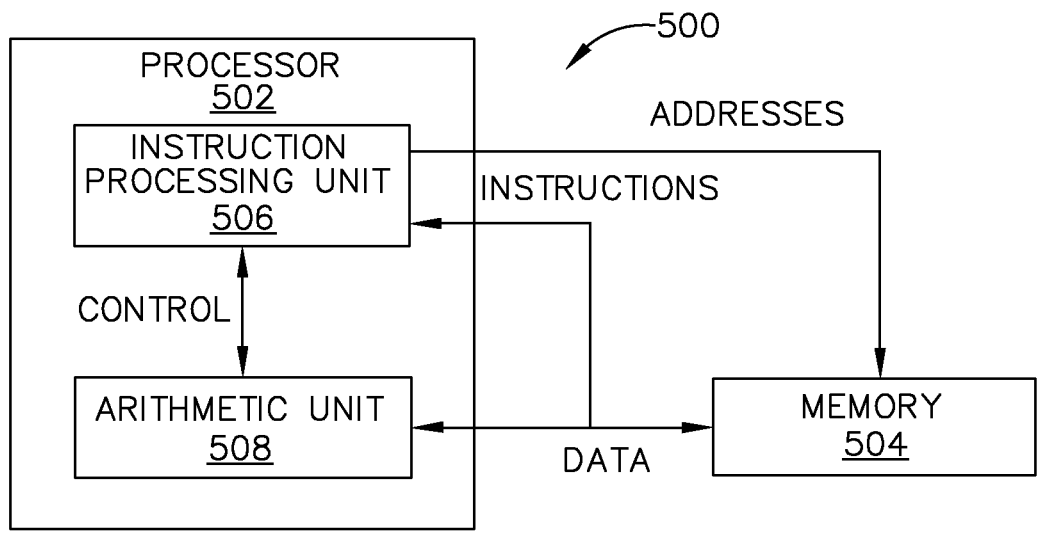
FIG. 17 illustrates a control circuit configured to control aspects of the surgical instrument or tool, in accordance with at least one aspect of the present disclosure.

FIG. 17 illustrates a control circuit 500 configured to control aspects of the surgical instrument or tool according to one aspect of this disclosure. The control circuit 500 can be configured to implement various processes described herein. The control circuit 500 may comprise a microcontroller comprising one or more processors 502 (e.g., microprocessor, microcontroller) coupled to at least one memory circuit 504. The memory circuit 504 stores machine-executable instructions that, when executed by the processor 502, cause the processor 502 to execute machine instructions to implement various processes described herein. The processor 502 may be any one of a number of single-core or multicore processors known in the art. The memory circuit 504 may comprise volatile and non-volatile storage media. The processor 502 may include an instruction processing unit 506 and an arithmetic unit 508. The instruction processing unit may be configured to receive instructions from the memory circuit 504 of this disclosure.

Figure 18:
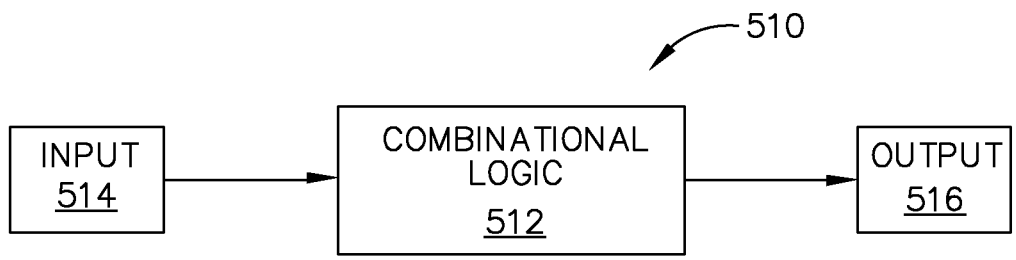
FIG. 18 illustrates a combinational logic circuit configured to control aspects of the surgical instrument or tool, in accordance with at least one aspect of the present disclosure.

FIG. 18 illustrates a combinational logic circuit 510 configured to control aspects of the surgical instrument or tool according to one aspect of this disclosure. The combinational logic circuit 510 can be configured to implement various processes described herein. The combinational logic circuit 510 may comprise a finite state machine comprising a combinational logic 512 configured to receive data associated with the surgical instrument or tool at an input 514, process the data by the combinational logic 512, and provide an output 516.

Figure 19:
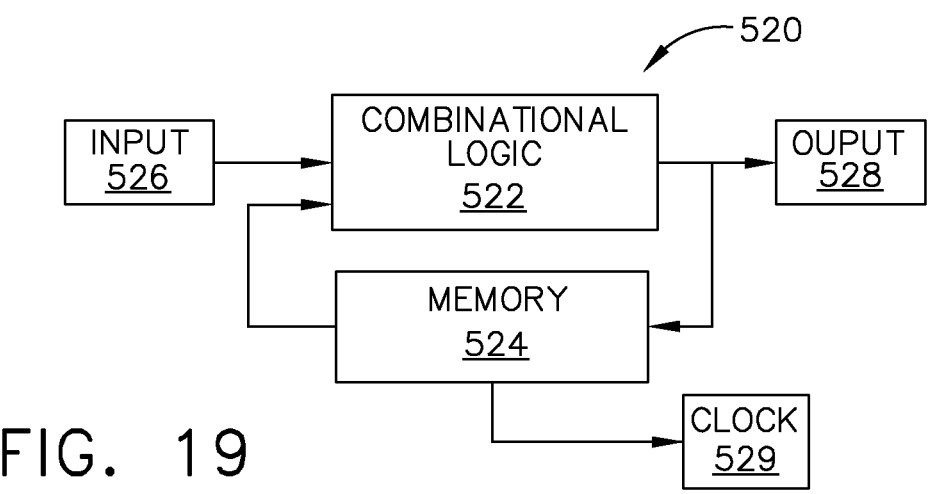
FIG. 19 illustrates a sequential logic circuit configured to control aspects of the surgical instrument or tool, in accordance with at least one aspect of the present disclosure.

FIG. 19 illustrates a sequential logic circuit 520 configured to control aspects of the surgical instrument or tool according to one aspect of this disclosure. The sequential logic circuit 520 or the combinational logic 522 can be configured to implement various processes described herein. The sequential logic circuit 520 may comprise a finite state machine. The sequential logic circuit 520 may comprise a combinational logic 522, at least one memory circuit 524, and a clock 529, for example. The at least one memory circuit 524 can store a current state of the finite state machine. In certain instances, the sequential logic circuit 520 may be synchronous or asynchronous. The combinational logic 522 is configured to receive data associated with the surgical instrument or tool from an input 526, process the data by the combinational logic 522, and provide an output 528. In other aspects, the circuit may comprise a combination of a processor (e.g., processor 502, FIG. 17) and a finite state machine to implement various processes herein. In other aspects, the finite state machine may comprise a combination of a combinational logic circuit (e.g., combinational logic circuit 510, FIG. 18) and the sequential logic circuit 520.

Figure 20:
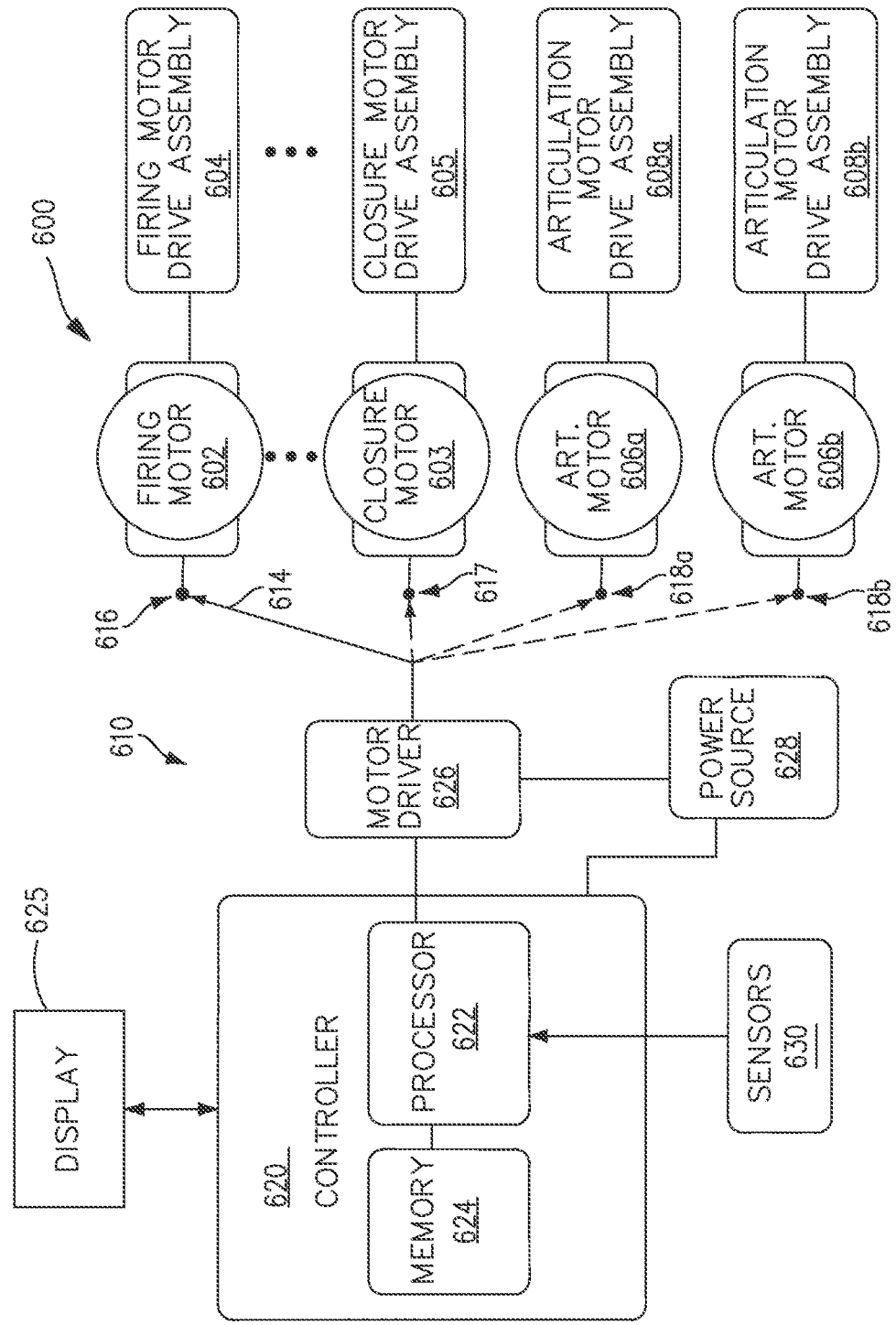
FIG. 20 illustrates a surgical instrument or tool comprising a plurality of motors which can be activated to perform various functions, in accordance with at least one aspect of the present disclosure.

FIG. 20 illustrates a surgical instrument 600 or tool comprising a plurality of motors which can be activated to perform various functions. In certain instances, a first motor can be activated to perform a first function, a second motor can be activated to perform a second function, a third motor can be activated to perform a third function, a fourth motor can be activated to perform a fourth function, and so on. In certain instances, the plurality of motors of the surgical instrument 600 can be individually activated to cause firing, closure, and/or articulation motions in the end effector. The firing, closure, and/or articulation motions can be transmitted to the end effector through a shaft assembly, for example. In one aspect, the surgical instrument 600 is representative of a hand held surgical instrument. In another aspect, the surgical instrument 600 is representative of a robotic surgical instrument. In other aspects, the surgical instrument 600 is representative of a combination of a hand held and robotic surgical instrument. In various aspects, the surgical stapler 600 may be representative of a linear stapler or a circular stapler.

In certain instances, the surgical instrument system or tool may include a firing motor 602. The firing motor 602 may be operably coupled to a firing motor drive assembly 604 which can be configured to transmit firing motions, generated by the motor 602 to the end effector, in particular to displace the knife element. In certain instances, the firing motions generated by the motor 602 may cause the staples to be deployed from the staple cartridge into tissue captured by the end effector and/or the cutting edge of the knife element to be advanced to cut the captured tissue, for example. The knife element may be retracted by reversing the direction of the motor 602.

In certain instances, the surgical instrument or tool may include a closure motor 603. The closure motor 603 may be operably coupled to a closure motor drive assembly 605 which can be configured to transmit closure motions, generated by the motor 603 to the end effector, in particular to displace a closure tube to close the anvil and compress tissue between the anvil and the staple cartridge. The closure motions may cause the end effector to transition from an open configuration to an approximated configuration to capture tissue, for example. The end effector may be transitioned to an open position by reversing the direction of the motor 603. In a circular stapler implementation, the motor 603 may be coupled to a trocar portion of a circular stapler portion of a powered stapling device. The motor 603 can be employed to advance and retract the trocar.

In certain instances, the surgical instrument or tool may include one or more articulation motors 606a, 606b, for example. The motors 606a, 606b may be operably coupled to respective articulation motor drive assemblies 608a, 608b, which can be configured to transmit articulation motions generated by the motors 606a, 606b to the end effector. In certain instances, the articulation motions may cause the end effector to articulate relative to the shaft, for example.

As described above, the surgical instrument or tool may include a plurality of motors which may be configured to perform various independent functions. In certain instances, the plurality of motors of the surgical instrument or tool can be individually or separately activated to perform one or more functions while the other motors remain inactive. For example, the articulation motors 606a, 606b can be activated to cause the end effector to be articulated while the firing motor 602 remains inactive. Alternatively, the firing motor 602 can be activated to fire the plurality of staples, and/or to advance the cutting edge, while the articulation motor 606 remains inactive. Furthermore, the closure motor 603 may be activated simultaneously with the firing motor 602 to cause the closure tube and the knife element to advance distally as described in more detail hereinbelow.

In certain instances, the surgical instrument or tool may include a common control module 610 which can be employed with a plurality of motors of the surgical instrument or tool. In certain instances, the common control module 610 may accommodate one of the plurality of motors at a time. For example, the common control module 610 can be couplable to and separable from the plurality of motors of the surgical instrument individually. In certain instances, a plurality of the motors of the surgical instrument or tool may share one or more common control modules such as the common control module 610. In certain instances, a plurality of motors of the surgical instrument or tool can be individually and selectively engaged with the common control module 610. In certain instances, the common control module 610 can be selectively switched from interfacing with one of a plurality of motors of the surgical instrument or tool to interfacing with another one of the plurality of motors of the surgical instrument or tool.

In at least one example, the common control module 610 can be selectively switched between operable engagement with the articulation motors 606a, 606b and operable engagement with either the firing motor 602 or the closure motor 603. In at least one example, as illustrated in FIG. 20, a switch 614 can be moved or transitioned between a plurality of positions and/or states. In a first position 616, the switch 614 may electrically couple the common control module 610 to the firing motor 602; in a second position 617, the switch 614 may electrically couple the common control module 610 to the closure motor 603; in a third position 618a, the switch 614 may electrically couple the common control module 610 to the first articulation motor 606a; and in a fourth position 618b, the switch 614 may electrically couple the common control module 610 to the second articulation motor 606b, for example. In certain instances, separate common control modules 610 can be electrically coupled to the firing motor 602, the closure motor 603, and the articulations motor 606a, 606b at the same time. In certain instances, the switch 614 may be a mechanical switch, an electromechanical switch, a solid-state switch, or any suitable switching mechanism.

Each of the motors 602, 603, 606a, 606b may comprise a torque sensor to measure the output torque on the shaft of the motor. The force on an end effector may be sensed in any conventional manner, such as by force sensors on the outer sides of the jaws or by a torque sensor for the motor actuating the jaws.

In various instances, as illustrated in FIG. 20, the common control module 610 may comprise a motor driver 626 which may comprise one or more H-Bridge FETs. The motor driver 626 may modulate the power transmitted from a power source 628 to a motor coupled to the common control module 610 based on input from a microcontroller 620 (the "controller"), for example. In certain instances, the microcontroller 620 can be employed to determine the current drawn by the motor, for example, while the motor is coupled to the common control module 610, as described above.

In certain instances, the microcontroller 620 may include a microprocessor 622 (the "processor") and one or more non-transitory computer-readable mediums or memory units 624 (the "memory"). In certain instances, the memory 624 may store various program instructions, which when executed may cause the processor 622 to perform a plurality of functions and/or calculations described herein. In certain instances, one or more of the memory units 624 may be coupled to the processor 622, for example.

In certain instances, the power source 628 can be employed to supply power to the microcontroller 620, for example. In certain instances, the power source 628 may comprise a battery (or "battery pack" or "power pack"), such as a lithium-ion battery, for example. In certain instances, the battery pack may be configured to be releasably mounted to a handle for supplying power to the surgical instrument 600. A number of battery cells connected in series may be used as the power source 628. In certain instances, the power source 628 may be replaceable and/or rechargeable, for example.

In various instances, the processor 622 may control the motor driver 626 to control the position, direction of rotation, and/or velocity of a motor that is coupled to the common control module 610. In certain instances, the processor 622 can signal the motor driver 626 to stop and/or disable a motor that is coupled to the common control module 610. It should be understood that the term "processor" as used herein includes any suitable microprocessor, microcontroller, or other basic computing device that incorporates the functions of a computer's central processing unit (CPU) on an integrated circuit or, at most, a few integrated circuits. The processor is a multipurpose, programmable device that accepts digital data as input, processes it according to instructions stored in its memory, and provides results as output. It is an example of sequential digital logic, as it has internal memory. Processors operate on numbers and symbols represented in the binary numeral system.

In one instance, the processor 622 may be any single-core or multicore processor such as those known under the trade name ARM Cortex by Texas Instruments. In certain instances, the microcontroller 620 may be an LM 4F230H5QR, available from Texas Instruments, for example. In at least one example, the Texas Instruments LM4F230H5QR is an ARM Cortex-M4F Processor Core comprising an on-chip memory of 256 KB single-cycle flash memory, or other non-volatile memory, up to 40 MHz, a prefetch buffer to improve performance above 40 MHz, a 32 KB single-cycle SRAM, an internal ROM loaded with StellarisWare® software, a 2 KB EEPROM, one or more PWM modules, one or more QEI analogs, one or more 12-bit ADCs with 12 analog input channels, among other features that are readily available for the product datasheet. Other microcontrollers may be readily substituted for use with the module 4410. Accordingly, the present disclosure should not be limited in this context.

In certain instances, the memory 624 may include program instructions for controlling each of the motors of the surgical instrument 600 that are couplable to the common control module 610. For example, the memory 624 may include program instructions for controlling the firing motor 602, the closure motor 603, and the articulation motors 606a, 606b. Such program instructions may cause the processor 622 to control the firing, closure, and articulation functions in accordance with inputs from algorithms or control programs of the surgical instrument or tool.

In certain instances, one or more mechanisms and/or sensors such as, for example, sensors 630 can be employed to alert the processor 622 to the program instructions that should be used in a particular setting. For example, the sensors 630 may alert the processor 622 to use the program instructions associated with firing, closing, and articulating the end effector. In certain instances, the sensors 630 may comprise position sensors which can be employed to sense the position of the switch 614, for example. Accordingly, the processor 622 may use the program instructions associated with firing the knife of the end effector upon detecting, through the sensors 630 for example, that the switch 614 is in the first position 616; the processor 622 may use the program instructions associated with closing the anvil upon detecting, through the sensors 630 for example, that the switch 614 is in the second position 617; and the processor 622 may use the program instructions associated with articulating the end effector upon detecting, through the sensors 630 for example, that the switch 614 is in the third or fourth position 618a, 618b.

The surgical instrument 600 may comprise wired or wireless communication circuits to communicate with the modular communication hub as shown in FIGS. 1-14. The surgical instrument 600 may be the motorized circular stapling instrument 201800 (FIGS. 24-30), 201502 (FIGS. 31-32), 201532 (FIGS. 34-35), 201610 (FIGS. 36-40).

Figure 21:
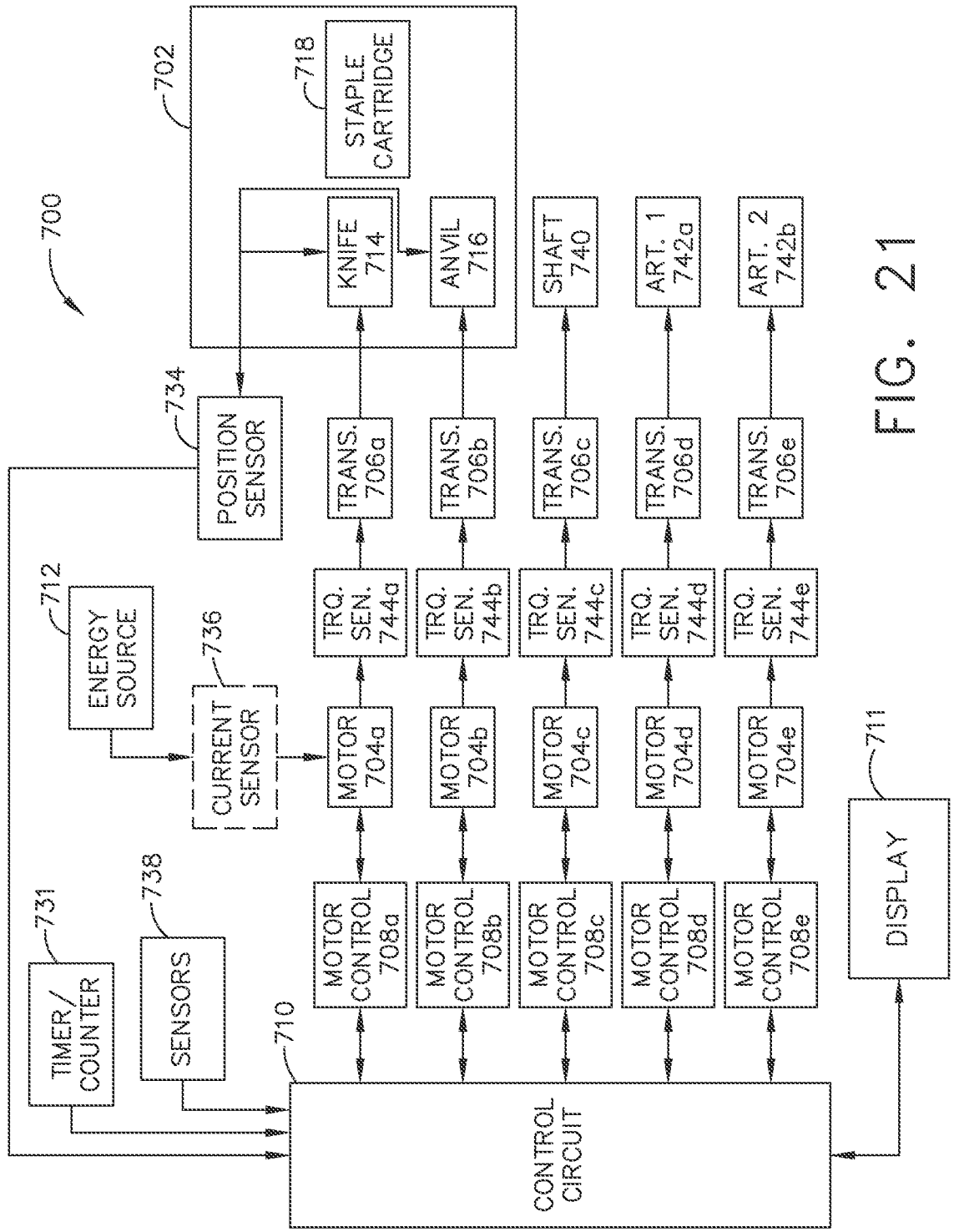
FIG. 21 is a schematic diagram of a surgical instrument configured to operate a surgical tool described herein, in accordance with at least one aspect of the present disclosure.

FIG. 21 is a schematic diagram of a surgical instrument 700 configured to operate a surgical tool described herein according to one aspect of this disclosure. The surgical instrument 700 may be programmed or configured to control distal/proximal translation of a displacement member, distal/proximal displacement of a closure tube, shaft rotation, and articulation, either with single or multiple articulation drive links. In one aspect, the surgical instrument 700 may be programmed or configured to individually control a firing member, a closure member, a shaft member, and/or one or more articulation members. The surgical instrument 700 comprises a control circuit 710 configured to control motor-driven firing members, closure members, shaft members, and/or one or more articulation members. In one aspect, the surgical instrument 700 is representative of a hand held surgical instrument. In another aspect, the surgical instrument 700 is representative of a robotic surgical instrument. In other aspects, the surgical instrument 700 is representative of a combination of a hand held and robotic surgical instrument. In various aspects, the surgical stapler 700 may be representative of a linear stapler or a circular stapler.

In one aspect, the surgical instrument 700 comprises a control circuit 710 configured to control an anvil 716 and a knife 714 (or cutting element including a sharp cutting edge) portion of an end effector 702, a removable staple cartridge 718, a shaft 740, and one or more articulation members 742*a*, 742*b* via a plurality of motors 704*a*-704*e*. A position sensor 734 may be configured to provide position feedback of the knife 714 to the control circuit 710. Other sensors 738 may be configured to provide feedback to the control circuit 710. A timer/counter 731 provides timing and counting information to the control circuit 710. An energy source 712 may be provided to operate the motors 704*a*-704*e*, and a current sensor 736 provides motor current feedback to the control circuit 710. The motors 704*a*-704*e* can be operated individually by the control circuit 710 in an open-loop or closed-loop feedback control.

In one aspect, the control circuit 710 may comprise one or more microcontrollers, microprocessors, or other suitable processors for executing instructions that cause the processor or processors to perform one or more tasks. In one aspect, a timer/counter 731 provides an output signal, such as the elapsed time or a digital count, to the control circuit 710 to correlate the position of the knife 714 as determined by the position sensor 734 with the output of the timer/counter 731 such that the control circuit 710 can determine the position of the knife 714 at a specific time (t) relative to a starting position or the time (t) when the knife 714 is at a specific position relative to a starting position. The timer/counter 731 may be configured to measure elapsed time, count external events, or time external events.

In one aspect, the control circuit 710 may be programmed to control functions of the end effector 702 based on one or more tissue conditions. The control circuit 710 may be programmed to sense tissue conditions, such as thickness, either directly or indirectly, as described herein. The control circuit 710 may be programmed to select a firing control program or closure control program based on tissue conditions. A firing control program may describe the distal motion of the displacement member. Different firing control programs may be selected to better treat different tissue conditions. For example, when thicker tissue is present, the control circuit 710 may be programmed to translate the displacement member at a lower velocity and/or with lower power. When thinner tissue is present, the control circuit 710 may be programmed to translate the displacement member at a higher velocity and/or with higher power. A closure control program may control the closure force applied to the tissue by the anvil 716. Other control programs control the rotation of the shaft 740 and the articulation members 742*a*, 742*b*.

In one aspect, the control circuit 710 may generate motor set point signals. The motor set point signals may be provided to various motor controllers 708*a*-708*e*. The motor controllers 708*a*-708*e* may comprise one or more circuits configured to provide motor drive signals to the motors 704*a*-704*e* to drive the motors 704*a*-704*e* as described herein. In some examples, the motors 704*a*-704*e* may be brushed DC electric motors. For example, the velocity of the motors 704*a*-704*e* may be proportional to the respective motor drive signals. In some examples, the motors 704*a*-704*e* may be brushless DC electric motors, and the respective motor drive signals may comprise a PWM signal provided to one or more stator windings of the motors 704*a*-704*e*. Also, in some examples, the motor controllers 708*a*-708*e* may be omitted and the control circuit 710 may generate the motor drive signals directly.

In one aspect, the control circuit 710 may initially operate each of the motors 704*a*-704*e* in an open-loop configuration for a first open-loop portion of a stroke of the displacement member. Based on the response of the surgical instrument 700 during the open-loop portion of the stroke, the control circuit 710 may select a firing control program in a closed-loop configuration. The response of the instrument may include a translation distance of the displacement member during the open-loop portion, a time elapsed during the open-loop portion, the energy provided to one of the motors 704*a*-704*e* during the open-loop portion, a sum of pulse widths of a motor drive signal, etc. After the open-loop portion, the control circuit 710 may implement the selected firing control program for a second portion of the displacement member stroke. For example, during a closed-loop portion of the stroke, the control circuit 710 may modulate one of the motors 704*a*-704*e* based on translation data describing a position of the displacement member in a closed-loop manner to translate the displacement member at a constant velocity.

In one aspect, the motors 704*a*-704*e* may receive power from an energy source 712. The energy source 712 may be a DC power supply driven by a main alternating current power source, a battery, a super capacitor, or any other suitable energy source. The motors 704*a*-704*e* may be mechanically coupled to individual movable mechanical elements such as the knife 714, anvil 716, shaft 740, articulation 742*a*, and articulation 742*b* via respective transmissions 706*a*-706*e*. The transmissions 706*a*-706*e* may include one or more gears or other linkage components to couple the motors 704*a*-704*e* to movable mechanical elements. A position sensor 734 may sense a position of the knife 714. The position sensor 734 may be or include any type of sensor that is capable of generating position data that indicate a position of the knife 714. In some examples, the position sensor 734 may include an encoder configured to provide a series of pulses to the control circuit 710 as the knife 714 translates distally and proximally. The control circuit 710 may track the pulses to determine the position of the knife 714. Other suitable position sensors may be used, including, for example, a proximity sensor. Other types of position sensors may provide other signals indicating motion of the knife 714. Also, in some examples, the position sensor 734 may be omitted. Where any of the motors 704a-704e is a stepper motor, the control circuit 710 may track the position of the knife 714 by aggregating the number and direction of steps that the motor 704 has been instructed to execute. The position sensor 734 may be located in the end effector 702 or at any other portion of the instrument. The outputs of each of the motors 704a-704e include a torque sensor 744a-744e to sense force and have an encoder to sense rotation of the drive shaft.

In one aspect, the control circuit 710 is configured to drive a firing member such as the knife 714 portion of the end effector 702. The control circuit 710 provides a motor set point to a motor control 708a, which provides a drive signal to the motor 704a. The output shaft of the motor 704a is coupled to a torque sensor 744a. The torque sensor 744a is coupled to a transmission 706a which is coupled to the knife 714. The transmission 706a comprises movable mechanical elements such as rotating elements and a firing member to control the movement of the knife 714 distally and proximally along a longitudinal axis of the end effector 702. In one aspect, the motor 704a may be coupled to the knife gear assembly, which includes a knife gear reduction set that includes a first knife drive gear and a second knife drive gear. A torque sensor 744a provides a firing force feedback signal to the control circuit 710. The firing force signal represents the force required to fire or displace the knife 714. A position sensor 734 may be configured to provide the position of the knife 714 along the firing stroke or the position of the firing member as a feedback signal to the control circuit 710. The end effector 702 may include additional sensors 738 configured to provide feedback signals to the control circuit 710. When ready to use, the control circuit 710 may provide a firing signal to the motor control 708a. In response to the firing signal, the motor 704a may drive the firing member distally along the longitudinal axis of the end effector 702 from a proximal stroke start position to a stroke end position distal to the stroke start position. As the firing member translates distally, a knife 714, with a cutting element positioned at a distal end, advances distally to cut tissue located between the staple cartridge 718 and the anvil 716.

In one aspect, the control circuit 710 is configured to drive a closure member such as the anvil 716 portion of the end effector 702. The control circuit 710 provides a motor set point to a motor control 708b, which provides a drive signal to the motor 704b. The output shaft of the motor 704b is coupled to a torque sensor 744b. The torque sensor 744b is coupled to a transmission 706b which is coupled to the anvil 716. The transmission 706b comprises movable mechanical elements such as rotating elements and a closure member to control the movement of the anvil 716 from the open and closed positions. In one aspect, the motor 704b is coupled to a closure gear assembly, which includes a closure reduction gear set that is supported in meshing engagement with the closure spur gear. The torque sensor 744b provides a closure force feedback signal to the control circuit 710. The closure force feedback signal represents the closure force applied to the anvil 716. The position sensor 734 may be configured to provide the position of the closure member as a feedback signal to the control circuit 710. Additional sensors 738 in the end effector 702 may provide the closure force feedback signal to the control circuit 710. The pivotable anvil 716 is positioned opposite the staple cartridge 718. When ready to use, the control circuit 710 may provide a closure signal to the motor control 708b. In response to the closure signal, the motor 704b advances a closure member to grasp tissue between the anvil 716 and the staple cartridge 718.

In one aspect, the control circuit 710 is configured to rotate a shaft member such as the shaft 740 to rotate the end effector 702. The control circuit 710 provides a motor set point to a motor control 708c, which provides a drive signal to the motor 704c. The output shaft of the motor 704c is coupled to a torque sensor 744c. The torque sensor 744c is coupled to a transmission 706c which is coupled to the shaft 740. The transmission 706c comprises movable mechanical elements such as rotating elements to control the rotation of the shaft 740 clockwise or counterclockwise up to and over 360°. In one aspect, the motor 704c is coupled to the rotational transmission assembly, which includes a tube gear segment that is formed on (or attached to) the proximal end of the proximal closure tube for operable engagement by a rotational gear assembly that is operably supported on the tool mounting plate. The torque sensor 744c provides a rotation force feedback signal to the control circuit 710. The rotation force feedback signal represents the rotation force applied to the shaft 740. The position sensor 734 may be configured to provide the position of the closure member as a feedback signal to the control circuit 710. Additional sensors 738 such as a shaft encoder may provide the rotational position of the shaft 740 to the control circuit 710.

In a circular stapler implementation, the transmission 706c element is coupled to the trocar to advance or retract the trocar. In one aspect, the shaft 740 is part of a closure system that comprises a trocar 201904 and a trocar actuator 201906 as discussed in more detail with reference to FIGS. 29A-29 hereinbelow. Accordingly, the control circuit 710 controls the motor control circuit 708c to control the motor 704c to advance or retract the trocar. A torque sensor 744c is provided to measure the torque applied by the shaft of the motor 704c to the transmission components 706c employed in advancing and retracting the trocar. The position sensor 734 may include a variety of sensors to track the position of the trocar, the anvil 716, or the knife 714, or any combination thereof. Other sensors 738 may be employed to measure a variety of parameters including position or velocity of the trocar, the anvil 716, or the knife 714, or any combination thereof. The torque sensor 744c, the position sensor 734, and the sensors 738 are coupled to the control circuit 710 as inputs to various processes for controlling the operation of the surgical instrument 700 in a desired manner.

In one aspect, the control circuit 710 is configured to articulate the end effector 702. The control circuit 710 provides a motor set point to a motor control 708d, which provides a drive signal to the motor 704d. The output shaft of the motor 704d is coupled to a torque sensor 744d. The torque sensor 744d is coupled to a transmission 706d which is coupled to an articulation member 742a. The transmission 706d comprises movable mechanical elements such as articulation elements to control the articulation of the end effector 702±65°. In one aspect, the motor 704d is coupled to an articulation nut, which is rotatably journaled on the proximal end portion of the distal spine portion and is rotatably driven thereon by an articulation gear assembly. The torque sensor 744d provides an articulation force feedback signal to the control circuit 710. The articulation force feedback signal represents the articulation force applied to the end effector 702. Sensors 738, such as an articulation encoder, may provide the articulation position of the end effector 702 to the control circuit 710.

In another aspect, the articulation function of the robotic surgical system 700 may comprise two articulation members, or links, 742a, 742b. These articulation members 742a, 742b are driven by separate disks on the robot interface (the rack) which are driven by the two motors 708d, 708e. When the separate firing motor 704a is provided, each of articulation links 742a, 742b can be antagonistically driven with respect to the other link in order to provide a resistive holding motion and a load to the head when it is not moving and to provide an articulation motion as the head is articulated. The articulation members 742a, 742b attach to the head at a fixed radius as the head is rotated. Accordingly, the mechanical advantage of the push-and-pull link changes as the head is rotated. This change in the mechanical advantage may be more pronounced with other articulation link drive systems.

In one aspect, the one or more motors 704a-704e may comprise a brushed DC motor with a gearbox and mechanical links to a firing member, closure member, or articulation member. Another example includes electric motors 704a-704e that operate the movable mechanical elements such as the displacement member, articulation links, closure tube, and shaft. An outside influence is an unmeasured, unpredictable influence of things like tissue, surrounding bodies, and friction on the physical system. Such outside influence can be referred to as drag, which acts in opposition to one of electric motors 704a-704e. The outside influence, such as drag, may cause the operation of the physical system to deviate from a desired operation of the physical system.

In one aspect, the position sensor 734 may be implemented as an absolute positioning system. In one aspect, the position sensor 734 may comprise a magnetic rotary absolute positioning system implemented as an AS5055EQFT single-chip magnetic rotary position sensor available from Austria Microsystems, AG. The position sensor 734 may interface with the control circuit 710 to provide an absolute positioning system. The position may include multiple Hall-effect elements located above a magnet and coupled to a CORDIC processor, also known as the digit-by-digit method and Volder's algorithm, that is provided to implement a simple and efficient algorithm to calculate hyperbolic and trigonometric functions that require only addition, subtraction, bitshift, and table lookup operations.

In one aspect, the control circuit 710 may be in communication with one or more sensors 738. The sensors 738 may be positioned on the end effector 702 and adapted to operate with the surgical instrument 700 to measure the various derived parameters such as the gap distance versus time, tissue compression versus time, and anvil strain versus time. The sensors 738 may comprise a magnetic sensor, a magnetic field sensor, a strain gauge, a load cell, a pressure sensor, a force sensor, a torque sensor, an inductive sensor such as an eddy current sensor, a resistive sensor, a capacitive sensor, an optical sensor, and/or any other suitable sensor for measuring one or more parameters of the end effector 702. The sensors 738 may include one or more sensors. The sensors 738 may be located on the staple cartridge 718 deck to determine tissue location using segmented electrodes. The torque sensors 744a-744e may be configured to sense force such as firing force, closure force, and/or articulation force, among others. Accordingly, the control circuit 710 can sense (1) the closure load experienced by the distal closure tube and its position, (2) the firing member at the rack and its position, (3) what portion of the staple cartridge 718 has tissue on it and (4) the load and position on both articulation rods.

In one aspect, the one or more sensors 738 may comprise a strain gauge, such as a micro-strain gauge, configured to measure the magnitude of the strain in the anvil 716 during a clamped condition. The strain gauge provides an electrical signal whose amplitude varies with the magnitude of the strain. The sensors 738 may comprise a pressure sensor configured to detect a pressure generated by the presence of compressed tissue between the anvil 716 and the staple cartridge 718. The sensors 738 may be configured to detect impedance of a tissue section located between the anvil 716 and the staple cartridge 718 that is indicative of the thickness and/or fullness of tissue located therebetween.

In one aspect, the sensors 738 may be implemented as one or more limit switches, electromechanical devices, solid-state switches, Hall-effect devices, magneto-resistive (MR) devices, giant magneto-resistive (GMR) devices, magnetometers, among others. In other implementations, the sensors 738 may be implemented as solid-state switches that operate under the influence of light, such as optical sensors, IR sensors, ultraviolet sensors, among others. Still, the switches may be solid-state devices such as transistors (e.g., FET, junction FET, MOSFET, bipolar, and the like). In other implementations, the sensors 738 may include electrical conductorless switches, ultrasonic switches, accelerometers, and inertial sensors, among others.

In one aspect, the sensors 738 may be configured to measure forces exerted on the anvil 716 by the closure drive system. For example, one or more sensors 738 can be at an interaction point between the closure tube and the anvil 716 to detect the closure forces applied by the closure tube to the anvil 716. The forces exerted on the anvil 716 can be representative of the tissue compression experienced by the tissue section captured between the anvil 716 and the staple cartridge 718. The one or more sensors 738 can be positioned at various interaction points along the closure drive system to detect the closure forces applied to the anvil 716 by the closure drive system. The one or more sensors 738 may be sampled in real time during a clamping operation by the processor of the control circuit 710. The control circuit 710 receives real-time sample measurements to provide and analyze time-based information and assess, in real time, closure forces applied to the anvil 716.

In one aspect, a current sensor 736 can be employed to measure the current drawn by each of the motors 704a-704e. The force required to advance any of the movable mechanical elements such as the knife 714 corresponds to the current drawn by one of the motors 704a-704e. The force is converted to a digital signal and provided to the control circuit 710. The control circuit 710 can be configured to simulate the response of the actual system of the instrument in the software of the controller. A displacement member can be actuated to move a knife 714 in the end effector 702 at or near a target velocity. The surgical instrument 700 can include a feedback controller, which can be one of any feedback controllers, including, but not limited to a PID, a state feedback, a linear-quadratic (LQR), and/or an adaptive controller, for example. The surgical instrument 700 can include a power source to convert the signal from the feedback controller into a physical input such as case voltage, PWM voltage, frequency modulated voltage, current, torque, and/or force, for example. Additional details are disclosed in U.S. patent application Ser. No. 15/636,829, titled CLOSED LOOP VELOCITY CONTROL TECHNIQUES FOR ROBOTIC SURGICAL INSTRUMENT, filed Jun. 29, 2017, which is herein incorporated by reference in its entirety.

The surgical instrument 700 may comprise wired or wireless communication circuits to communicate with the modular communication hub as shown in FIGS. 1-14. The surgical instrument 700 may be the motorized circular stapling instrument 201800 (FIGS. 24-30), 201502 (FIGS. 31-32), 201532 (FIGS. 34-35), 201610 (FIGS. 36-40).

Figure 22:
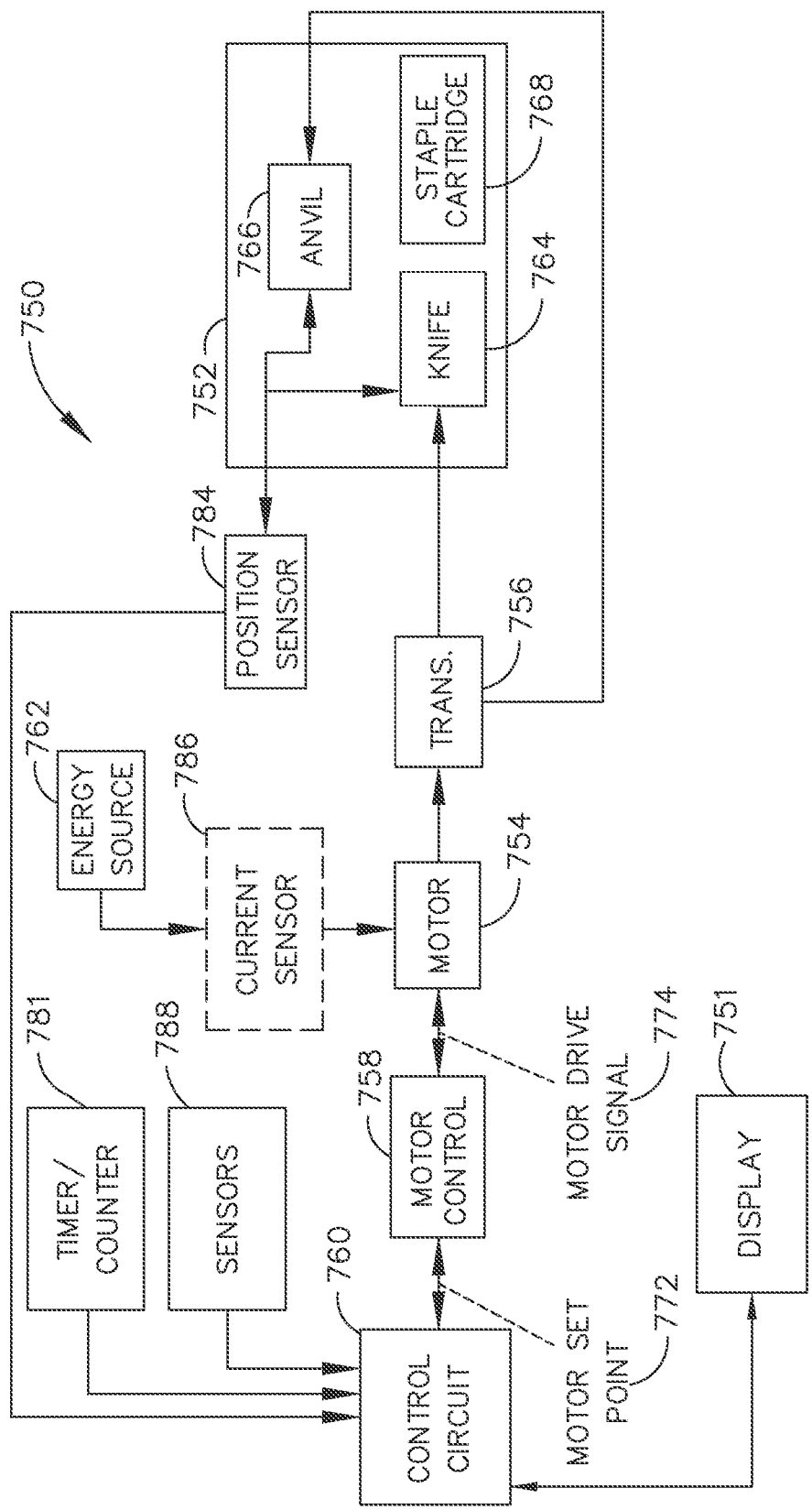
FIG. 22 illustrates a block diagram of a surgical instrument configured to control various functions, in accordance with at least one aspect of the present disclosure.

FIG. 22 illustrates a block diagram of a surgical instrument 750 configured to control various functions, according to one aspect of this disclosure. In one aspect, the surgical instrument 750 is programmed to control the distal translation of a displacement member such as the knife 764, or other suitable cutting element. The surgical instrument 750 comprises an end effector 752 that may comprise an anvil 766, a knife 764 (including a sharp cutting edge), and a removable staple cartridge 768.

The position, movement, displacement, and/or translation of a linear displacement member, such as the knife 764, can be measured by an absolute positioning system, sensor arrangement, and position sensor 784. Because the knife 764 is coupled to a longitudinally movable drive member, the position of the knife 764 can be determined by measuring the position of the longitudinally movable drive member employing the position sensor 784. Accordingly, in the following description, the position, displacement, and/or translation of the knife 764 can be achieved by the position sensor 784 as described herein. A control circuit 760 may be programmed to control the translation of the displacement member, such as the knife 764. The control circuit 760, in some examples, may comprise one or more microcontrollers, microprocessors, or other suitable processors for executing instructions that cause the processor or processors to control the displacement member, e.g., the knife 764, in the manner described. In one aspect, a timer/counter 781 provides an output signal, such as the elapsed time or a digital count, to the control circuit 760 to correlate the position of the knife 764 as determined by the position sensor 784 with the output of the timer/counter 781 such that the control circuit 760 can determine the position of the knife 764 at a specific time (t) relative to a starting position. The timer/counter 781 may be configured to measure elapsed time, count external events, or time external events.

The control circuit 760 may generate a motor set point signal 772. The motor set point signal 772 may be provided to a motor controller 758. The motor controller 758 may comprise one or more circuits configured to provide a motor drive signal 774 to the motor 754 to drive the motor 754 as described herein. In some examples, the motor 754 may be a brushed DC electric motor. For example, the velocity of the motor 754 may be proportional to the motor drive signal 774. In some examples, the motor 754 may be a brushless DC electric motor and the motor drive signal 774 may comprise a PWM signal provided to one or more stator windings of the motor 754. Also, in some examples, the motor controller 758 may be omitted, and the control circuit 760 may generate the motor drive signal 774 directly.

The motor 754 may receive power from an energy source 762. The energy source 762 may be or include a battery, a super capacitor, or any other suitable energy source. The motor 754 may be mechanically coupled to the knife 764 via a transmission 756. The transmission 756 may include one or more gears or other linkage components to couple the motor 754 to the knife 764. In one aspect, the transmission is coupled to a trocar actuator of a circular stapler to advance or retract the trocar. A position sensor 784 may sense a position of the knife 764, the trocar, or the anvil 766, or a combination thereof. The position sensor 784 may be or include any type of sensor that is capable of generating position data that indicate a position of the knife 764. In some examples, the position sensor 784 may include an encoder configured to provide a series of pulses to the control circuit 760 as the knife 764 translates distally and proximally. The control circuit 760 may track the pulses to determine the position of the knife 764. Other suitable position sensors may be used, including, for example, a proximity sensor. Other types of position sensors may provide other signals indicating motion of the knife 764. Also, in some examples, the position sensor 784 may be omitted. Where the motor 754 is a stepper motor, the control circuit 760 may track the position of the knife 764 by aggregating the number and direction of steps that the motor 754 has been instructed to execute. The position sensor 784 may be located in the end effector 752 or at any other portion of the instrument.

In a circular stapler implementation, the transmission 756 element may be coupled to the trocar to advance or retract the trocar, to the knife 764 to advance or retract the knife 764, or the anvil 766 to advance or retract the anvil 766. These functions may be implemented with a single motor using suitable clutching mechanism or may be implemented using separate motors as shown with reference to FIG. 21, for example. In one aspect, the transmission 756 is part of a closure system that comprises a trocar 201904 and a trocar actuator 201906 as discussed in more detail with reference to FIGS. 29A-29C hereinbelow. Accordingly, the control circuit 760 controls the motor control circuit 758 to control the motor 754 to advance or retract the trocar. Similarly, the motor 754 may be configured to advance or retract the knife 764 and advance or retract the anvil 766. A torque sensor may be provided to measure the torque applied by the shaft of the motor 754 to the transmission components 756 employed in advancing and retracting the trocar, the knife 764, or the anvil 766, or combinations thereof. The position sensor 784 may include a variety of sensors to track the position of the trocar, the knife 764, or the anvil 766, or any combination thereof. Other sensors 788 may be employed to measure a variety of parameters including position or velocity of the trocar, the knife 764, or the anvil 766, or any combination thereof. The torque sensor, the position sensor 784, and the sensors 788 are coupled to the control circuit 760 as inputs to various processes for controlling the operation of the surgical instrument 750 in a desired manner.

The control circuit 760 may be in communication with one or more sensors 788. The sensors 788 may be positioned on the end effector 752 and adapted to operate with the surgical instrument 750 to measure the various derived parameters such as gap distance versus time, tissue compression versus time, and anvil strain versus time. The sensors 788 may comprise a magnetic sensor, a magnetic field sensor, a strain gauge, a pressure sensor, a force sensor, an inductive sensor such as an eddy current sensor, a resistive sensor, a capacitive sensor, an optical sensor, and/or any other suitable sensor for measuring one or more parameters of the end effector 752. The sensors 788 may include one or more sensors. In one aspect, the sensors 788 may be configured to determine the position of a trocar of a circular stapler.

The one or more sensors 788 may comprise a strain gauge, such as a micro-strain gauge, configured to measure the magnitude of the strain in the anvil 766 during a clamped condition. The strain gauge provides an electrical signal whose amplitude varies with the magnitude of the strain. The sensors 788 may comprise a pressure sensor configured to detect a pressure generated by the presence of compressed tissue between the anvil 766 and the staple cartridge 768. The sensors 788 may be configured to detect impedance of a tissue section located between the anvil 766 and the staple cartridge 768 that is indicative of the thickness and/or fullness of tissue located therebetween.

The sensors 788 may be is configured to measure forces exerted on the anvil 766 by a closure drive system. For example, one or more sensors 788 can be at an interaction point between a closure tube and the anvil 766 to detect the closure forces applied by a closure tube to the anvil 766. The forces exerted on the anvil 766 can be representative of the tissue compression experienced by the tissue section captured between the anvil 766 and the staple cartridge 768. The one or more sensors 788 can be positioned at various interaction points along the closure drive system to detect the closure forces applied to the anvil 766 by the closure drive system. The one or more sensors 788 may be sampled in real time during a clamping operation by a processor of the control circuit 760. The control circuit 760 receives real-time sample measurements to provide and analyze time-based information and assess, in real time, closure forces applied to the anvil 766.

A current sensor 786 can be employed to measure the current drawn by the motor 754. The force required to advance the knife 764 corresponds to the current drawn by the motor 754. The force is converted to a digital signal and provided to the control circuit 760.

The control circuit 760 can be configured to simulate the response of the actual system of the instrument in the software of the controller. A displacement member can be actuated to move a knife 764 in the end effector 752 at or near a target velocity. The surgical instrument 750 can include a feedback controller, which can be one of any feedback controllers, including, but not limited to a PID, a state feedback, LQR, and/or an adaptive controller, for example. The surgical instrument 750 can include a power source to convert the signal from the feedback controller into a physical input such as case voltage, PWM voltage, frequency modulated voltage, current, torque, and/or force, for example.

The actual drive system of the surgical instrument 750 is configured to drive the displacement member, cutting member, or knife 764, by a brushed DC motor with gearbox and mechanical links to an articulation and/or knife system. Another example is the electric motor 754 that operates the displacement member and the articulation driver, for example, of an interchangeable shaft assembly. An outside influence is an unmeasured, unpredictable influence of things like tissue, surrounding bodies and friction on the physical system. Such outside influence can be referred to as drag which acts in opposition to the electric motor 754. The outside influence, such as drag, may cause the operation of the physical system to deviate from a desired operation of the physical system.

Various example aspects are directed to a surgical instrument 750 comprising an end effector 752 with motor-driven surgical stapling and cutting implements. For example, a motor 754 may drive a displacement member distally and proximally along a longitudinal axis of the end effector 752. The end effector 752 may comprise a pivotable anvil 766 and, when configured for use, a staple cartridge 768 positioned opposite the anvil 766. A clinician may grasp tissue between the anvil 766 and the staple cartridge 768, as described herein. When ready to use the instrument 750, the clinician may provide a firing signal, for example by depressing a trigger of the instrument 750. In response to the firing signal, the motor 754 may drive the displacement member distally along the longitudinal axis of the end effector 752 from a proximal stroke begin position to a stroke end position distal of the stroke begin position. As the displacement member translates distally, a knife 764 with a cutting element positioned at a distal end, may cut the tissue between the staple cartridge 768 and the anvil 766.

In various examples, the surgical instrument 750 may comprise a control circuit 760 programmed to control the distal translation of the displacement member, such as the knife 764, for example, based on one or more tissue conditions. The control circuit 760 may be programmed to sense tissue conditions, such as thickness, either directly or indirectly, as described herein. The control circuit 760 may be programmed to select a firing control program based on tissue conditions. A firing control program may describe the distal motion of the displacement member. Different firing control programs may be selected to better treat different tissue conditions. For example, when thicker tissue is present, the control circuit 760 may be programmed to translate the displacement member at a lower velocity and/or with lower power. When thinner tissue is present, the control circuit 760 may be programmed to translate the displacement member at a higher velocity and/or with higher power.

In some examples, the control circuit 760 may initially operate the motor 754 in an open loop configuration for a first open loop portion of a stroke of the displacement member. Based on a response of the instrument 750 during the open loop portion of the stroke, the control circuit 760 may select a firing control program. The response of the instrument may include, a translation distance of the displacement member during the open loop portion, a time elapsed during the open loop portion, energy provided to the motor 754 during the open loop portion, a sum of pulse widths of a motor drive signal, etc. After the open loop portion, the control circuit 760 may implement the selected firing control program for a second portion of the displacement member stroke. For example, during the closed loop portion of the stroke, the control circuit 760 may modulate the motor 754 based on translation data describing a position of the displacement member in a closed loop manner to translate the displacement member at a constant velocity. Additional details are disclosed in U.S. patent application Ser. No. 15/720,852, titled SYSTEM AND METHODS FOR CONTROLLING A DISPLAY OF A SURGICAL INSTRUMENT, filed Sep. 29, 2017, which is herein incorporated by reference in its entirety.

The surgical instrument 750 may comprise wired or wireless communication circuits to communicate with the modular communication hub as shown in FIGS. 1-14. The surgical instrument 750 may be the motorized circular stapling instrument 201800 (FIGS. 24-30), 201502 (FIGS. 31-32), 201532 (FIGS. 34-35), 201610 (FIGS. 36-40).

Figure 23:
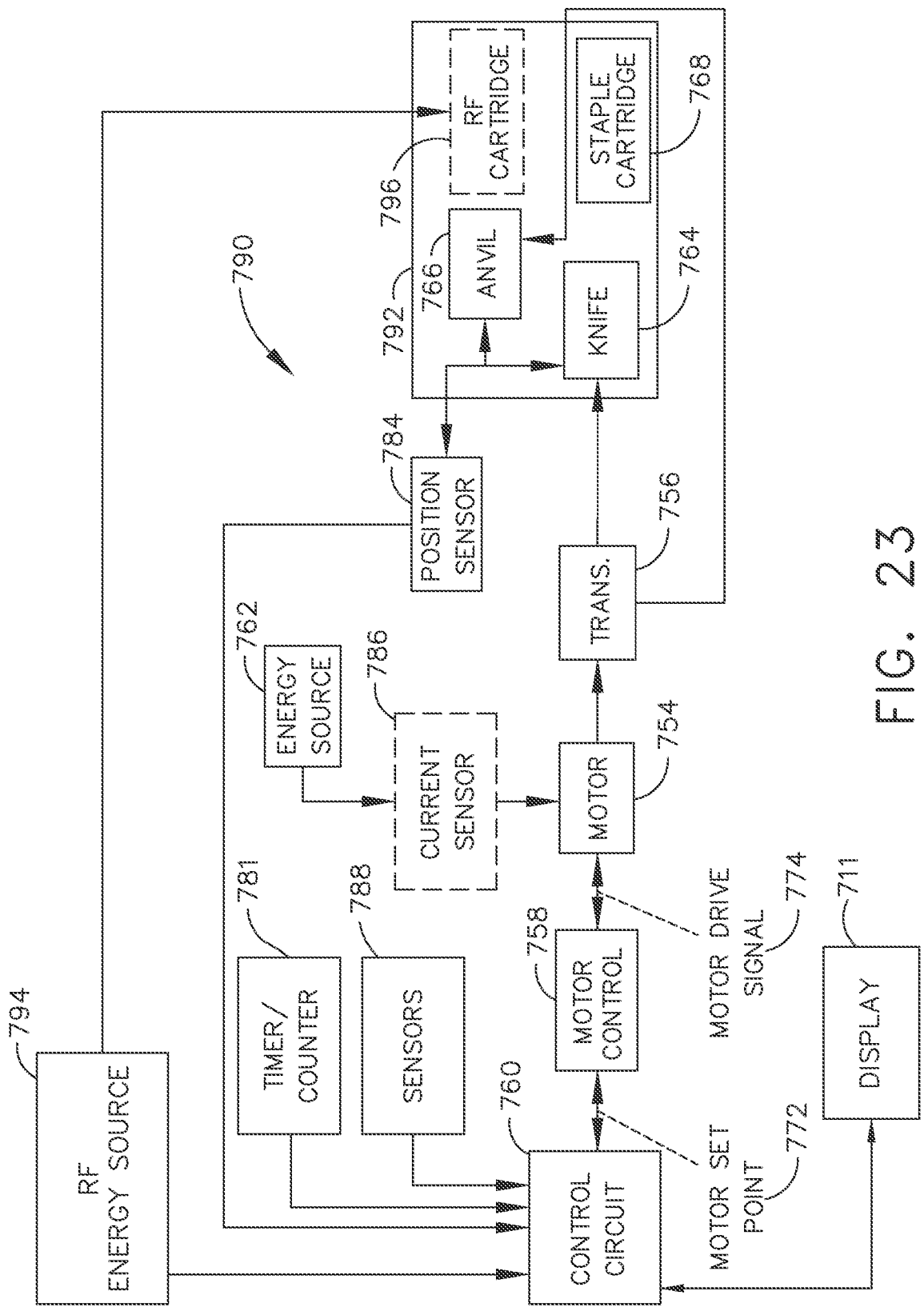
FIG. 23 is a schematic diagram of a surgical instrument configured to control various functions, in accordance with at least one aspect of the present disclosure.

FIG. 23 is a schematic diagram of a surgical instrument 790 configured to control various functions according to one aspect of this disclosure. In one aspect, the surgical instrument 790 is programmed to control distal translation of a displacement member such as the knife 764. The surgical instrument 790 comprises an end effector 792 that may comprise an anvil 766, a knife 764, and a removable staple cartridge 768 which may be interchanged with an RF cartridge 796 (shown in dashed line).

With reference to FIGS. 21-23, in various aspects, sensors 738, 788 may be implemented as a limit switch, electromechanical device, solid-state switches, Hall-effect devices, MR devices, GMR devices, magnetometers, among others. In other implementations, the sensors 738, 788 may be solid-state switches that operate under the influence of light, such as optical sensors, IR sensors, ultraviolet sensors, among others. Still, the switches may be solid-state devices such as transistors (e.g., FET, junction FET, MOSFET, bipolar, and the like). In other implementations, the sensors 738, 788 may include electrical conductorless switches, ultrasonic switches, accelerometers, and inertial sensors, among others.

In one aspect, the position sensor 734, 784 may be implemented as an absolute positioning system comprising a magnetic rotary absolute positioning system implemented as an AS5055EQFT single-chip magnetic rotary position sensor available from Austria Microsystems, AG. The position sensor 734, 784 may interface with the control circuit 760 to provide an absolute positioning system. The position may include multiple Hall-effect elements located above a magnet and coupled to a CORDIC processor, also known as the digit-by-digit method and Volder's algorithm, that is provided to implement a simple and efficient algorithm to calculate hyperbolic and trigonometric functions that require only addition, subtraction, bitshift, and table lookup operations.

In one aspect, the knife 714, 764 may be implemented as a knife member comprising a knife body that operably supports a tissue cutting blade thereon and may further include anvil engagement tabs or features and channel engagement features or a foot. In one aspect, the staple cartridge 718, 768 may be implemented as a standard (mechanical) surgical fastener cartridge, which may be a linear staple cartridge or a circular staple cartridge. In one aspect, the RF cartridge 796 (FIG. 23) may be implemented as an RF cartridge. These and other sensors arrangements are described in commonly owned U.S. patent application Ser. No. 15/628,175, titled TECHNIQUES FOR ADAPTIVE CONTROL OF MOTOR VELOCITY OF A SURGICAL STAPLING AND CUTTING INSTRUMENT, filed Jun. 20, 2017, which is herein incorporated by reference in its entirety.

The position, movement, displacement, and/or translation of a linear displacement member, such as the trocar, the knife 714, 764, or the anvil 716, 766 can be measured by an absolute positioning system, sensor arrangement, and position sensor represented as position sensor 734, 784. Because the knife 714, 764 is coupled to the longitudinally movable drive member, the position of the trocar, the knife 714, 764, or the anvil 716, 766 can be determined by measuring the position of the longitudinally movable drive member employing the position sensor 734, 784. Accordingly, in the following description, the position, displacement, and/or translation of the trocar, the knife 764, or the anvil 716, 766 can be achieved by the position sensor 734, 784 as described herein. A control circuit 710, 760 may be programmed to control the translation of the displacement member, such as the trocar, the knife 764, or the anvil 716, 766 as described herein. The control circuit 710, 760, in some examples, may comprise one or more microcontrollers, microprocessors, or other suitable processors for executing instructions that cause the processor or processors to control the displacement member, e.g., the trocar, the knife 764, or the anvil 716, 766 in the manner described. In one aspect, a timer/counter 731, 781 provides an output signal, such as the elapsed time or a digital count, to the control circuit 710, 760 to correlate the position of trocar, the knife 714, 764, or the anvil 716, 766 as determined by the position sensor 734, 784 with the output of the timer/counter 731, 781 such that the control circuit 710, 760 can determine the position of the trocar, the knife 714, 764, or the anvil 716, 766 at a specific time (t) relative to a starting position. The timer/counter 731, 781 may be configured to measure elapsed time, count external events, or time external events.

The control circuit 710, 760 may generate a motor set point signal 772. The motor set point signal 772 (to each motor when multiple motors are used) may be provided to a motor controller 708a-e, 758. The motor controller 708a-e, 758 may comprise one or more circuits configured to provide a motor drive signal 774 to the motor 704a-e, 754 to drive the motor 704a-e, 754 as described herein. In some examples, the motor 704a-e, 754 may be a brushed DC electric motor. For example, the velocity of the motor 704a-e, 754 may be proportional to the motor drive signal 774. In some examples, the motor 704a-e, 754 may be a brushless DC electric motor and the motor drive signal 774 may comprise a PWM signal provided to one or more stator windings of the motor 704a-e, 754. Also, in some examples, the motor controller 708a-e, 758 may be omitted, and the control circuit 710, 760 may generate the motor drive signal 774 directly.

The motor 704a-e, a battery, a super capacitor, or any other suitable energy source. The motor 704a-e, 754 may be mechanically coupled to the trocar, the knife 764, or the anvil 716, 766 via a transmission 706a-e, 756. The transmission 706a-e, 756 may include one or more gears or other linkage components to couple the motor 704a-e, 754 to the trocar, the knife 764, or the anvil 716, 766. A position sensor 734, 784 may sense a position of the trocar, the knife 714, 764, or the anvil 716, 766. The position sensor 734, 784 may be or include any type of sensor that is capable of generating position data that indicate a position of the trocar, the knife 764, or the anvil 716, 766. In some examples, the position sensor 734, 784 may include an encoder configured to provide a series of pulses to the control circuit 710, 760 as the trocar, the knife 764, or the anvil 716, 766 translates distally and proximally. The control circuit 710, 760 may track the pulses to determine the position of the trocar, the knife 714, 764, or the anvil 716, 766. Other suitable position sensors may be used, including, for example, a proximity sensor. Other types of position sensors may provide other signals indicating motion of the trocar, the knife 764, or the anvil 716, 766. Also, in some examples, the position sensor 734, 784 may be omitted. Where the motor 704a-e, 754 is a stepper motor, the control circuit 710, 760 may track the position of the trocar, the knife 714, 764, or the anvil 716, 766 by aggregating the number and direction of steps that the motor 704a-e, 754 has been instructed to execute. The position sensor 734, 784 may be located in the end effector 702, 752, 792 or at any other portion of the instrument.

The control circuit 710, 760 may be in communication with one or more sensors 738, 788. The sensors 738, 788 may be positioned on the end effector 702, 752, 792 and adapted to operate with the surgical instrument 700, 750, 790 to measure the various derived parameters such as gap distance versus time, tissue compression versus time, and anvil strain versus time. The sensors 738, 788 may comprise a magnetic sensor, a magnetic field sensor, a strain gauge, a pressure sensor, a force sensor, an inductive sensor such as an eddy current sensor, a resistive sensor, a capacitive sensor, an optical sensor, and/or any other suitable sensor for measuring one or more parameters of the end effector 702, 752, 792. The sensors 738, 788 may include one or more sensors.

The one or more sensors 738, 788 may comprise a strain gauge, such as a micro-strain gauge, configured to measure the magnitude of the strain in the anvil 716, 766 during a clamped condition. The strain gauge provides an electrical signal whose amplitude varies with the magnitude of the strain. The sensor 738, 788 may comprise a pressure sensor configured to detect a pressure generated by the presence of compressed tissue between the anvil 716, 766 and the staple cartridge 718, 768. The sensors 738, 788 may be configured to detect impedance of a tissue section located between the anvil 716, 766 and the staple cartridge 718, 768 that is indicative of the thickness and/or fullness of tissue located therebetween.

The sensors 738, 788 may be is configured to measure forces exerted on the anvil 716, 766 by the closure drive system. For example, one or more sensors 738, 788 can be at an interaction point between a closure tube and the anvil 716, 766 to detect the closure forces applied by a closure tube to the anvil 716, 766. The forces exerted on the anvil 716, 766 can be representative of the tissue compression experienced by the tissue section captured between the anvil 716, 766 and the staple cartridge 738, 768. The one or more sensors 738, 788 can be positioned at various interaction points along the closure drive system to detect the closure forces applied to the anvil 716, 766 by the closure drive system. The one or more sensors 738, 788 may be sampled in real time during a clamping operation by a processor portion of the control circuit 710, 760. The control circuit 760 receives real-time sample measurements to provide and analyze time-based information and assess, in real time, closure forces applied to the anvil 716, 766.

A current sensor 736, 786 can be employed to measure the current drawn by the motor 704a-e, 754. The force required to advance the trocar, the knife 714, 764, or the anvil 716, 766 corresponds to the current drawn by the motor 704a-e, 754. The force is converted to a digital signal and provided to the control circuit 710, 760.

With reference to FIG. 23, an RF energy source 794 is coupled to the end effector 792 and is applied to the RF cartridge 796 when the RF cartridge 796 is loaded in the end effector 792 in place of the staple cartridge 768. The control circuit 760 controls the delivery of the RF energy to the RF cartridge 796.

The surgical instrument 790 may comprise wired or wireless communication circuits to communicate with the modular communication hub as shown in FIGS. 1-14. The surgical instrument 790 may be the motorized circular stapling instrument 201800 (FIGS. 24-30), 201502 (FIGS. 31-32), 201532 (FIGS. 34-35), 201610 (FIGS. 36-40).

Additional details are disclosed in U.S. patent application Ser. No. 15/636,096, titled SURGICAL SYSTEM COUPLABLE WITH STAPLE CARTRIDGE AND RADIO FREQUENCY CARTRIDGE, AND METHOD OF USING SAME, filed Jun. 28, 2017, which is herein incorporated by reference in its entirety.

Motorized Circular Stapling Surgical Instrument

Figure 24:
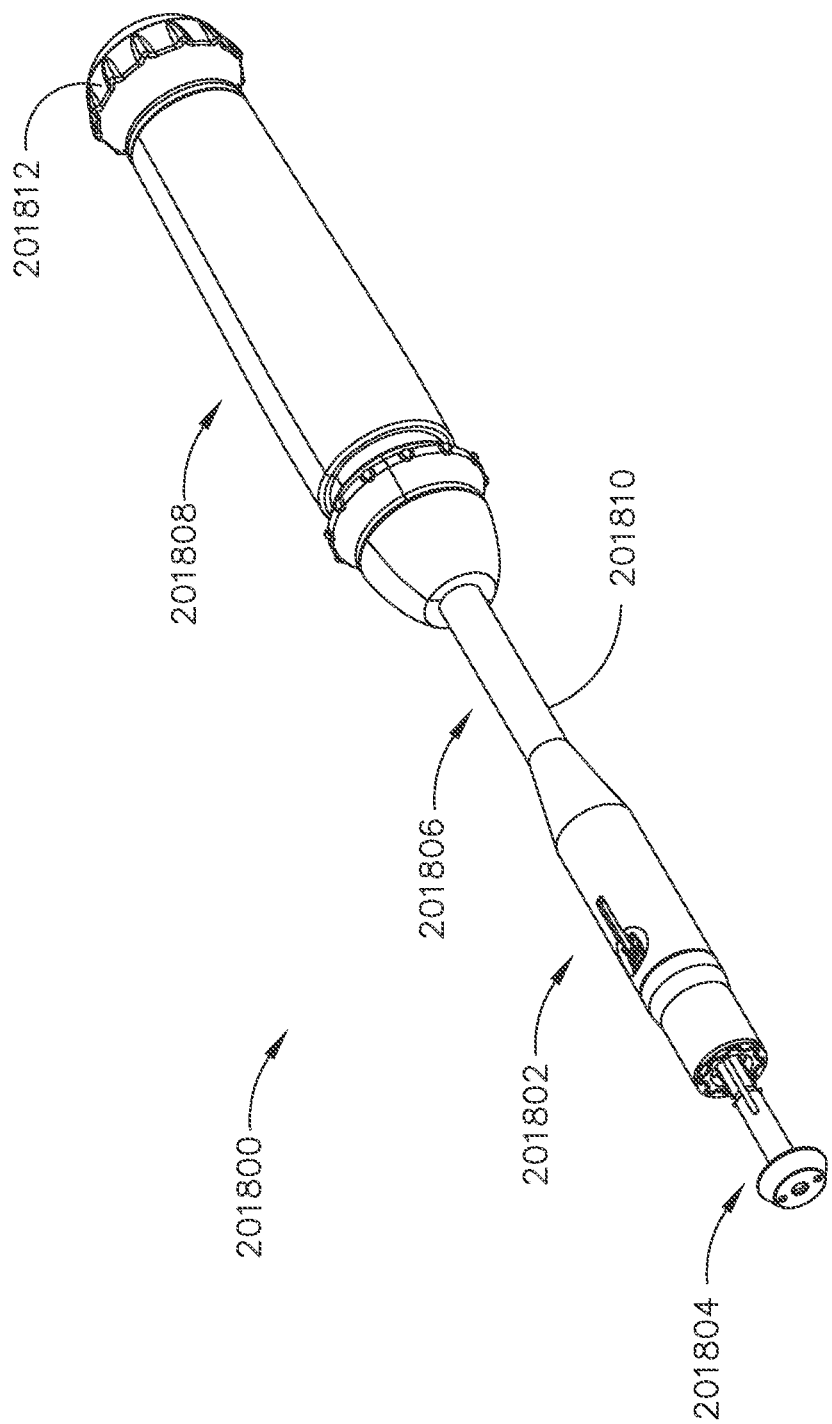
FIG. 24 depicts a perspective view of a circular stapling surgical instrument, in accordance with at least one aspect of the present disclosure.

In some instances, it may be desirable to provide motorized control of a circular stapling instrument. The examples below include merely an illustrative version of a circular stapling instrument where a single motor can be used to control both clamping and cutting/stapling of tissue via a single rotary drive. FIG. 24 shows an example motorized circular stapling instrument 201800. The Instrument 201800 of this example comprises a stapling head assembly 201802, an anvil 201804, a shaft assembly 201806, a handle assembly 201808, and a rotation knob 201812. The stapling head assembly 201802 selectively couples with the anvil 201804. The stapling head assembly 201802 is operable to clamp tissue between staple pockets and staple forming pockets of the anvil 201804. The stapling head assembly 201802 comprises a cylindrical knife that is operable to sever tissue captured between stapling head assembly 201802 and the anvil 201804. The stapling head assembly 201802 drives staples through the tissue captured between stapling head assembly 201802 and the anvil 201804. The stapling instrument 201800 may be used to create a secure anastomosis (e.g., an end-to-end anastomosis) within a gastro-intestinal tract of a patient or elsewhere. An outer tubular member 201810 is coupled to the actuator handle assembly 201808. The outer tubular member 201810 provides a mechanical ground between the stapling head assembly 201802 and the handle assembly 201808.

The stapling head assembly 201802 is operable to clamp tissue, sever tissue, and staple tissue all in response to a single rotary input communicated via the shaft assembly 201806. Accordingly, actuation inputs translated linearly through shaft assembly 201806 are not required for the stapling head assembly 201802, though the stapling head assembly 201802 may comprise a translating clutch feature. By way of example only, at least part of stapling head assembly 201802 may be configured in accordance with at least some of the teachings of U.S. patent application Ser. No. 13/716,318, entitled "Motor Driven Rotary Input Circular Stapler with Modular End Effector," filed on Dec. 17, 2012, and published as U.S. Pat. Pub. No. 2014/0166728 on Jun. 19, 2014, the disclosure of which is incorporated by reference herein. Other suitable configurations for the stapling head assembly 201802 will be apparent to those of ordinary skill in the art in view of the teachings herein.

The shaft assembly 201806 couples the handle assembly 201808 with the stapling head assembly 201802. The shaft assembly 201806 comprises a single actuation feature, rotary driver actuator 201814 shown in FIG. 25. The driver actuator 201814 is operable to drive the stapling head assembly 201802 to clamp tissue, sever tissue, and staple tissue. Accordingly, linear actuation through the shaft assembly 201806 is not required, though the rotary driver actuator 201814 may translate longitudinally to shift between a tissue clamping mode and a tissue cutting/stapling mode. For instance, the driver actuator 201814 may translate from a first longitudinal position, in which rotation of the driver actuator 201814 provides clamping of tissue at the stapling head assembly 201802, to a second longitudinal position, in which rotation of driver actuator 210814 provides cutting and stapling of tissue at the stapling head assembly 201802. Some versions of the shaft assembly 201806 may include one or more flexible sections. An example of a shaft assembly that is configured with flexible sections and that may be incorporated into shaft assembly 201806 is disclosed in U.S. patent application Ser. No. 13/716,323, entitled "Motor Driven Rotary Input Circular Stapler with Lockable Flexible Shaft," filed on Dec. 17, 2012, and published as U.S. Pat. Pub. No. 2014/0166718 on Jun. 19, 2014, the disclosure of which is incorporated by reference herein. Alternatively, the shaft assembly 201806 may be rigid along the length of the shaft assembly 201806 or have one or more flexible sections configured in some other fashion.

Figure 25:
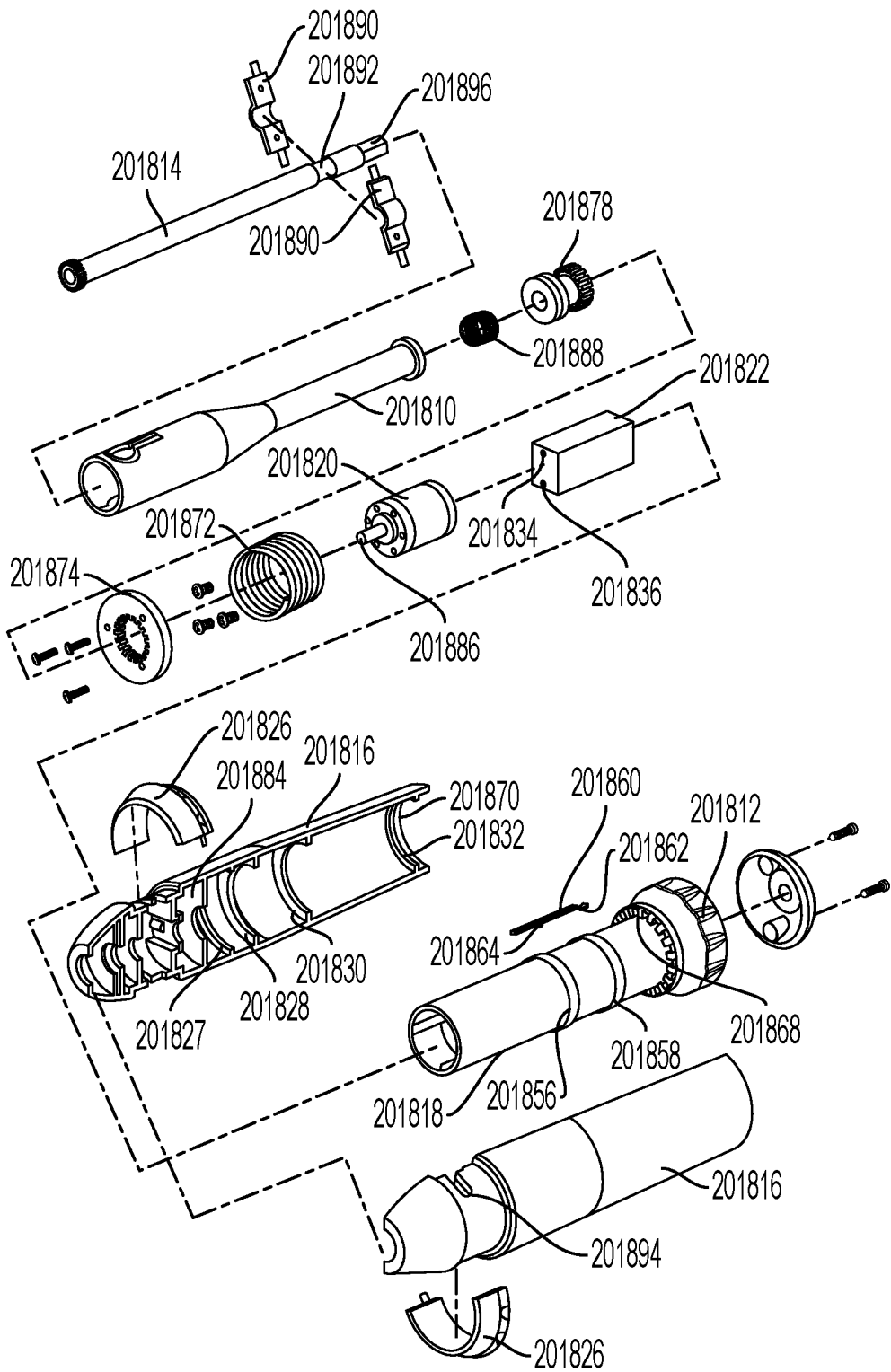
FIG. 25 depicts an exploded view of the handle and shaft assemblies of the instrument of FIG. 24, in accordance with at least one aspect of the present disclosure.

The handle assembly 201808 is shown in FIGS. 25-27. The handle assembly 201808 comprises a handle housing 201816, a motor housing 201818, a motor 201820, a battery 201822, a rotation knob 201812, and a firing ring 201826. The motor housing 201818 is positioned within the handle housing 201816. The handle housing 201816 comprises ribs (201827, 201828, 201830, 201832) extending inwardly into the handle housing 201816 to support the motor housing 201818, as shown in FIG. 26. The battery 201822 is positioned proximal to the motor 201820 within the motor housing 201818. The battery 201822 may be removed from the motor housing 201818 to be replaced, discarded, or recharged. As best seen in FIG. 27, the battery 201822 comprises electrical contacts 201834, 201836 extending distally from the battery 201822. The motor 201820 comprises electrical contacts 201838, 201840 extending proximally from the motor 201820. The battery electrical contact 201836 and the motor electrical contact 201840 are coupled via a conductive metal band 201842. A screw 201844 couples the band 201842 to the motor housing 201818 to fix the position of the band 201842 relative to the motor housing 201818. Accordingly, the band 201842 is configured to constantly couple the battery electrical contact 201836 and the motor electrical contact 201840.

As shown in FIG. 27, a battery electrical contact 201846 is coupled to a conductive metal band 201848. The metal band 201848 is secured to the motor housing 201818 via a conductive screw 201854. The motor electrical contact 201838 is coupled to a conductive metal band 201852. The metal band 201852 is secured to the motor housing 201818 via a conductive screw 201850. The motor housing 201818 is formed of an electrically insulative material (e.g., plastic) and comprises annular contacts 201856, 201858 wrapped around the motor housing 201818. Screws 201850, 201854 are each coupled with a respective annular contact 201856, 201858 to electrically couple the battery electrical contact 201834 and the motor electrical contact 201838 to the annular contacts 201856, 201858, respectively.

Another conductive metal band 201860 is secured to the handle housing 201816. Each end of the metal band 201860 forms a respective spring contact 201862, 201864. The motor housing 201818 translates proximally and/or distally relative to handle housing 201816 to selectively couple and/or decouple the spring contacts 201862, 201864 with annular contacts 201856, 201858. In particular, when the motor housing 201818 is in a distal position, the spring contact 201862 engages the annular contact 201856 and the spring contact 201864 engages the annular contact 201858 to couple the battery 201822 with the motor 201820 and supply power to the motor 201820. It should be understood that, since the spring contacts 201862, 201864 are part of the same conductive metal band 201860, and since the contacts 201836, 201840 are already coupled via a band 201866, the engagement between the spring contacts 201862, 201864 and the annular contacts 201856, 201858 completes a circuit between the battery 201822 and the motor 201820. This positioning is used to provide motorized actuation of the stapling head assembly 201802. When the motor housing 201818 is in a proximal position, the spring contacts 201862, 201864 are decoupled from the annular contacts 201856, 201858, such that the battery 201822 is decoupled from the motor 201820 and the motor 201820 does not receive power. This positioning is used to provide manual actuation of stapling head assembly 201802. The annular shape of the annular contacts 201856, 201858 enables proper contact between the spring contacts 201862, 201864 and the annular contacts 201856, 201858 regardless of the angular position of the motor housing 201818 within the handle housing 201816. In some versions, the band 201860 may include a break that is coupled with an external switch, such that a user may actuate the external switch in order to complete the coupling between the battery 201822 and the motor 201820 after the motor housing 201818 is in the distal position.

A proximal end of motor housing 201818 is fixedly secured to rotation knob 201812, as shown in FIG. 25. In one aspect, rotation knob 201812 may be coupled to a motor to rotate the rotation knob 201812. Rotation knob 201812 protrudes proximally from handle housing 201816 and comprises splines 201868 extending distally from rotation knob 201812. Handle housing 201816 comprises corresponding teeth 201870 to selectively engage splines 201868. Rotation knob 201812 is pulled and/or pushed to translate motor housing 201818 within handle housing 201816. When rotation knob 201812 is in a proximal position, splines 201868 are disengaged from handle housing 201816 such that rotation knob 201812 and motor housing 201818 are free to rotate relative to handle housing 201816. This positioning is used to provide manual actuation of stapling head assembly 201802. When rotation knob 201812 is in a distal position, splines 201868 engage corresponding teeth 201870 in handle housing 201816 to lock rotation knob 201812 and motor housing 201818 from rotating relative to handle housing 201816. Splines 201868 and teeth 201870 thus provide a mechanical ground for motor housing 201818 relative to handle housing 201816. This positioning is used to provide motorized actuation of stapling head assembly 201802 as will be described in greater detail below. Rotation knob 201812 is biased to the distal position by a resilient member 201872 in handle housing 201816. In particular, resilient member 201872 extends distally from rib 201828 of handle housing 201816 to a first gear 201874, which is unitarily secured to the distal end of motor housing 201818. When rotation knob 201812 is in the proximal position, resilient member 201872 compresses between first gear 201874 and rib 201828 to resiliently bias handle housing 201816 to the distal position.

Figure 28A:
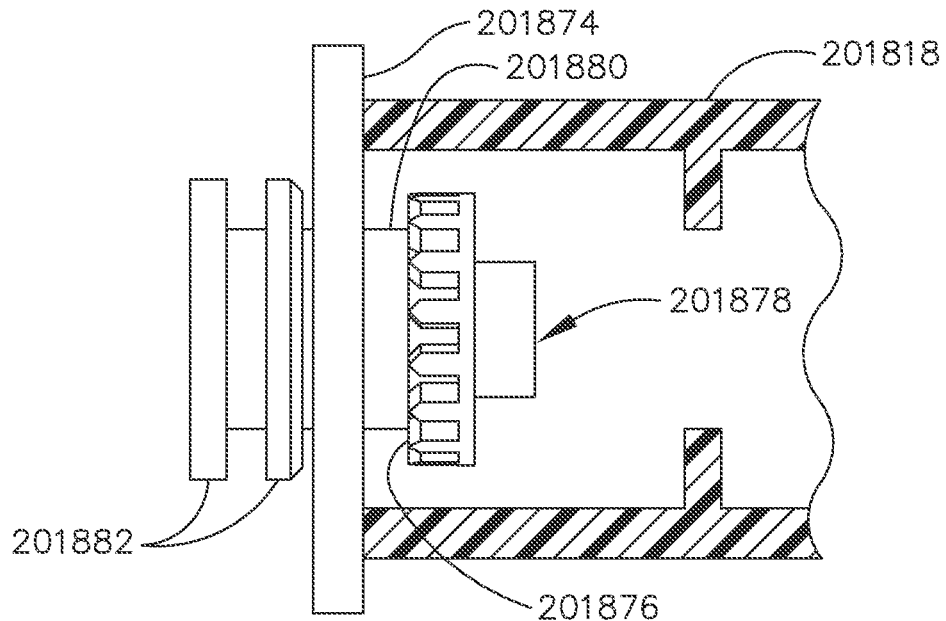
FIG. 28A depicts a side elevational view of an operational mode selection assembly of the instrument of FIG. 24, with a first gear disengaged from a second gear, in accordance with at least one aspect of the present disclosure.
Figure 28B:
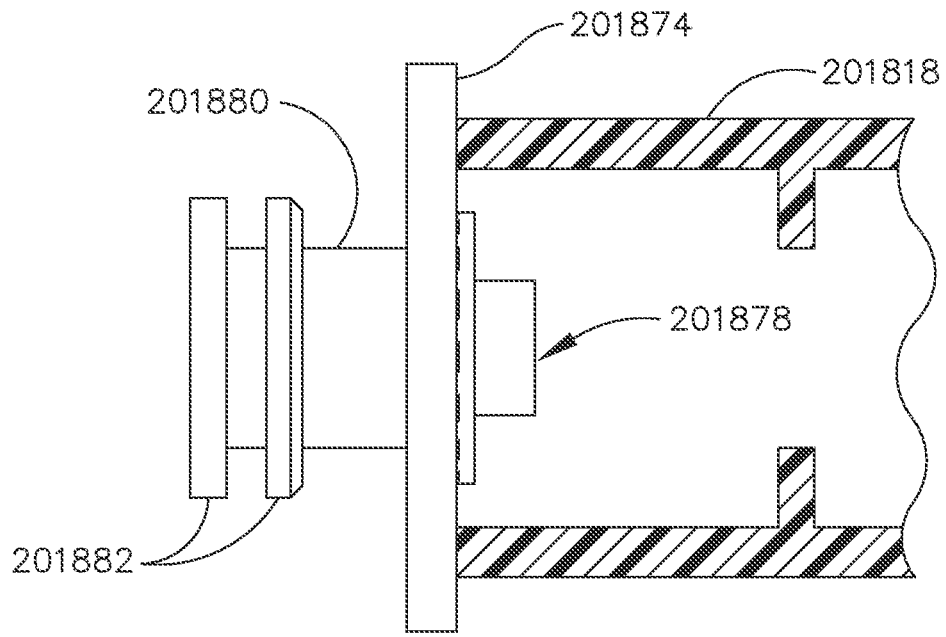
FIG. 28B depicts a side elevational view of the operational mode selection assembly of FIG. 28A, with the first gear engaged with the second gear, in accordance with at least one aspect of the present disclosure.

An operational mode selection assembly is positioned distal to motor housing 201818 within handle housing 201816. As shown in FIGS. 28A-28B, the operational mode selection assembly comprises a first gear 201874 and a second gear 201878, with first gear 201874 being coaxially and slidably disposed about second gear 201878. First gear 201874 comprises square teeth aligned around an inner opening of first gear 201874. The square teeth define a circumferentially spaced array of recesses. Second gear 201878 comprises a shaft 201880, splines 201876, and annular flanges 201882, as shown in FIGS. 28A-28B. Shaft 201880 has a distally presented opening. Distally presented opening is hexagonal to receive proximal end 201896 of driver actuator 201814, which is also hexagonal (FIG. 25). Shaft 201880 also has a proximally presented opening (not shown) that is semi-circular to complement and receive drive shaft 201886 extending distally from motor 201820. Other suitable shapes and configurations of shafts 201896, 201886 may used to couple second gear 201878 with shafts 201896, 201886.

As shown in FIG. 28A, splines 201876 of second gear 201878 are positioned on a proximal end of shaft 201880 and extend distally. Splines 201876 correspond to teeth of first gear 201874, such that splines 201876 are configured to fit within the recesses defined between the teeth. A pair of annular flanges 201882 are positioned at a distal end of shaft 201880 and extend outwardly to engage an inwardly extending annular rib 201884 of handle housing 201816, thereby fixing the longitudinal position of second gear 201878 within handle housing 201816. While annular rib 201884 fixes the longitudinal position of second gear 201878 within handle housing 2001816, annular rib 201884 nevertheless allows second gear 201878 to rotate relative to handle housing 201816. Other suitable engagement features to longitudinally fix second gear 201878 will be apparent to one with ordinary skill in the art based on the teachings herein.

First gear 201874 is positioned around second gear 201878, as shown in FIGS. 28A-28B. First gear 201874 is fixedly coupled to a distal end of motor housing 201818 such that first gear 201874 translates and rotates unitarily with motor housing 201818. When motor housing 201818 is in a proximal position, as shown in FIGS. 28B, motor 201820 and first gear 201874 are also in a proximal position. In this position, drive shaft 201886 of motor 201820 is disengaged from second gear 201878 and teeth of first gear 201874 engage splines of second gear 201878. Thus, when rotation knob 201812 rotates, motor housing 201818 and first gear 201874 also rotate. This positioning thereby provides manual actuation of stapling head assembly 201802. With teeth of first gear 2018784 engaged with splines 201876, rotation knob 201812 thereby rotates second gear 201878 relative to motor housing 201818. When motor housing 201818 is in a distal position, as shown in FIGS. 28A, motor 201820 and first gear 291874 are also in a distal position. Motor 201820 is engaged with second gear 201878 via shafts 201886, 201880. First gear 201874 slides over shaft 201880 of second gear 201878 to disengage splines 201876. Thus, the rotation of drive shaft 201886 of motor 201820 thereby rotates second gear 201878. This positioning thereby provides motorized actuation of stapling head assembly 201802. In other words, when knob 201812 and motor housing 201818 are in a distal position as shown in FIG. 28A, motor 201820 rotates second gear 201878. When knob 201812 and motor housing 201818 are in a proximal position as shown in FIG. 28B, knob 201812 rotates second gear 201878.

Referring back to FIGS. 25-26, a distal end of second gear 201878 is coupled to driver actuator 201814, such that rotation of second gear 201878 rotates driver actuator 201814. Accordingly, when second gear 201878 is rotated, driver actuator 201814 is rotated to adjust the gap distance d between anvil 201804 and stapling head assembly 201802. Handle housing 201816 further comprises firing ring 201826 and coupling member 201890. Coupling member 201890 is secured around recess 201892 of driver actuator 201814, as shown in FIG. 25. Accordingly, coupling member 201890 translates with driver actuator 201814, but driver actuator 201814 is free to rotate within coupling member 201890. Coupling member 201890 comprises protrusions extending outwardly that connect coupling member 201890 to firing ring 201826. The protrusions of coupling member 201890 extends through slot 201894 of housing assembly 201816, as shown in FIG. 25. Slot 201894 extends circumferentially about part of handle assembly 201816. Firing ring 201826 is wrapped around handle housing 201816 and is rotatable and translatable relative to handle housing 201816 to manually drive the protrusions of coupling member 201890 through slot 201894.

When firing ring 201826 is in a distal position, protrusions of coupling member 201890 are positioned within slot 201894 of handle housing 201816. When coupling member 201890 is positioned within slot 201894, coupling member 201890 couples driver actuator 201814 with features in stapling head assembly 201802 operable to adjust the gap distance d between anvil 201804 and stapling head assembly 201802. For instance, if coupling member 201890 is rotated clockwise within slot 201894, the gap distance d is decreased to close anvil 201804 relative to stapling head assembly 201802. If coupling member 201890 is rotated counterclockwise within slot 201894, the gap distance d is increased to open anvil 201804 relative to stapling head assembly 201802. A resilient member 201888 is positioned proximal to coupling member 201890 to bias coupling member 201890 distally (FIG. 25). Coupling member 201890 of firing ring 201826 may then be translated proximally through slots. When firing ring 201826 is in the proximal position, protrusions of coupling member 201890 are positioned within a slot. When coupling member 201890 is positioned within a slot, coupling member 201890 couples driver actuator 201814 with features in stapling head assembly 201802 that drive a knife and staples in response to rotation of driver actuator 201814. For instance, if coupling member 201890 is rotated clockwise within a slot, stapling head assembly 201802 drives a knife and staples. The configuration of the slot prevents coupling member 201890 from being rotated counterclockwise. Other suitable coupling member 201890 rotation configurations will be apparent to one with ordinary skill in view of the teachings herein.

As shown in FIG. 26, a switch 201898 is positioned in handle housing 201816 to align with coupling member 201890. When the motorized operational mode is selected, switch 201898 is configured to electrically couple motor 201820 and battery 201822 when switch 201898 is depressed, and switch 201898 is configured to electrically decouple motor 201820 and battery 201822 when switch 201898 is not depressed. Coupling member 201890 is configured to engage and depress switch 201898 when coupling member 201890 is rotated.

Figure 29A:
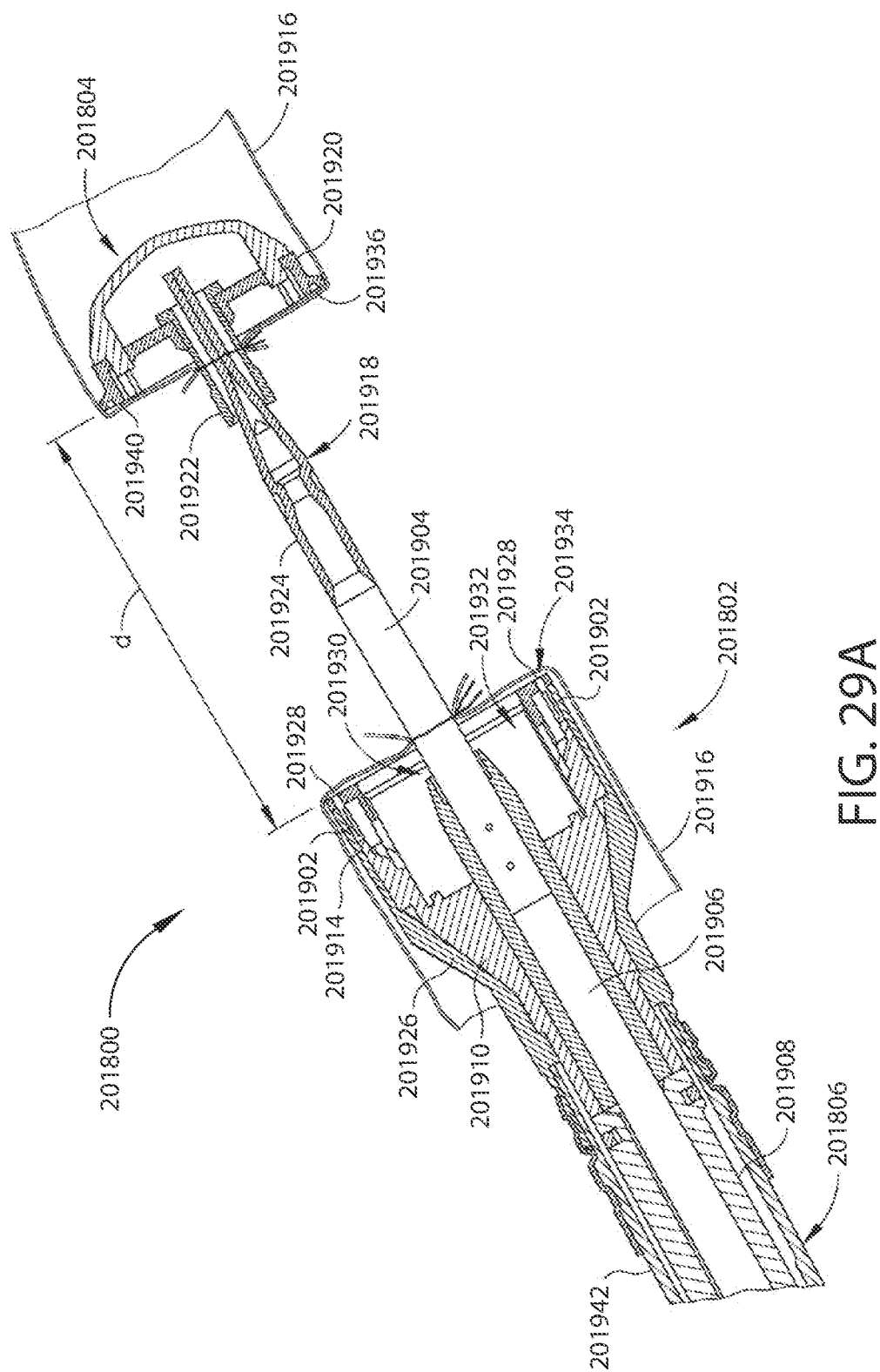
FIG. 29A depicts an enlarged longitudinal cross-section view of a stapling head assembly of the instrument of FIG. 24 showing an anvil in an open position, in accordance with at least one aspect of the present disclosure.
Figure 29B:
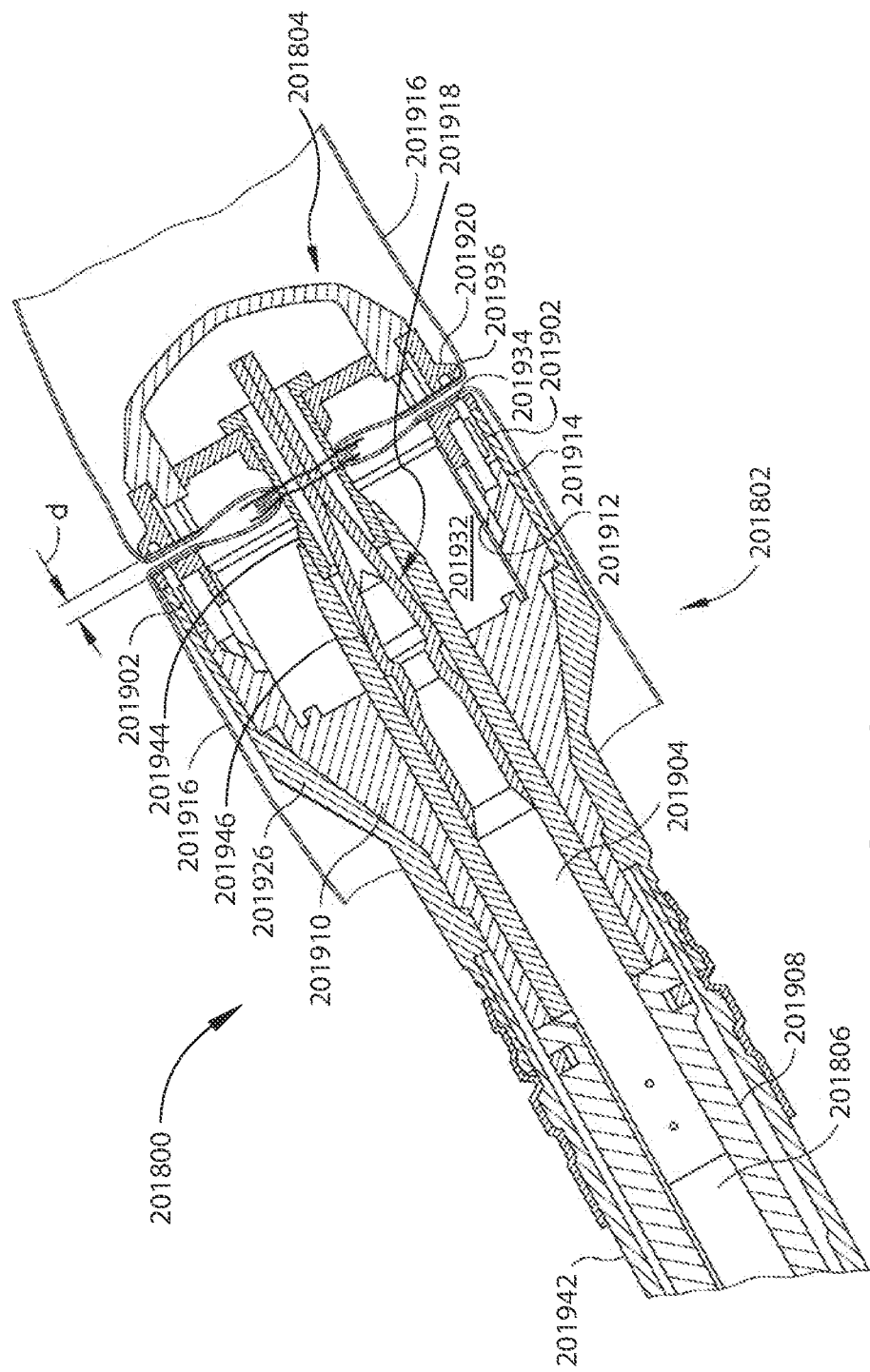
FIG. 29B depicts an enlarged longitudinal cross-sectional view of the stapling head assembly of FIG. 29A showing the anvil in a closed position, in accordance with at least one aspect of the present disclosure.

Referring now to FIGS. 29A-29C, in the present example, instrument 201800 comprises a closure system and a firing system. The closure system comprises a trocar 201904, a trocar actuator 201906, and a rotating knob 201812 (FIG. 24). As previously discussed, the rotation knob 201812 may be coupled to a motor to rotate the rotation knob 201812 in a clockwise or counterclockwise direction. An anvil 201804 may be coupled to a distal end of trocar 201904. Rotating knob 201812 is operable to longitudinally translate trocar 201904 relative to stapling head assembly 201802, thereby translating anvil 201804 when anvil 201804 is coupled to trocar 201904, to clamp tissue between anvil 201804 and stapling head assembly 201804. The firing system comprises a trigger, a trigger actuation assembly, a driver actuator 201908, and a staple driver 201910. Staple driver 201910 includes a cutting element, such as a knife 201912, configured to sever tissue when staple driver 201910 is actuated longitudinally. In addition, staples 201902 are positioned distal to a plurality of staple driving members 201914 of staple driver 201910 such that staple driver 201910 also drives staples 201902 distally when staple driver 201910 is actuated longitudinally. Thus, when staple driver 201910 is actuated via driver actuator 201908, knife 201912 members 201914 substantially simultaneously sever tissue 201916 and drive staples 201902 distally relative to stapling head assembly 201802 into tissue. The components and functionalities of the closure system and firing system will now be described in greater detail.

As shown in FIGS. 29A-29C, anvil 201804 is selectively coupleable to instrument 201800 to provide a surface against which staples 201902 may be bent to staple material contained between stapling head assembly 201802 and anvil 201804. Anvil 201804 of the present example is selectively coupleable to a trocar or pointed rod 201904 that extends distally relative to stapling head assembly 201802. Referring to FIGS. 29A-29C, anvil 201804 is selectively coupleable via the coupling of a proximal shaft 201918 of anvil 201904 to a distal tip of trocar 201904. Anvil 201804 comprises a generally circular anvil head 201920 and a proximal shaft 201918 extending proximally from anvil head 201920. In the example shown, proximal shaft 201918 comprises a tubular member 201922 having resiliently biased retaining clips 201924 to selectively couple anvil 201804 to trocar 201904, though this is merely optional, and it should be understood that other retention features for coupling anvil 201804 to trocar 201904 may be used as well. For example, C-clips, clamps, threading, pins, adhesives, etc. may be employed to couple anvil 201804 to trocar 201904. In addition, while anvil 201804 is described as selectively coupleable to trocar 201904, in some versions proximal shaft 201918 may include a one-way coupling feature such that anvil 201804 cannot be removed from trocar 201904 once anvil 201804 is attached. By way of example one-way features include barbs, one way snaps, collets, collars, tabs, bands, etc. Of course still other configurations for coupling anvil 201804 to trocar 201904 will be apparent to one of ordinary skill in the art in view of the teachings herein. For instance, trocar 201904 may instead be a hollow shaft and proximal shaft 201918 may comprise a sharpened rod that is insertable into the hollow shaft.

Anvil head 201920 of the present example comprises a plurality of staple forming pockets 201936 formed in a proximal face 201940 of anvil head 201920. Accordingly, when anvil 201804 is in the closed position and staples 201902 are driven out of stapling head assembly 201802 into staple forming pockets 201936, as shown in FIG. 29C, legs 201938 of staples 201902 are bent to form completed staples.

With anvil 201804 as a separate component, it should be understood that anvil 201804 may be inserted and secured to a portion of tissue 201916 prior to being coupled to stapling head assembly 201802. By way of example only, anvil 201804 may be inserted into and secured to a first tubular portion of tissue 201916 while instrument 201800 is inserted into and secured to a second tubular portion of tissue 201916. For instance, the first tubular portion of tissue 201916 may be sutured to or about a portion of anvil 201804, and the second tubular portion of tissue 201916 may be sutured to or about trocar 201904.

As shown in FIG. 29A, anvil 201804 is then coupled to trocar 201904. Trocar 201904 of the present example is shown in a distal most actuated position. Such an extended position for trocar 201904 may provide a larger area to which tissue 201916 may be coupled prior to attachment of anvil 201804. In addition, the extended position of trocar 20190400 may also provide for easier attachment of anvil 201804 to trocar 201904. Trocar 201904 further includes a tapered distal tip. Such a tip may be capable of piercing through tissue and/or aiding the insertion of anvil 201804 on to trocar 201904, though the tapered distal tip is merely optional. For instance, in other versions trocar 201904 may have a blunt tip. In addition, or in the alternative, trocar 201904 may include a magnetic portion (not shown) which may attract anvil 201804 towards trocar 201904. Of course still further configurations and arrangements for anvil 201804 and trocar 201904 will be apparent to one of ordinary skill in the art in view of the teachings herein.

When anvil 201804 is coupled to trocar 201904, the distance between a proximal face of the anvil 201804 and a distal face of stapling head assembly 201802 defines a gap distance d. Trocar 201904 of the present example is translatable longitudinally relative to stapling head assembly 201802 via an adjusting knob 201812 (FIG. 24) located at a proximal end of actuator handle assembly 201808 (FIG. 24), as will be described in greater detail below. Accordingly, when anvil 201804 is coupled to trocar 201904, rotation of adjusting knob 201812 enlarges or reduces gap distance d by actuating anvil 201804 relative to stapling head assembly 201802. For instance, as shown sequentially in FIGS. 29A-29B, anvil 201804 is shown actuating proximally relative to actuator handle assembly 201808 from an initial, open position to a closed position, thereby reducing the gap distance d and the distance between the two portions of tissue 201916 to be joined. Once the gap distance d is brought within a predetermined range, stapling head assembly 201802 may be fired, as shown in FIG. 29C, to staple and sever tissue 201916 between anvil 201804 and stapling head assembly 201802. Stapling head assembly 201802 is operable to staple and sever tissue 201916 by a trigger of actuator handle assembly 201808, as will be described in greater detail below.

Still referring to FIGS. 29A-29C, a user sutures a portion of tissue 201916 about tubular member 201944 such that anvil head 201920 is located within a portion of the tissue 201916 to be stapled. When tissue 201916 is attached to anvil 201804, retaining clips 201924 and a portion of tubular member 201922 protrude out from tissue 201916 such that the user may couple anvil 201804 to trocar 201904. With tissue 201916 coupled to trocar 201904 and/or another portion of stapling head assembly 201802, the user attaches anvil 201804 to trocar 201904 and actuates anvil 201804 proximally towards stapling head assembly 201802 to reduce the gap distance d. Once instrument 201800 is within the operating range, the user then staples together the ends of tissue 201916, thereby forming a substantially contiguous tubular portion of tissue 201916.

Stapling head assembly 201802 of the present example is coupled to a distal end of shaft assembly 201806 and comprises a tubular casing 201926 housing a slidable staple driver 201910 and a plurality of staples 201902 contained within staple pockets 201928. Shaft assembly 201806 of the present example comprises an outer tubular member 201942 and a driver actuator 201908. Staples 201902 and staple pockets 201928 are disposed in a circular array about tubular casing 201926. In the present example, staples 201902 and staple pockets 201928 are disposed in a pair of concentric annular rows of staples 201902 and staple pockets 201928. Staple driver 201910 is operable to actuate longitudinally within tubular casing 201926 in response to rotation of actuator handle assembly 201808 (FIG. 24). As shown in FIGS. 29A-29C, staple driver 201910 comprises a flared cylindrical member having a trocar opening 201930, a central recess 201932, and a plurality of members 201914 disposed circumferentially about central recess 201932 and extending distally relative to shaft assembly 201806. Each member 201914 is configured to contact and engage a corresponding staple 201902 of the plurality of staples 201902 within staple pockets 201928. Accordingly, when staple driver 201910 is actuated distally relative to actuator handle assembly 201808, each member 201914 drives a corresponding staple 201902 out of its staple pocket 201928 through a staple aperture 201934 formed in a distal end of tubular casing 201926. Because each member 201914 extends from staple driver 201910, the plurality of staples 201902 is driven out of stapling head assembly 201802 at substantially the same time. When anvil 201804 is in the closed position, staples 201902 are driven into staple forming pockets 201936 to bend legs 201938 of the staples 201902, thereby stapling the material located between anvil 201804 and stapling head assembly 201808. FIG. 30 depicts by way of example staple 201902 driven by a member 201914 into a staple forming pocket 201928 of anvil 201804 to bend legs 201938.

The motorized circular stapling instrument 201800, 201502, 201532, 201610 described herein with reference to FIGS. 24-30 may be controlled using any of the control circuits described in connection with FIGS. 16-23. For example, the control system 470 described with reference to FIG. 16. Further, the motorized circular stapling instrument 201800, 201502, 201532, 201610 may be employed in a hub and cloud environment as described in connection with FIGS. 1-15.

Circular Stapler Control Algorithms

In various aspects, the present disclosure provides a powered stapling device that is configured with circular stapler control algorithms to adjust the force, advancement speed, and overall stroke of the cutting member of the device based on at least one sensed parameter of firing or clamping. In another aspect, the cutting member of the device is independently actuatable from both firing and closing. In yet another aspect, the sensed parameter may be a final tissue gap, force during closure, tissue creep stabilization, or force during firing. Still in other aspects, the knife actuation is capable of being run in either load control or stroke control with adjustable limits on the control parameter. Both maximum applicable force as well as overall total stroke range can be adjusted. The controlled parameter could have secondary limits on the non-controlled function. In yet another aspect, the advancement rate of the cutting member being adjustable to a predefined rate based on the conditions of the device at the start of cutting.

Adjustment of Cutting Parameters

In one aspect, a powered stapling device is configured to adjust the force, advancement speed, and overall stroke of the cutting member of the device based on at least one sensed parameter of firing or clamping. In one aspect, the cutting member of the device is independently actuatable from both firing and closing. In another aspect, the sensed parameter comprises the final tissue gap, force during closure, tissue creep stabilization, or force during firing. In one aspect, the knife actuation is configured to be run in either load control or stroke control with adjustable limits on the control parameter. For example, both maximum applicable force and overall total stroke range can be adjusted. The controlled parameter could have secondary limits on the non-controlled function. In one aspect, the advancement rate of the cutting member is adjustable to a predefined rate based on the conditions of the device at the start of cutting.

Adjustment of Closure Rate or Direction Based on Sensed Attachment

Figure 31:
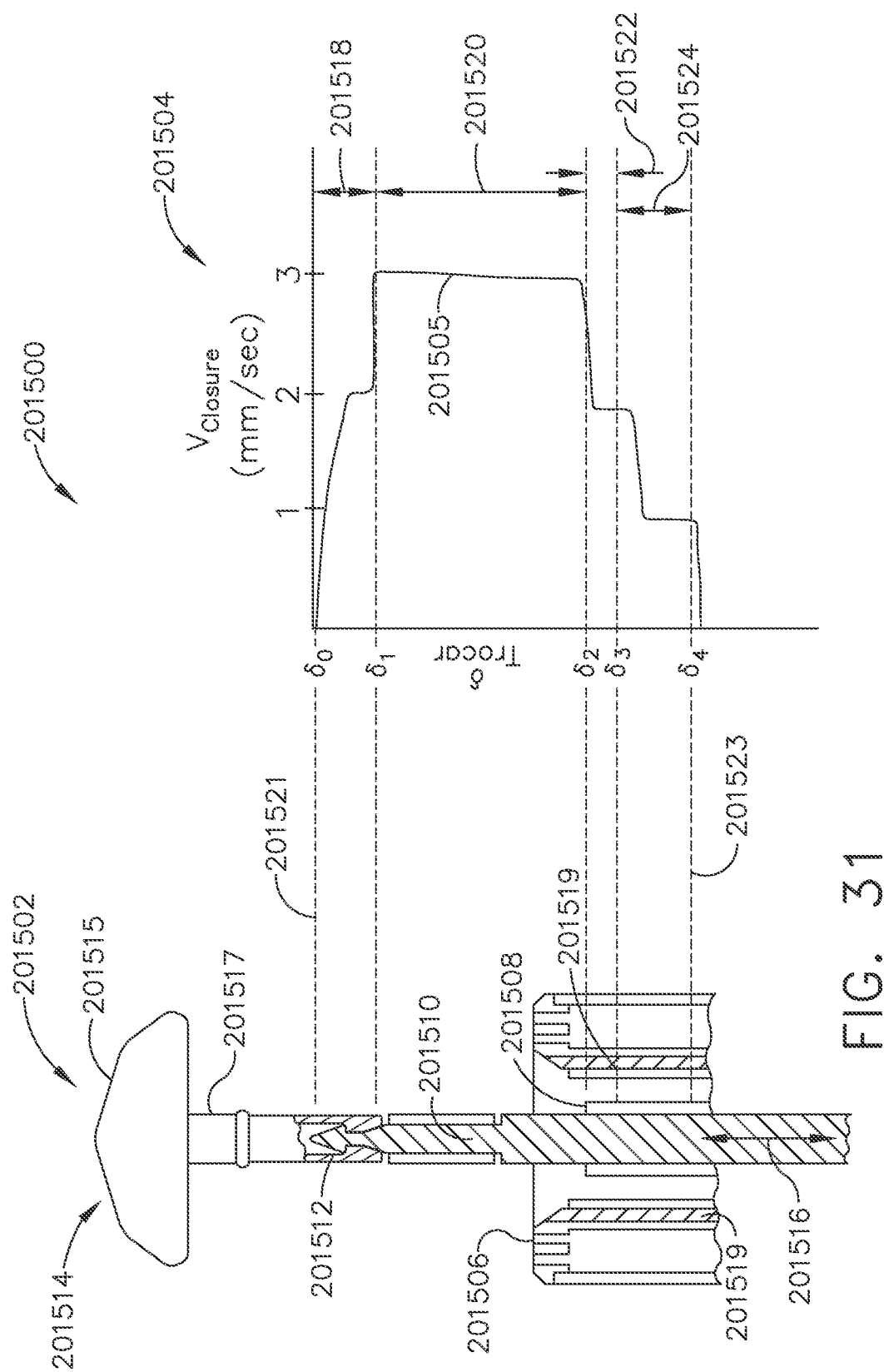
FIG. 31 is a diagram of graph and associated powered stapling device illustrating anvil closure rate adjustment at certain key points along a trocar's retraction stroke, in accordance with at least one aspect of the present disclosure.

In various aspects, the closure rate or direction of a circular stapler, or a combination thereof, can be adjusted based on the sensed attachment, relative to the fully attached state, of the anvil. In one aspect, the present disclosure provides a digitally enabled circular stapler algorithm for determining the variation the closure rate of the anvil at key locations of the trocar to ensure proper seating of the anvil on the trocar. FIG. 31 is a diagram 201500 of a powered stapling device 201502 and a graph 201504 illustrating the closure rate adjustment of an anvil 201514 portion of the powered stapling device 201502 at certain key points along the retraction stroke of a trocar 201510, in accordance with at least one aspect of the present disclosure. The powered stapling device 201502 is similar to the motorized circular stapling instrument 201800 described herein with reference to FIGS. 24-30, may be controlled using any of the control circuits described in connection with FIGS. 16-23, and may be employed in a hub and cloud environment as described in connection with FIGS. 1-15. The anvil 201514 includes an anvil head 201515 and an anvil shank 201517. The trocar 201510 can be advanced and retracted in the direction indicated by arrow 201516. In one aspect, the closure rate of the anvil 210514 can be adjusted at certain key points along the retraction stroke of the trocar 201510 to improve the final seating of the anvil 201514 on the trocar 201510 if the trocar 201510 is marginally attached but not fully attached to the anvil 201514.

The powered stapling device 201502, shown on the left side of FIG. 31, includes a circular stapling head assembly 201506 with a seating collar 201508 that receives the trocar 201510 therethrough. The trocar 201510 engages the anvil 201514 via a locking feature 201512. The trocar 210510 is movable, e.g., advanced and retracted, in the directions indicated by arrow 201516. A cutting element, such as a knife 201519, severs tissue when the circular stapling head assembly 201506 is driven towards the anvil 201514. In one aspect, the closure rate of the anvil 201514 can be adjusted at certain key points along the retraction stroke of the anvil 201510 in order to, for example, improve the final seating of the anvil 201514 on the trocar 201510 if the trocar 210510 is marginally attached but not fully attached to the anvil 201514. Accordingly, the closure rate of the anvil 201514 can be varied at key locations to ensure proper seating. The position or displacement of the trocar 210510 as it is advanced or retracted by a trocar actuator coupled to a motor, as previously described with reference to FIGS. 24-30, may be detected by a plurality of proximity sensors disposed along the displacement path of the trocar 210510. In some aspects, the position or displacement of the trocar 210510 may be tracked using the tracking system 480 (FIG. 16) or the position sensors 734, 784 (FIGS. 21, 23).

On the right side of FIG. 31, the graph 201504 illustrates the closure rate of the anvil 201514 as a function of the position of the trocar 201510 at certain key points, labeled as "$\delta$ Trocar" along the vertical axis and "$V_{closure}$ mm/sec" along the horizontal axis, in accordance with at least one aspect of the present disclosure. An anvil 201514 closure rate velocity profile curve 201505 is plotted as a function of the position of the trocar 201510. The closure rate of the anvil 201514 can be slow at a first zone 201518 to ensure proper attachment of the trocar 210510 to the anvil 201514, faster at a second zone 201520 during closure, slower again at a third zone 201522 to verify attachment, and then even slower at a fourth zone 201524 during application of a high closure load.

The anvil 201514 closure rate adjustment at certain key points along the trocar's 201510 retraction stroke improves the final seating of the anvil 201514 on the trocar 201510 if it marginally attached but not fully attached. At trocar 201510 position $\delta_0$ the anvil 201514 is in a fully open position 201521 and at trocar 201510 position $\delta_4$ the anvil 201514 is in a fully closed position 201523. Between the trocar 201510 fully open position 201521 $\delta_0$ and fully closed position $\delta_4$ the closure rate of the anvil 201514 is adjusted based on the position of the trocar 201510. For example, at the first zone 201518, as the trocar 201510 moves from the fully opened position 201521 $\delta_0$ to a first trocar 201510 position $\delta_1$, the closure rate of the anvil 201514 is slow (between 0-2 mm/sec) to ensure proper attachment of the anvil 201514 to the trocar 201510. At the second zone 201520, when the trocar 201510 moves from $\delta_1$ to $\delta_2$, the anvil 201514 is closed at a constant quick closure rate (3 mm/sec). When the trocar 201510 moves from $\delta_2$ to $\delta_3$ position, in the third zone 201522, the closure rate of the anvil 201514 is slowed to verify full attachment of the anvil 201514 to the trocar 201510. Finally, when the trocar 201510 moves from $\delta_3$ to $\delta_4$ position, in the fourth zone

201524, the closure rate of the anvil 201514 is slowed once again during high closure loads.

Figure 32:
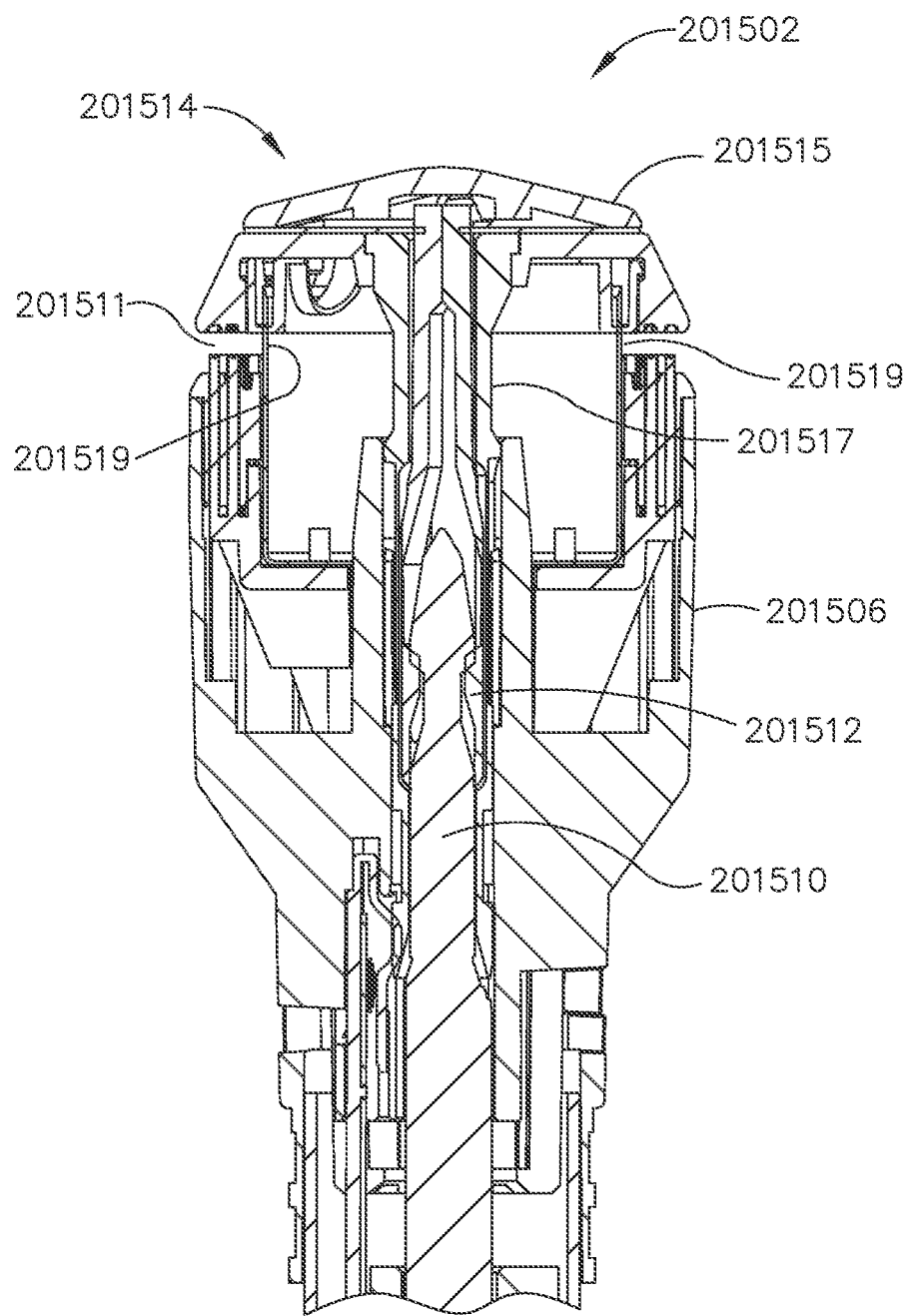
FIG. 32 is a view of a circular stapler, in accordance with at least one aspect of the present disclosure.

FIG. 32 is a section view of the powered stapling device 201502 shown in FIG. 31 in a closed configuration, e.g., the circular stapling head assembly 201506 advanced towards the anvil 201514. As shown in FIG. 32, the circular stapling head assembly 201506 and the trocar 201510 are shown in an advanced configuration to grasp tissue in the tissue gap 210511 defined between the anvil 201514 and the circular stapling head assembly 201506. As described herein, the trocar 201510 may be advanced or retracted by a motor coupled to, for example, a trocar actuator, as previously described with reference to FIGS. 24-30. A knife 201519 is employed to sever tissue captured between the anvil 201514 and the trocar 201510. The knife 201519 is coupled to a motor, which is configured to advance and retract the knife 201519. A control circuit is employed to control the motor and to control the rate of advancement/retraction of the trocar 201510 or the knife 201519 or a combination thereof.

Figure 33:
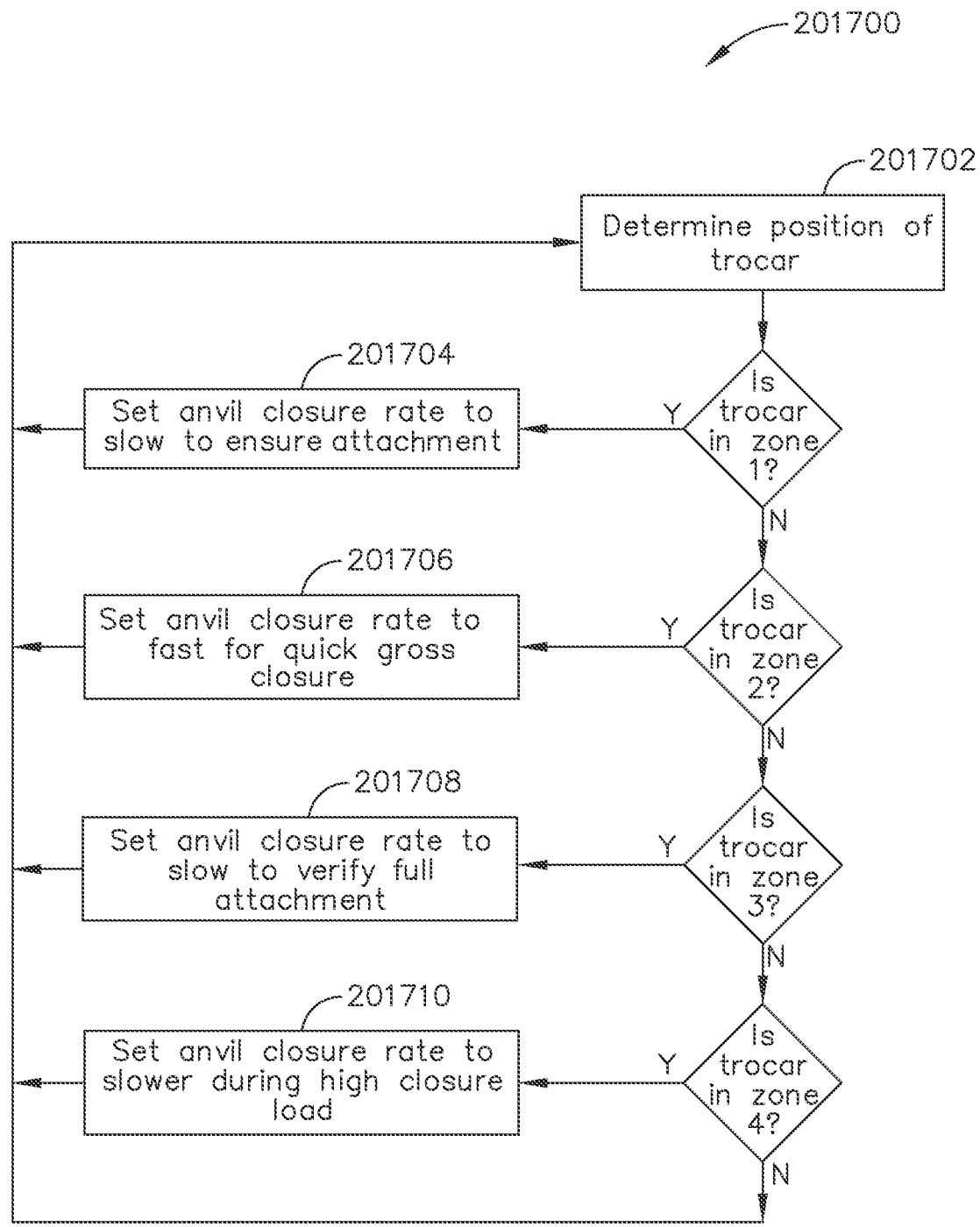
FIG. 33 is a logic flow diagram of a process depicting a control program or a logic configuration to adjust a closure rate of the anvil portion of the powered stapling device at certain key points along the retraction stroke of a trocar, in accordance with at least one aspect of the present disclosure.

FIG. 33 is a logic flow diagram of a process 201700 depicting a control program or a logic configuration to adjust a closure rate of the anvil 201514 portion of the powered stapling device 201502 at certain key points along the retraction stroke of a trocar 201510, in accordance with at least one aspect of the present disclosure. This process 201700 may be implemented with any of the control circuits described with reference to FIGS. 16-23. This process 201700 may be implemented in a hub or cloud computing environment described with reference to FIGS. 1-15, for example.

In particular, the process 201700 depicted in FIG. 33 will now be described with reference to the control circuit 760 of FIG. 22. The control circuit 760 determines 201702 the position of the trocar 201510 based on information received from position sensor 784. Alternatively, the position of the trocar 201510 may be determined based on information received from the sensors 788 or the timer/counter 781 circuit or a combination thereof. Based on the position of the trocar 201510, the control circuit 760 controls the closure rate of the anvil 201514 ($V_{closure}$ mm/sec) as a function of the position of the trocar 201510 at certain key points, in accordance with at least one aspect of the present disclosure. Accordingly, when the position of the trocar 201510 is located in a first zone 201518, where the anvil 201514 is attached to the trocar 201510, the process 201700 continues along the yes (Y) branch and the control circuit 760 sets 201704 the closure rate of the anvil 201514 to slow to ensure proper attachment of the trocar 210510 to the anvil 201514. Otherwise the process 201700 continues along the no (N) branch. When the position of the trocar 201510 is located in a second zone 201520, referred to as a quick gross closure zone, the process 201700 continues along the yes (Y) branch and the control circuit 760 sets 201706 the closure rate of the anvil 201514 to fast to rapidly close the anvil 201514. Otherwise the process 201700 continues along the no (N) branch. When the position of the trocar 201510 is located in a third zone 201522, referred to as a verification zone, the process continues along the yes (Y) branch and the control circuit 760 sets 201708 the closure rate of the anvil 201514 to slow to verify full attachment of the anvil 201514 to the trocar 201510. Otherwise the process 201700 continues along the no (N) branch. When the position of the trocar 201510 is located in a fourth zone 201524, referred to as a high closure load zone, the process 201700 continues along the yes (Y) branch and the control circuit 760 sets 201710 the closure rate of the anvil 201514 to a slower rate than in the previous verification zone 201522 during the application of a high closure load. Once the anvil 201514 is fully closed trocar 201510 to capture tissue therebetween, the control circuit 760 actuates the knife 201519 to sever the tissue.

Figure 34:
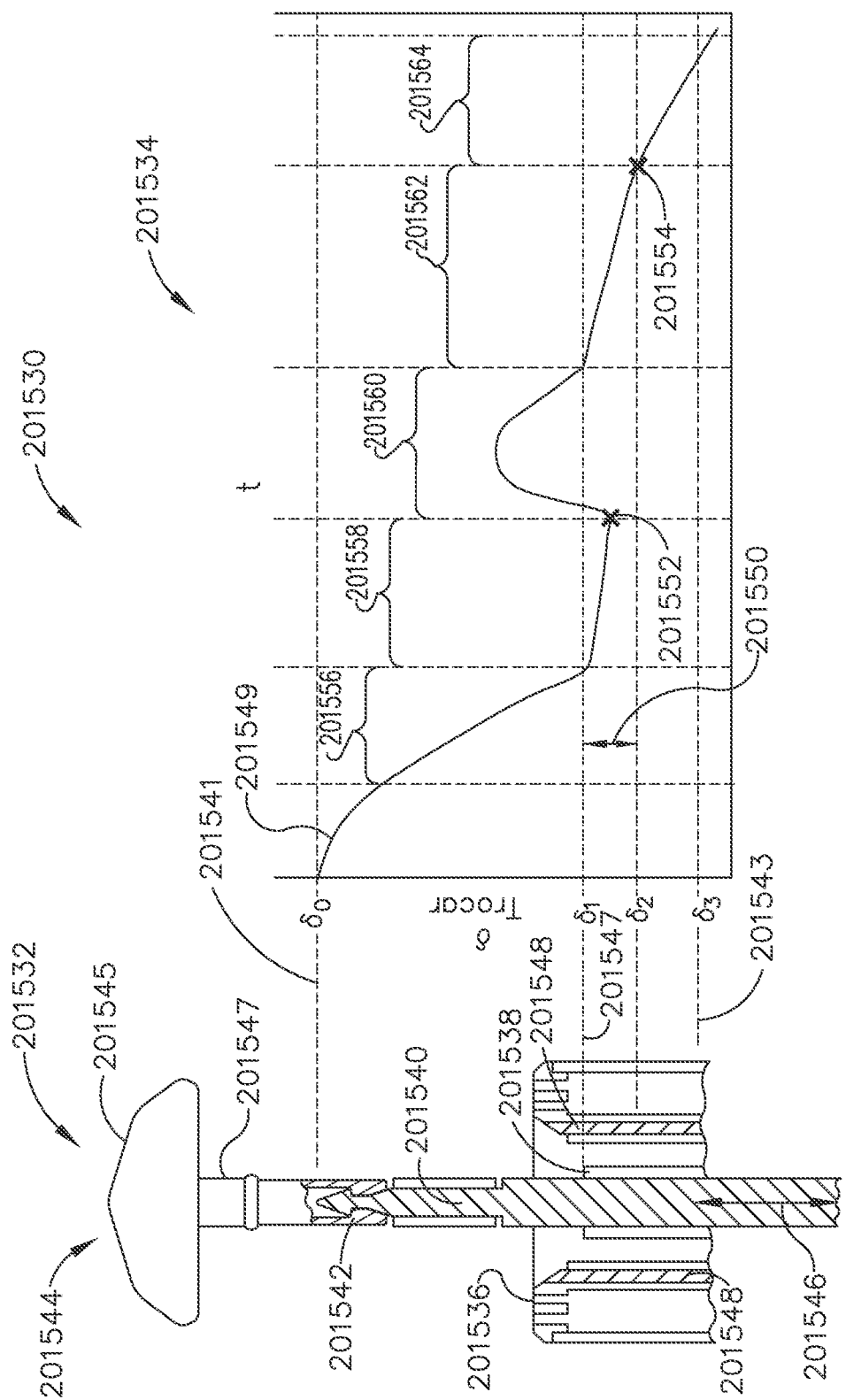
FIG. 34 is a diagram of graph and associated power stapling device diagram illustrating trocar position over time, in accordance with at least one aspect of the present disclosure.

In one aspect, the present disclosure provides a digitally enabled circular stapler adaptive algorithm for determining multi-directional seating motions on the trocar to drive the anvil into proper seating. FIG. 34 is a diagram 201530 of a powered stapling device 201532 and a graph 201534 illustrating detection of closure rates of the trocar 201540 and the anvil 201544, in accordance with at least one aspect of the present disclosure. The powered stapling device 201532 is similar to the motorized circular stapling instrument 201800 described herein with reference to FIGS. 24-30, may be controlled using any of the control circuits described in connection with FIGS. 16-23, and may be employed in a hub and cloud environment as described in connection with FIGS. 1-15. The anvil 201544 includes an anvil head 201545 and an anvil shank 201547. The trocar 201540 can be advanced and retracted in the direction indicated by arrow 201546. In one aspect, if the anvil shank 201547 is detected pulling loose from the trocar 201540, the powered stapling device 210530 could stop retraction or reverse and advance towards an open position 201541 until the instability of the anvil 201544 seating is resolved. If the anvil 201544 is pulled fully off, the powered stapling device 210530 could fully open 201541 indicating to the user to try re-attaching the anvil shank 201547 to the trocar 201540.

The powered stapling device 201532, shown on the left side of FIG. 34, includes a circular stapling head assembly 201536 with a seating collar 201538 that receives the trocar 201540 therethrough. The trocar 201540 engages the anvil 201544 via a locking feature 201542. The trocar 210540 is movable, e.g., advanced and retracted, in the directions indicated by arrow 201546. A cutting element, such as a knife 201548, severs tissue when the circular stapling head assembly 201536 is driven towards the anvil 201544.

In one aspect, the closure rates of the trocar 201540 and the anvil 201544 can be detected and any discrepancy between the closure rates of the two components could generate an automatic extension of the trocar 201540 and then retraction of the trocar 201540 in order to fully seat the anvil 201544 on the trocar 201540. In one aspect, any discrepancy between the closure rates of the trocar 201540 and the anvil 201544 may be provided to a control circuit or processor to operate a motor coupled to the trocar 201540 to generate an automatic extension of the trocar 201540 and then re-retraction in order to fully seat the anvil 201544 on the trocar 201540. If the anvil shank 201547 is detected pulling loose from the trocar 201540 the smart powered stapling device 201532 could stop retraction or even reverse and advance towards open until the instability of seating the anvil 201544 is resolved. If the anvil 201544 were pulled fully off it could even fully open indicating to the user to try re-attaching the anvil shank 201547 to the trocar 201540. As shown FIG. 34, the control algorithm can be configured to extend the trocar 201540 back towards the open position 201541 to reset the anvil 201544 if an anvil 201544 detachment is sensed, prior to then re-verifying attachment of the anvil 201544 and proceeding as normal upon confirming that the anvil 201544 is attached.

Accordingly, the system can be configured for multi-directional seating motions on the trocar 201540 to drive the anvil 201544 into proper seating. For example, if the anvil shank 201547 is detected as pulling loose from the trocar 201540, the smart powered stapling device 201530 could be configured to stop retraction or even reverse and advance towards open until the instability of seating the anvil 201544 is resolved. If the anvil 201544 were pulled fully off, the smart powered stapling device 201532 could even be configured to fully open, indicating to the user to try reattaching the anvil shank 201547 to the trocar 201540.

On the right side of FIG. 34, the graph 201534 illustrates the position of the trocar 201510 as a function of time at certain key points, labeled as "δ Trocar" along the vertical axis and "t" along the horizontal axis, in accordance with at least one aspect of the present disclosure. A trocar 201540 position profile curve 201549 is plotted as a function of time (t). With reference to the trocar 201540 position profile curve 201549, the trocar 201540 moves from a fully open position 201541 towards a fully closed position 201543 over a first period 201556 at a quick closure rate. During a second period 201558, the trocar 201540 moves into the verification zone 201547 where the anvil locking feature 201542 engages the seating collar 201538, at a slow rate to verify that the anvil locking feature 201542 has properly engaged the seating collar 201538. In the illustrated example, an anvil 201544 detached initiation is sensed at time 201552. Upon sensing that the anvil 201544 is detached, the trocar 201540 is advanced towards an open position and back over a third period 201560. The trocar 201540 then moves slowly during a fourth period 201562 until it is confirmed or verified that the anvil 201544 is attached to the trocar 201540 at time 201554. Thereafter, the trocar 201540 moves towards the closed position 201543 very slowly during a fifth period 201564 under high tissue load before the knife 201548 is advanced to sever the tissue captured between the anvil 201544 and the circular stapling head assembly 201536.

Figure 35:
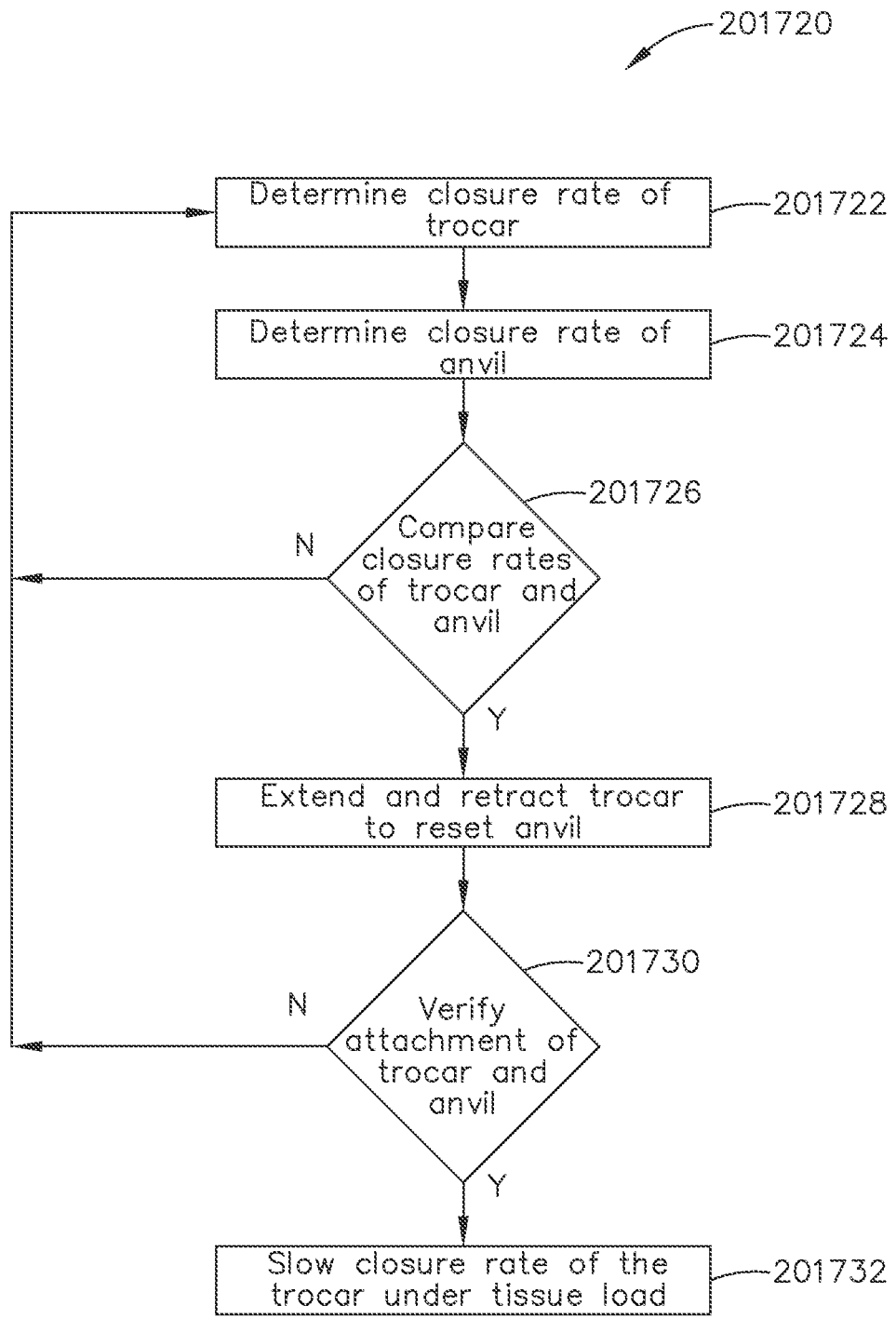
FIG. 35 is a logic flow diagram of a process depicting a control program or a logic configuration to detect multi-directional seating motions on the trocar to drive the anvil into proper seating, in accordance with at least one aspect of the present disclosure.

FIG. 35 is a logic flow diagram of a process 201720 depicting a control program or a logic configuration to detect multi-directional seating motions on the trocar 201540 to drive the anvil 201544 into proper seating, in accordance with at least one aspect of the present disclosure. This process 201720 may be implemented with any of the control circuits described herein with reference to FIGS. 16-23. This process 201720 may be implemented in a hub or cloud computing environment described with reference to FIGS. 1-15, for example.

In particular, the process 201720 depicted in FIG. 35 will now be described with reference to the control circuit 760 of FIG. 22. The control circuit 760 determines 201722 the closure rate of the trocar 201540 based on information received from position sensor 784. The control circuit 760 then determines 201724 the closure rate of the anvil 201544 based on information received from position sensor 784. Alternatively, the closure rate of the trocar 201540 or the anvil 201544 may be determined based on information received from the sensors 788 or the timer/counter 781 circuit or a combination thereof. The control circuit 760 compares 207126 the closure rates of the trocar 201540 and the anvil 201544. When there is no discrepancy between the closure rates of the trocar 201540 and the anvil 201544, the process 201720 continues along the no (N) branch and loops until there is a discrepancy between the closure rates of the trocar 201540 and the anvil 201544. When there is a discrepancy between the closure rates of the trocar 201540 and the anvil 201544, the process 201720 continues along the yes (Y) branch and the control circuit 760 extends and retracts 207128 the trocar 201540 to reset the anvil 201544. Subsequently, the process 201720 verifies 201130 the attachment of the trocar 201540 and anvil 201544. If the attachment is verified, the process 201720 continues along the yes (Y) branch and the control circuit 760 slows 207132 the closure rate of the trocar 201540 under tissue load. If the attachment is not verified, the process 201720 continues along the no (N) branch and loops until the attachment of the trocar 201540 to the anvil 201544 is verified. Once the anvil 201544 is fully closed on the trocar 201540 to capture tissue therebetween, the control circuit 760 actuates the knife 201548 to sever the tissue.

Adjustment of Knife Speed/End Points Based on Tissue Parameters

In various aspects, the knife speed of a circular stapler and end points can be adjusted based on the sensed toughness or thickness of the tissue between the anvil and cartridge. Accordingly, the circular stapler control algorithm can be configured to detect the tissue gap and force-to-fire to adjust the knife stroke and speed. In one aspect, the present disclosure provides a digitally enabled circular stapler adaptive algorithm for detecting tissue gap and force-to-fire to adjust knife stroke and knife speed, in accordance with at least one aspect of the present disclosure.

Figure 37:
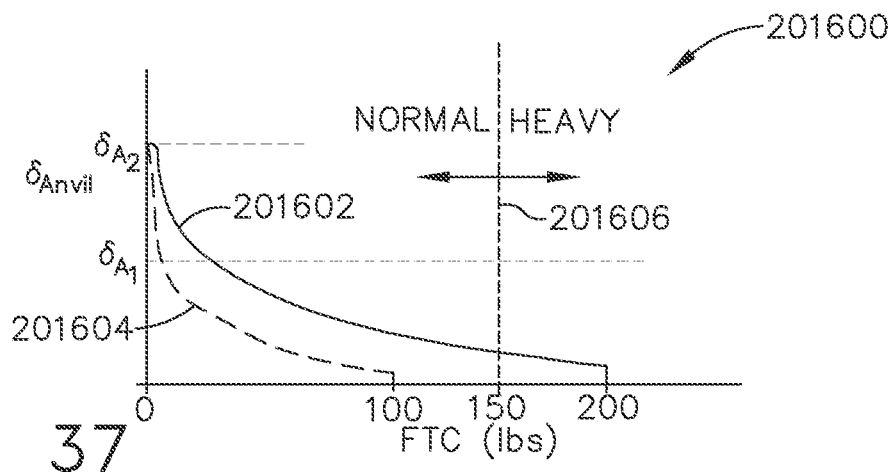
FIG. 37 is a graphical representation of anvil displacement ($\delta_{Anvil}$) along the vertical axis as a function of force to close (FTC) a clamp along the horizontal axis, in accordance with at least one aspect of the present disclosure.
Figure 36:
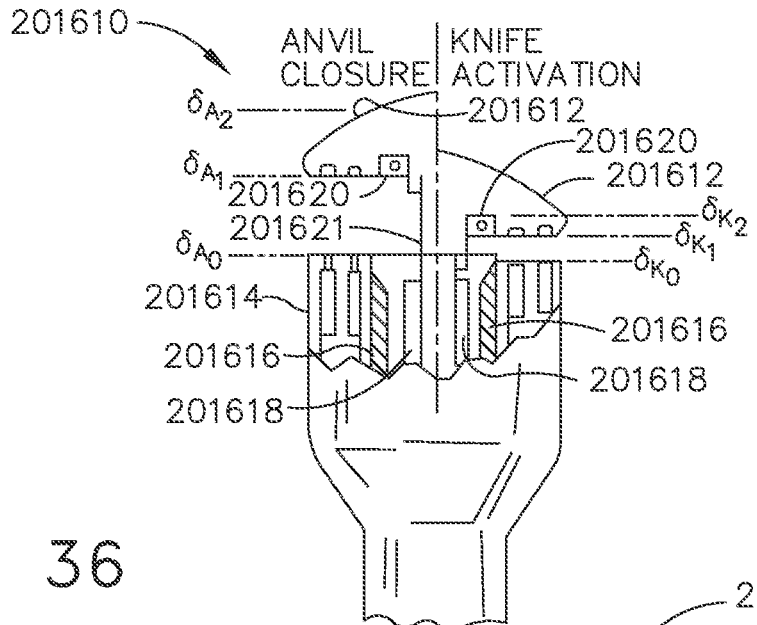
FIG. 36 is a partial schematic diagram of a circular powered stapling device showing anvil closure on the left side and knife 201616 actuation on the right side, in accordance with at least one aspect of the present disclosure.
Figure 38:
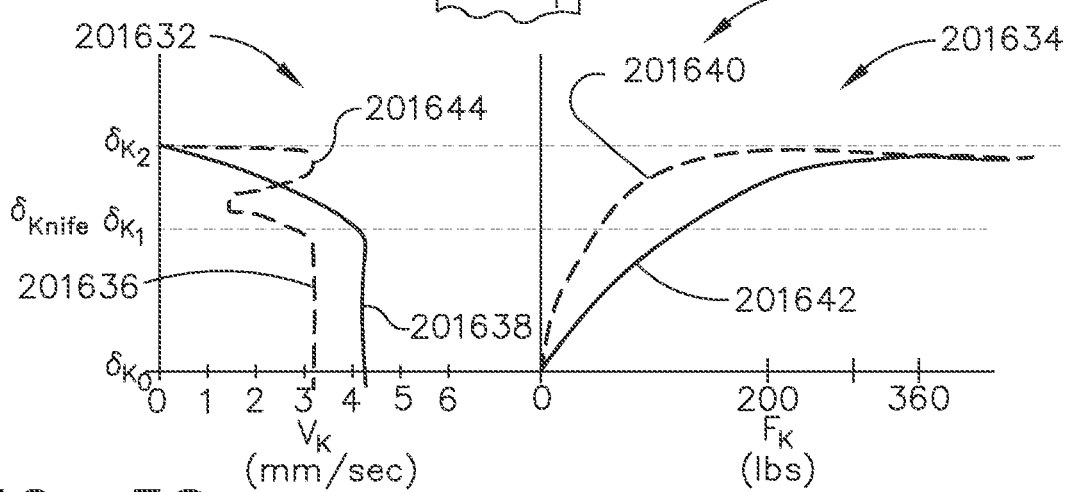
FIG. 38 is a graphical representation 201630 of knife 201616 displacement ($\delta_{Knife}$) along the vertical axis as a function of knife 201616 velocity ($V_K$ mm/sec) along the horizontal axis on the left and also as a function of knife 201616 force ($F_K$ lbs) along the horizontal axis on the right, in accordance with at least one aspect of the present disclosure.

Generally, FIGS. 36-38 represent a circular powered stapling device 201610 and a series of graphs depicting force-to-close (FTC) a clamp relative to the position of the anvil 201612 ($\delta_{Anvil}$) and knife 201616 velocity ($V_K$) and knife 201616 force ($F_K$) relative to the position of the knife 201616 ($\delta_{Knife}$), in accordance with at least one aspect of the present disclosure. Using sensed data at different points along length of the shank 201621, a control algorithm can generate a map of tissue gap or reaction force vector of the anvil 201612, monitoring for a high or low side when compressed on tissue. When firing, the system measures forces acting on a compression element 201620 comprising a force sensor and adjusts to act evenly along the force vector of the shank to provide even and complete cutting.

In particular, FIG. 36 is a partial schematic diagram of a circular powered stapling device 201610 showing anvil 201612 closure on the left side and knife 201616 actuation on the right side, in accordance to at least one aspect of the present disclosure. The circular powered stapling device 201610 comprises an anvil 201612 that is movable from a fully open position $\delta_{A2}$ to a fully closed position $\delta_{A0}$. An intermediate position $\delta_{A1}$ represents the point at which the anvil 201612 contacts tissue located between the anvil 201612 and the circular stapler 201614. One or more position sensors located along the length of the anvil shank 201621 monitor the position of the anvil 201612. In one aspect, the position sensor may be located within the seating collar 201618. The compression element 201620 may comprise a force sensor, such as a strain gauge for example, to monitor the force applied to the tissue and to detect the point of initial contact of the anvil 201612 with the tissue, shown as intermediate position $\delta_{A1}$. The position sensor and the force sensor interface with any of the control circuits described herein with reference to FIGS. 16-23, for example, which implement the circular stapler control algorithm. The circular powered stapling device 201610 also comprises a movable cutting element such as a knife 201616 that is movable from a fully retracted position $\delta_{A0}$ to a fully extended position $\delta_{A2}$ to achieve a complete tissue cut. The intermediate position $\delta_{A1}$ of the knife 201616 represents the point at which the knife 201616 contacts with the compression element 201620 comprising a strain gauge or other contact or proximity sensor.

The power stapling device 201610 includes motors, sensors, and control circuits as described herein in connection with FIGS. 16-30. The motors are controlled by the control circuits to move the anvil 201612 and the knife 201616. One or more position sensors located on the power stapling device 201610 provide the position of the anvil 201612 and the knife 201616 to the control circuit. Additional sensors such as force sensors 201620 also provide tissue contact and force acting on the anvil 201612 and the knife 201616 to the control circuit. The control circuit employs the position of the anvil 201612, the position of the knife 201616, initial tissue contact, or force acting of the anvil 201612 or knife 201616 to implement the circular stapler control algorithm described hereinbelow in connection with FIG. 39.

FIG. 37 is a graphical representation 201600 of anvil 201612 displacement ($\delta_{Anvil}$) along the vertical axis as a function of force-to-close (FTC) a clamp along the horizontal axis, in accordance with at least one aspect of the present disclosure. The vertical line represents a FTC threshold 201606 that indicates tissue toughness. The left side of the FTC threshold 201606 represents tissue having normal toughness and the right side of the FTC threshold 201606 represents tissue having heavy toughness. As the anvil 201612 is retracted from the fully open position $\delta_{A2}$ to the intermediate position $\delta_{A1}$, where the anvil 201612 initially contacts tissue, the FTC is substantially low (~0). As the anvil 201612 continues closing past this point towards the circular stapler 201614 to the fully retracted position $\delta_{A0}$ minus the compressed tissue thickness, the FTC is nonlinear. Each tissue type from normal to heavy toughness will produce a different FTC curve. For example, the first FTC curve 201604, shown in broken line, spans from ~0 to ~100 lbs., where the maximum FTC is below the FTC threshold 201606. The second FTC curve 201602, shown in solid line, spans from ~0 to ~200 lbs., where the maximum FTC exceeds the FTC threshold 201606. As previously discussed, the FTC is measured by force sensors located in the compression element 201620 and coupled to the control circuit.

FIG. 38 is a graphical representation 201630 of knife 201616 displacement ($\delta_{Knife}$) along the vertical axis as a function of knife 201616 velocity ($V_K$ mm/sec) along the horizontal axis on the left and also as a function of knife 201616 force ($F_K$ lbs) along the horizontal axis on the right, in accordance with at least one aspect of the present disclosure. On the left is a graphical representation 201632 of knife 201616 displacement ($\delta_{Knife}$) along the vertical axis as a function of knife 201616 velocity ($V_K$ mm/sec) along the horizontal axis. On the right is a graphical representation 201634 of knife 201616 displacement ($\delta_{Knife}$) along the vertical axis as a function of knife 201616 force ($F_K$ lbs) along the horizontal axis. The curves in dashed line 201638, 20142 in each of the graphical representations 201632, 201634 represent tissue of normal toughness whereas the curves in solid line 201636, 201640 represent tissue of heavy toughness.

Turning to the graphical representation 201632 on the left, for normal tissue toughness, as shown by the normal tissue knife velocity profile 201638, the initial velocity of the knife 201616 for normal tissue toughness starts at a first velocity, e.g., just over 4 mm/sec, at the initial knife position $\delta_{K0}$. The knife 201616 continues at that velocity until it reaches knife position $\delta_{K1}$ where the knife 201616 contacts tissue and slows the velocity of the knife 201616 as it cuts through the tissue until the knife 201616 reaches knife position $\delta_{K2}$ indicating a complete cut and the control circuit stops the motor and hence stops the knife 201616. Turning to the graphical representation 201634 on the right, for normal tissue toughness, as shown by the normal tissue knife force curve 201642, the force acting on the knife 201616 is 0 lbs. at the initial knife position $\delta_{K0}$ and varies nonlinearly until the knife 201616 reaches knife position $\delta_{K2}$ until the cut is complete.

Turning to the graphical representation 201632 on the left, for heavy tissue toughness, as shown by the heavy tissue knife velocity profile 201636, the initial velocity of the knife 201616 for heavy tissue toughness starts at a second velocity, e.g., just over 3 mm/sec, which is lower relative to the first velocity, at the initial knife position $\delta_{K0}$, which is less than the initial velocity for normal tissue toughness. The knife 201616 continues at that velocity until it reaches knife position $\delta_{K1}$ where the knife 201616 contacts tissue. At this point the velocity of the knife 201616 starts to slow down nonlinearly as it cuts through the tissue for a short displacement of the knife 201616. The control circuit detects that the knife 201616 contacted tissue and in response increases the velocity of the motor to increase the velocity of the knife 201616, e.g., to the initial velocity until the knife 201616, until the knife 201616 reaches position $\delta_{K2}$ indicating a complete cut and the control circuit stops the motor and hence stops the knife 201616. This is shown as velocity spike 201644 to improve cutting of tissue of heavy toughness. Turning to the graphical representation 201634 on the right, for heavy tissue toughness, as shown by the heavy tissue knife force curve 201640, the force acting on the knife 201616 is 0 lbs. at the initial knife position $\delta_{K0}$ and varies nonlinearly until the knife 201616 reaches knife position $\delta_{K2}$ and the cut is complete. A comparison of the normal and heavy tissue knife force curves 201640, 201642 shows that, with lower velocity and adding the velocity spike 201644 shortly after tissue contact with the knife 201616, the knife 201616 experiences a lower force when cutting tissue of heavy toughness than it experiences when cutting tissue of normal toughness.

Figure 39:
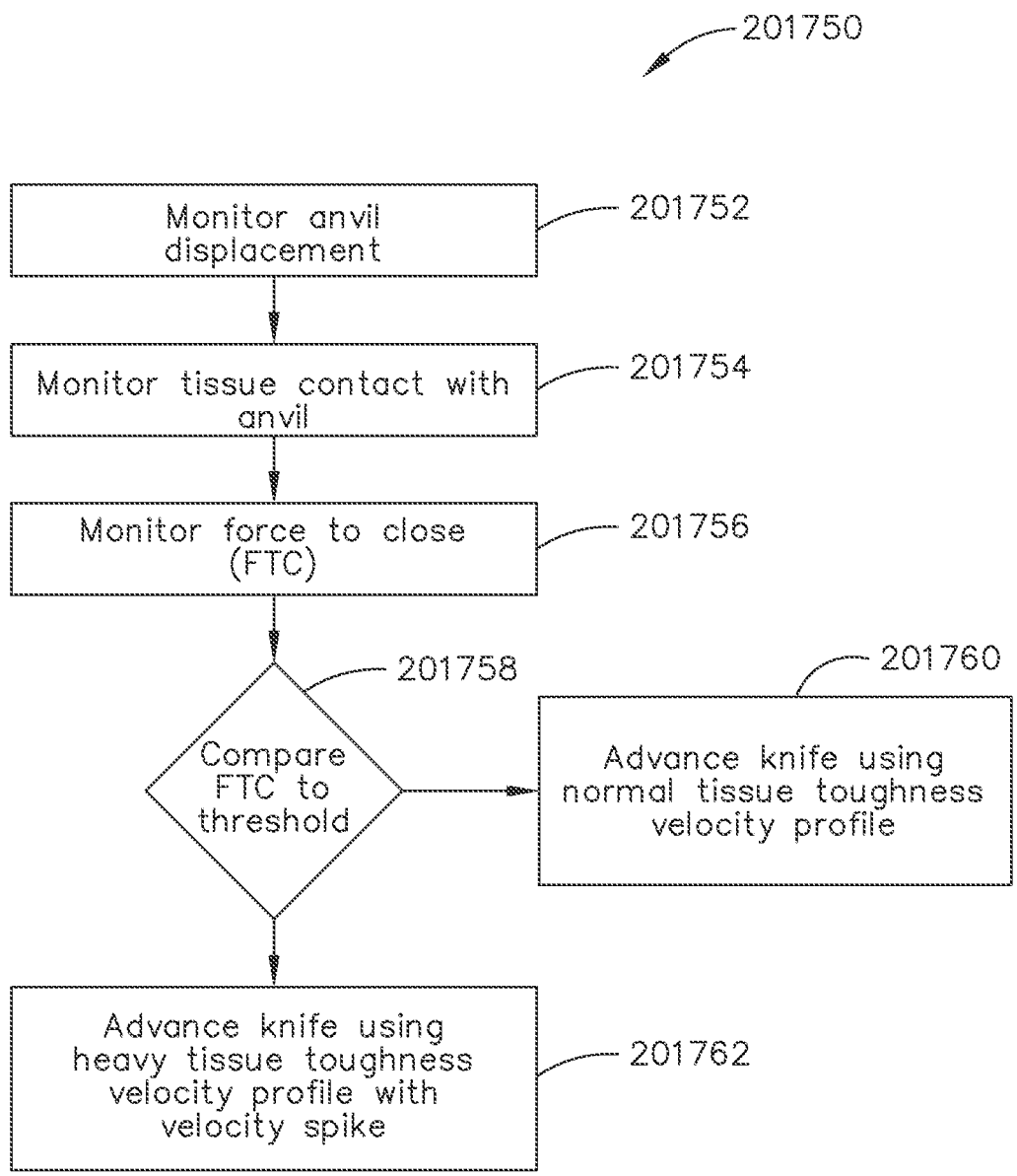
FIG. 39 is a logic flow diagram of a process depicting a control program or a logic configuration to detect the tissue gap and force-to-fire to adjust the knife stroke and speed, in accordance with at least one aspect of the present disclosure.

FIG. 39 is a logic flow diagram of a process 201720 depicting a control program or a logic configuration to detect the tissue gap and force-to-fire to adjust the knife stroke and speed, in accordance with at least one aspect of the present disclosure. This process 201750 may be implemented with any of the control circuits described with reference to FIGS. 16-23. This process 201750 may be implemented in a hub or cloud computing environment described with reference to FIGS. 1-15, for example.

In particular, the process 201750 depicted in FIG. 39 will now be described with reference to the control circuit 760 of FIG. 22 and the circular powered stapling device 201610 shown in FIGS. 36-38. The control circuit 760 monitors 201752 the displacement of the anvil 201612 based on position feedback received from the position sensor 784. As previously discussed, in one aspect, the position sensor 784 may be embedded in the shank 201612 of the anvil 201612. As the anvil 201612 is displaced, the control circuit 760 monitors 201754 contact of the anvil 201612 with tissue positioned between the anvil 201612 and the circular stapler 201614. In one aspect, tissue contact may be provided by a force sensor embedded in the compression element 201620. The force sensor is represented as the sensors 788 element of the surgical instrument 790 shown in FIG. 22. The force sensor 788 is employed to monitor 201756 the force-to-close (FTC) a clamp, which is the closing force of the anvil 201612 onto the tissue positioned between the anvil 201612 and the circular stapler 201614. The control circuit 760 compares 201758 the FTC to a predetermined threshold. When the FTC is below the predetermined threshold, the control circuit 760 sets the velocity of the motor 754 to advance 201760 the knife 201616 using a normal tissue toughness velocity profile 201638 as shown in FIG. 38.

When the FTC is above the predetermined threshold, the control circuit 760 sets the velocity of the motor 754 to advance 201762 the knife 201616 using a heavy tissue toughness velocity profile 201636 with a velocity spike 201644 as shown in FIG. 38.

Figure 40:
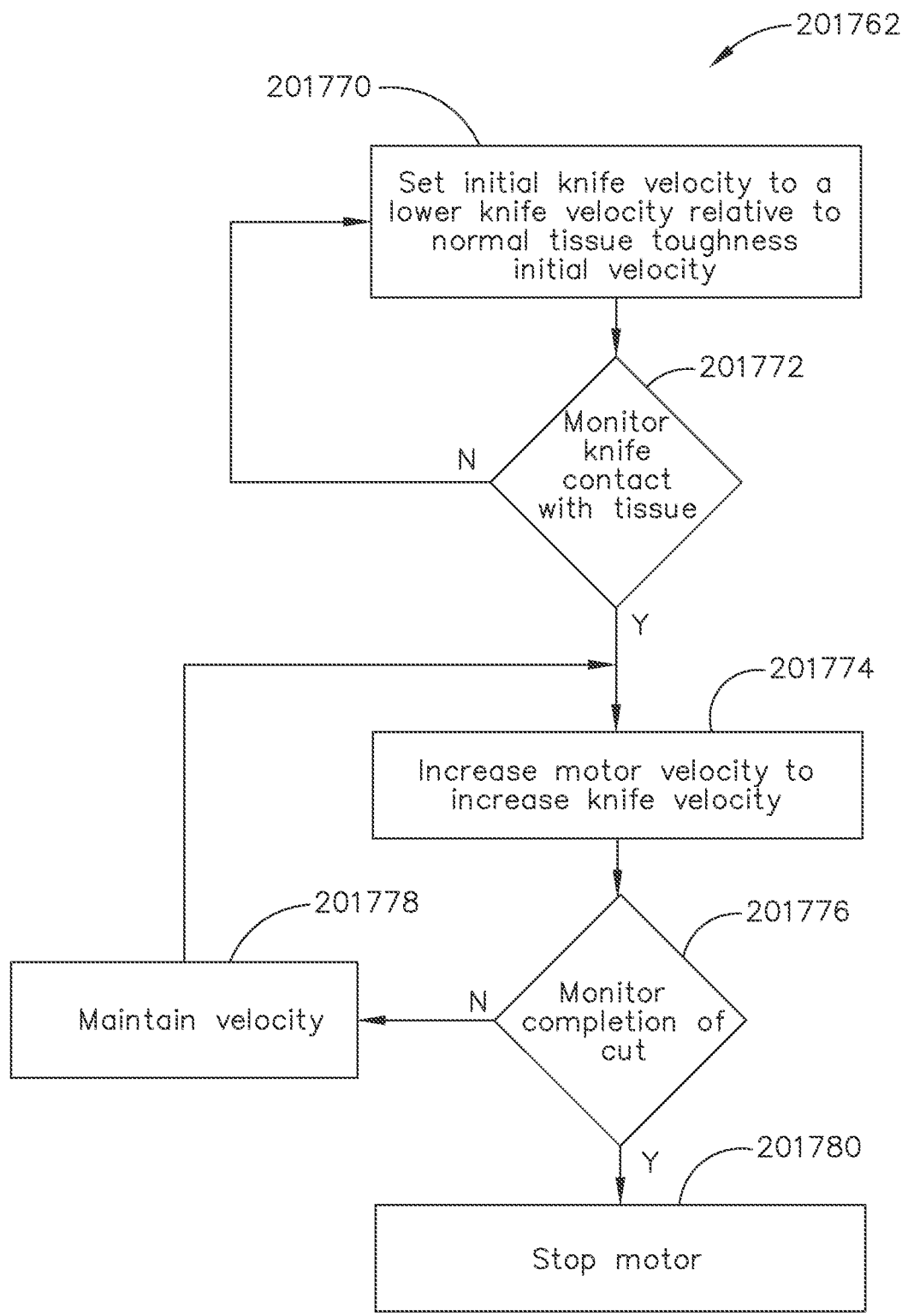
FIG. 40 is a logic flow diagram of a process depicting a control program or a logic configuration to advance the knife 201616 under a heavy tissue toughness velocity profile with a velocity spike as shown in FIG. 38, in accordance with at least one aspect of the present disclosure.

FIG. 40 is a logic flow diagram of a process 201762 depicting a control program or a logic configuration to advance 201762 the knife 201616 under a heavy tissue toughness velocity profile 201636 with a velocity spike 201644 as shown in FIG. 38, in accordance with at least one aspect of the present disclosure. This process 201762 may be implemented with any of the control circuits described with reference to FIGS. 16-23. This process 201750 may be implemented in a hub or cloud computing environment described with reference to FIGS. 1-15, for example.

In particular, the process 201762 depicted in FIG. 40 will now be described with reference to the control circuit 760 of FIG. 22 and the circular powered stapling device 201610 shown in FIGS. 36-38. When heavy tissue toughness is detected, the control circuit 760 sets 201770 the initial velocity of the knife 201616 a lower knife velocity relative to the knife velocity used for cutting normal tissue toughness. In one aspect, a slower knife velocity in heavy tissue toughness conditions promotes a better cut. The control circuit 760 monitors 201772 when the knife 201616 contacts the tissue. As previously discussed, tissue contact may be detected by a force sensor embedded in the compression element 201620. As shown in FIG. 38, when the knife 201616 contacts tissue the knife 201616 naturally slows down. Accordingly, once the control circuit 760 detects that the knife 201616 has contacted tissue, the tissue contact is detected, the control circuit 760 increases 201774 the velocity of the motor 754 to increase the velocity of the knife 201616 cutting through the tissue. The control circuit 760 monitors 201776 the completion of the cut and maintains 201778 the velocity of the motor 740 until completion of the cut is detected and then stops 201780 the motor 740.

Various aspects of the subject matter described herein are set out in the following numbered examples:

Example 1. A surgical stapling instrument comprising: an end effector configured to clamp a tissue; a cutting member; a motor coupled to the cutting member, the motor configured to move the cutting member between a first position and a second position; and a control circuit coupled to the motor, the control circuit configured to: sense a parameter associated with clamping of the end effector; and control the motor to adjust a torque applied to the cutting member by the motor.

Example 2. The surgical stapling instrument of Example 1, wherein the cutting member is independently actuatable from the end effector.

Example 3. The surgical stapling instrument of any one of Examples 1-2, wherein the parameter comprises a tissue gap, force during closure of the end effector, tissue creep stabilization, or force during firing, or any combination thereof.

Example 4. The surgical stapling instrument of any one of Examples 1-3, wherein the control circuit is configured to control the motor to drive the cutting member in either a load control mode or a stroke control mode according to an adjustable control parameter.

Example 5. The surgical stapling instrument of any one of Examples 1-4, wherein the control circuit is configured to control an advancement rate at which the motor drives the cutting member according to initial conditions as the motor begins driving the cutting member from the first position.

Example 6. The surgical instrument of any one of Examples 1-5, wherein the control circuit is configured to control the motor to adjust a speed at which the motor drives the cutting member.

Example 7. The surgical instrument of any one of Examples 1-6, wherein the control circuit is configured to control the motor to adjust a distance to which the motor drives the cutting member according to the parameter.

Example 8. The surgical instrument of any one of Examples 1-7, wherein the control circuit is configured to control the motor to adjust any combination of the torque, the speed, or the distance.

Example 9. A surgical stapling instrument comprising: an end effector configured to clamp a tissue; a cutting member; a motor coupled to the cutting member, the motor configured to move the cutting member between a first position and a second position; and a control circuit coupled to the motor, the control circuit configured to: sense a parameter associated with firing of the cutting member; and control the motor to adjust a torque applied to the cutting member by the motor.

Example 10. The surgical stapling instrument of Example 9, wherein the cutting member is independently actuatable from the end effector.

Example 11. The surgical stapling instrument of any one of Examples 9-10, wherein the parameter comprises a tissue gap, force during closure of the end effector, tissue creep stabilization, or force during firing, or any combination thereof.

Example 12. The surgical stapling instrument of any one of Examples 9-11, wherein the control circuit is configured to control the motor to drive the cutting member in either a load control mode or a stroke control mode according to an adjustable control parameter.

Example 13. The surgical stapling instrument of any one of Examples 9-12, wherein the control circuit is configured to control an advancement rate at which the motor drives the cutting member according to initial conditions as the motor begins driving the cutting member from the first position.

Example 14. The surgical instrument of any one of Examples 9-13, wherein the control circuit is configured to control the motor to adjust a speed at which the motor drives the cutting member.

Example 15. The surgical instrument of any one of Examples 9-14, wherein the control circuit is configured to control the motor to adjust a distance to which the motor drives the cutting member according to the parameter.

Example 16. The surgical instrument of any one of Examples 9-15, wherein the control circuit is configured to control the motor to adjust any combination of the torque, the speed, or the distance.

Example 17. A powered stapling device, comprising: a circular stapling head assembly; an anvil; a trocar coupled to the anvil and coupled to a motor, wherein the motor in configured to advance and retract the trocar; and a control circuit coupled to the motor, wherein the control circuit is configured to: determine a position of the trocar in one of a plurality of zones; and set an anvil closure rate based on the determined position of the trocar.

Example 18. The powered stapling device of Example 17, wherein the plurality of zones comprises: a first zone during attachment of the trocar to the anvil; a second zone during retraction of the trocar and closure of the anvil; a third zone during verification of attachment of the trocar to the anvil; and a fourth zone during application of a high closure load.

Example 19. The powered stapling device of any one of Examples 17-18, wherein the control circuit is configured to:

set the closure rate of the anvil to a first velocity when the trocar is in the first zone to ensure proper attachment of the trocar to the anvil; set the closure rate of the anvil to a second velocity, which is greater than the first velocity, when the trocar is in the second position during the retraction of the trocar and the closure of the anvil; set the closure rate of the anvil to a third velocity, which is less than the second velocity, to verify attachment of the trocar to the anvil; set the closure rate of the anvil to a fourth velocity, which is less than the third velocity, when the trocar is the fourth zone during application of a high closure load.

Example 20. The powered stapling device of any one of Examples 17-19, wherein the control circuit is configured to: determine the closure rate of the trocar; determine the closure rate of the anvil; compare the closure rate of the trocar to the closure rate of the anvil to determine a difference between the closure rate of the trocar to the closure rate of the anvil; and at a difference greater than a predetermined value, extend and retract the trocar to reset the anvil.

Example 21. The powered stapling device of any one of Examples 17-20, wherein the control circuit is configured to verify attachment of the trocar to the anvil and to slow the closure rate of the trocar under tissue load.

Example 22. The powered stapling device of any one of Examples 17-21, further comprising: a knife coupled to the motor; a sensor located on the anvil, wherein the sensor is configured to detect tissue contact and force applied to the anvil, wherein the sensor is coupled to the anvil, wherein the control circuit is configured to: monitor anvil displacement; monitor tissue contact with the anvil; monitor a force to close of the anvil; compare the force to close to a predetermined threshold; and set a first initial knife velocity and advance the knife at a first velocity profile suitable for cutting normal tissue toughness when the force to close is less than the predetermined threshold; or set a second initial knife velocity and advance the knife at a second velocity profile suitable for cutting heavy tissue toughness when the force to close is greater than or equal to the predetermined threshold.

Example 23. The powered stapling device of any one of Examples 17-22, wherein to advance the knife at the second velocity profile, the control circuit is further configured to: set the second initial knife velocity to a velocity that is less than the first initial knife velocity; monitor knife contact with tissue; increase motor velocity to increase knife velocity when tissue contact is detected; monitor completion of cut; and stop the motor when completion of cut is detected.

While several forms have been illustrated and described, it is not the intention of Applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. Those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution.

Instructions used to program logic to perform various disclosed aspects can be stored within a memory in the system, such as dynamic random access memory (DRAM), cache, flash memory, or other storage. Furthermore, the instructions can be distributed via a network or by way of other computer readable media. Thus a machine-readable medium may include any mechanism for storing or transmitting information in a form readable by a machine (e.g., a computer), but is not limited to, floppy diskettes, optical disks, compact disc, read-only memory (CD-ROMs), and magneto-optical disks, read-only memory (ROMs), random access memory (RAM), erasable programmable read-only memory (EPROM), electrically erasable programmable read-only memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, etc.). Accordingly, the non-transitory computer-readable medium includes any type of tangible machine-readable medium suitable for storing or transmitting electronic instructions or information in a form readable by a machine (e.g., a computer).

As used in any aspect herein, the term "control circuit" may refer to, for example, hardwired circuitry, programmable circuitry (e.g., a computer processor including one or more individual instruction processing cores, processing unit, processor, microcontroller, microcontroller unit, controller, digital signal processor (DSP), programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein "control circuit" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

As used in any aspect herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

As used in any aspect herein, the terms "component," "system," "module" and the like can refer to a computer-related entity, either hardware, a combination of hardware and software, software, or software in execution.

As used in any aspect herein, an "algorithm" refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

A network may include a packet switched network. The communication devices may be capable of communicating with each other using a selected packet switched network communications protocol. One example communications protocol may include an Ethernet communications protocol which may be capable permitting communication using a Transmission Control Protocol/Internet Protocol (TCP/IP). The Ethernet protocol may comply or be compatible with the Ethernet standard published by the Institute of Electrical and Electronics Engineers (IEEE) titled "IEEE 802.3 Standard", published in December, 2008 and/or later versions of this standard. Alternatively or additionally, the communication devices may be capable of communicating with each other using an X.25 communications protocol. The X.25 communications protocol may comply or be compatible with a standard promulgated by the International Telecommunication Union-Telecommunication Standardization Sector (ITU-T). Alternatively or additionally, the communication devices may be capable of communicating with each other using a frame relay communications protocol. The frame relay communications protocol may comply or be compatible with a standard promulgated by Consultative Committee for International Telegraph and Telephone (CCITT) and/or the American National Standards Institute (ANSI). Alternatively or additionally, the transceivers may be capable of communicating with each other using an Asynchronous Transfer Mode (ATM) communications protocol. The ATM communications protocol may comply or be compatible with an ATM standard published by the ATM Forum titled "ATM-MPLS Network Interworking 2.0" published August 2001, and/or later versions of this standard. Of course, different and/or after-developed connection-oriented network communication protocols are equally contemplated herein.

Unless specifically stated otherwise as apparent from the foregoing disclosure, it is appreciated that, throughout the foregoing disclosure, discussions using terms such as "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures or characteristics may be combined in any suitable manner in one or more aspects.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

The invention claimed is:

1. A powered stapling device, comprising:
    a circular stapling head assembly;
    an anvil;
    a trocar coupled to the anvil and coupled to a motor, wherein the motor is configured to advance and retract the trocar; and
    a control circuit coupled to the motor, wherein the control circuit is configured to:
        determine a position of the trocar in one of a plurality of zones;
        set an anvil closure rate based on the determined position of the trocar;
        determine a trocar closure rate;
        determine the anvil closure rate;
        compare the trocar closure rate to the anvil closure rate to determine a difference between the trocar closure rate and the anvil closure rate; and
        for the difference being greater than a predetermined value, extend and retract the trocar to reset the anvil.

2. The powered stapling device of claim 1, wherein the plurality of zones comprises:
    a first zone corresponding to an attachment of the trocar to the anvil;
    a second zone corresponding to a retraction of the trocar and a closure of the anvil;
    a third zone corresponding to a verification of the attachment of the trocar to the anvil; and
    a fourth zone corresponding to an application of a high closure load.

3. The powered stapling device of claim 2, wherein the control circuit is further configured to:
    set the anvil closure rate to a first velocity when the trocar is in the first zone;
    set the anvil closure rate to a second velocity, which is greater than the first velocity, when the trocar is in the second zone during the retraction of the trocar and the closure of the anvil;
    set the anvil closure rate to a third velocity, which is less than the second velocity, to enable a verification of the attachment of the trocar to the anvil; and
    set the anvil closure rate to a fourth velocity, which is less than the third velocity, when the trocar is the fourth zone during the application of the high closure load.

4. The powered stapling device of claim 1, wherein the control circuit is further configured to verify an attachment of the trocar to the anvil and to slow a trocar closure rate under a tissue load.

5. The powered stapling device of claim 1, further comprising:
    a knife coupled to the motor;
    a sensor located on the anvil, wherein the sensor is configured to detect a tissue contact with the anvil and a force applied to the anvil, wherein the sensor is coupled to the anvil, and wherein the control circuit is further configured to:
        monitor an anvil displacement;
        monitor the tissue contact with the anvil;
        monitor a force to close the anvil;
        compare the force to close the anvil to a predetermined threshold; and set a first initial knife velocity and to advance the knife at a first velocity profile configured to cut a normal tissue toughness when the force to close the anvil is less than the predetermined threshold, or set a second initial knife velocity and to advance the knife at a second velocity profile configured to cut a heavy tissue toughness when the force to close the anvil is greater than or equal to the predetermined threshold.

6. The powered stapling device of claim 5, wherein to advance the knife at the second velocity profile, the control circuit is further configured to:

set the second initial knife velocity to a velocity that is less than the first initial knife velocity;

monitor a knife contact with tissue;

increase a motor velocity to increase a knife velocity when the knife contact with the tissue is detected;

monitor a completion of a cut; and stop the motor when the completion of the cut is detected.

* * * * *